(12) United States Patent
Volk et al.

(10) Patent No.: US 7,786,129 B2
(45) Date of Patent: Aug. 31, 2010

(54) PIPERAZINE DERIVATIVES OF DIALKYL OXINDOLES

(75) Inventors: Balázs Volk, Budapest (HU); József Barkóczy, Budapest (HU); Gyula Simig, Budapest (HU); Tibor Mezei, Budapest (HU); Rita Kapillerné Dezsöfi, Budapest (HU); Endréné Flórian, Budapest (HU); István Gacsályi, Budapest (HU); Katalin Pallagi, Budapest (HU); Gábor Gigler, Budapest (HU); György Lévay, Budakeszi (HU); Krisztina Móricz, Budapest (HU); Csilla Leveleki, Budapest (HU); Nóra Sziray, Budapest (HU); Gábor Szénási, Uröm (HU); András Egyed, Budapest (HU); László Gábor Hársing, Budapest (HU)

(73) Assignee: Egis Gyogyszergyar Nyrt, Budapest (HU)

( * ) Notice: Subject to any disclaimer, the term of this patent is extended or adjusted under 35 U.S.C. 154(b) by 699 days.

(21) Appl. No.: 11/596,473

(22) PCT Filed: May 11, 2005

(86) PCT No.: PCT/HU2005/000052

§ 371 (c)(1),
(2), (4) Date: Jun. 8, 2007

(87) PCT Pub. No.: WO2005/109987

PCT Pub. Date: Nov. 24, 2005

(65) Prior Publication Data

US 2007/0232619 A1  Oct. 4, 2007

(30) Foreign Application Priority Data

May 11, 2004 (HU) .................................. 0400957
May 5, 2005 (HU) .................................. 0500464

(51) Int. Cl.
*A61K 31/4045* (2006.01)
*C07D 209/34* (2006.01)
*C07D 401/12* (2006.01)
*C07D 405/12* (2006.01)

(52) U.S. Cl. .................. 514/254.09; 514/253.09; 544/364; 544/373

(58) Field of Classification Search ............ None
See application file for complete search history.

(56) References Cited

U.S. PATENT DOCUMENTS 5,010,079 A * 4/1991 Manoury et al. ........ 514/253.05

FOREIGN PATENT DOCUMENTS

| EP | 0354094 A | 2/1990 |
| WO | WO 98/08816 A1 | 3/1998 |
| WO | 2005/108363 | * 11/2005 |
| WO | WO-2005/108390 A1 | 11/2005 |

OTHER PUBLICATIONS

Roth et al. Expert Opin.Ther.Targets 5(6), p. 685-695 (2001).*
McCarthy et al. J.Chem.Soc.Chem.Commun. p. 1717-1719 (2001).*
Sakai et al., Yakugaku Zasshi, 95(12), 1976, pp. 1511-1516.
Boyd-Barrett et al., Journal of the Chemical Society, Abstracts, 1932, pp. 317-321.
Kapiller-Dezsofi et al., New Journal of Chemistry, vol. 28, No. 10, Aug. 17, 2004, pp. 1214-1220.

* cited by examiner

*Primary Examiner*—Emily Bernhardt
(74) *Attorney, Agent, or Firm*—Birch, Stewart, Kolasch & Birch, LLP.

(57) ABSTRACT

The present invention is concerned with new 3,3-disubstituted indol-2-one derivatives of the general Formula (I), wherein $R^1$ stands for hydrogen, halogen, alkyl having 1-7 carbon atom(s) or sulfonamido; $R^2$ represents hydrogen or halogen; $R^3$ denotes hydrogen, alkyl having 1-7 carbon atom(s) optionally carrying an aryl substituent or aryl optionally carrying one or two halogen substituent(s); $R^4$ stands for alkyl having 1-7 carbon atom(s); $R^5$ represents a group of the general Formula (II a) or (II b), wherein Q and W each represents nitrogen or CH; $R^6$, $R^7$ and $R^8$ each stands for hydrogen, halogen, trifluoromethyl, alkyl or alkoxy having 1-7 carbon atom(s), or $R^6$ and $R^7$ together represent ethylenedioxy; m is 0, 1, or 2; a is a single, double or triple bond; n is 0, 1 or 2; and pharmaceutically acceptable acid addition salts thereof which are useful in the treatment or prophylaxis of diseases of the central nervous system, the gastrointestinal system and the cardiovascular system.

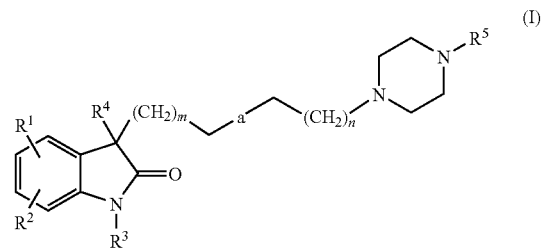

17 Claims, 1 Drawing Sheet

Effect of the compound of Example 76 on dopamine release in the internal ear of guinea pig y axis: fractional dopamine release (%)
x axis: fraction number

PIPERAZINE DERIVATIVES OF DIALKYL OXINDOLES

TECHNICAL FIELD OF THE INVENTION

The invention relates to new 3,3-disubstituted indol-2-one derivatives, a process for the preparation thereof, pharmaceutical compositions containing said new indol-2-one derivatives and the use of said compounds for the treatment of diseases.

More particularly the present invention is concerned with new 3,3-disubstituted indol-2-one derivatives of the general Formula (I),

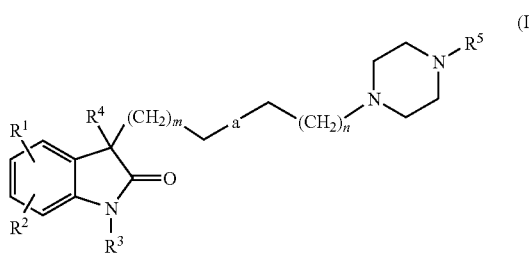

wherein
$R^1$ stands for hydrogen, halogen, alkyl having 1-7 carbon atom(s) or sulfonamido;
$R^2$ represents hydrogen or halogen;
$R^3$ denotes hydrogen, alkyl having 1-7 carbon atom(s) optionally carrying an aryl substituent or aryl optionally carrying one or two halogen substituent(s);
$R^4$ stands for alkyl having 1-7 carbon atom(s);
$R^5$ represents a group of the general Formula (II a) or (II b),

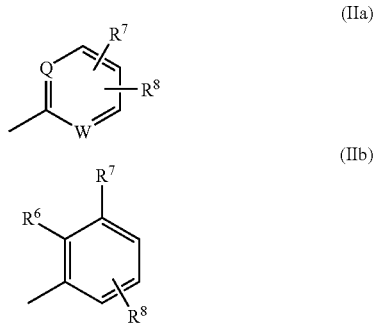

wherein Q and W each represents nitrogen or CH;
$R^6$, $R^7$ and $R^8$ each stands for hydrogen, halogen, trifluoromethyl, alkyl or alkoxy having 1-7 carbon atom(s), or
$R^6$ and $R^7$ together represent ethylenedioxy;
m is 0, 1, or 2;
a is a single, double or triple bond;
n is 0, 1 or 2;
and pharmaceutically acceptable acid addition salts thereof.

TECHNICAL BACKGROUND OF THE INVENTION

U.S. Pat. No. 4,452,808 discloses 4-aminoalkyl-indol-2-one derivatives having a selective $D_2$ receptor activity. These compounds can be used for the treatment of hypertension. One of the compounds provided by this patent, namely 4-[2-(di-N-propylamino)ethyl]-2(3H)-indolone, is used for the clinical treatment of Parkinson disease.

European patent No. 281,309 provides indol-2-one derivatives carrying an arylpiperazinyl-alkyl substituent in position 5, which can be applied for the treatment of psychotic conditions. One of the compounds described in this patent, namely 5-[2-[4-(1,2-benzisothiazol-3-yl)-1-piperazinyl]-ethyl]-6-chloro-1,3-dihydro-2H-indol-2-one, exerts its activity by interaction with $D_2$, $5-HT_{1A}$ and $5-HT_2$ receptors and is used in the clinical treatment as an antipsychotic agent.

European patent No. 376,607 discloses indol-2-one derivatives substituted in position 3 by an alkylpiperazinyl aryl group, which exert their activity on $5-HT_{1A}$ receptors and are useful for the treatment of central nervous disorders.

In the international patent application WO 98/008816 indol-2-one derivatives containing a substituted alkyl-piperazinyl, substituted alkyl-piperidinyl or alkyl-cyclohexyl group in position 3 are disclosed. These compounds possess psychotrophic activity.

The acceleration of technical-social development in the XX. century constitutes a permanent compulsion of adaptation for humans, which, in adverse cases, my lead to the occurrence of adaptation disorders. Adaptation disorders constitute an important risk factor in the development of diseases of mental or psycho-somatic origin, such as anxiolytic syndrome, stress disorder, depression, schizophrenia, disorders of the sense organs, gastrointestinal diseases, cardiovascular diseases, renal disorders.

For the treatment of the above clinical patterns most widespreadly pharmaceuticals exerting their activity on the benzodiazepine system (e.g. diazepam) or on central $5-HT_{1A}$ receptors (e.g. buspiron, ziprasidon) have been applied. In case of psychosomatic diseases anxiolytic therapy is often complemented by the administration of pharmaceuticals possessing antihypertensive (acting on the $\alpha_1$ or $\alpha_2$ receptor), or antiulcer ($H_1$-receptor antagonist) activity.

Anxiolytics of benzodiazepine type are accompanied, however, by several unpleasant side-effects. They have a strong sedative activity, cause decline of the power of concentration and memory and possess muscle relaxant effect. Said side-effects influence the quality of life of the patients in an adverse manner restricting the scope of application of such pharmaceuticals.

The pharmaceuticals acting on the $5-HT_{1A}$ receptors that have been so far applied in the therapy are accompanied, however, by several drawbacks and undesired side-effects. It is a drawback that the anxiolytic effect can be achieved only after a treatment lasting for at least 10-14 days. Besides, after the initial administration an anxiogenic effect occurs. As to the side-effects, the occurrence of sleepiness, somnolence, vertigo, hallucination, headache, cognitive disorders or nausea has often been observed. Such effects of the pharmaceuticals render the co-operation between physicians and patients much more difficult, because the patients are in the belief that the worsening of their symptoms is a consequence of the drug administration.

Beside the stress occurring during adaptation to the environment another great problem of modern societies is the rapid ageing of population. Owing to the results of modern medical science life expectancy has increased, and the diseases occurring due to ageing or developing in the declining years, particularly the number of mental diseases has grown in leaps and bounds. The solution of the treatment of Alzheimer's disease, vascular dementias and senile dementia has become a social problem.

Another consequence of ageing processes is the considerable increase in the number of auditory disturbances. According to WHO statistics, in 2001, 250 million people suffered from moderate or severe auditory dysfunction. Senile auditory disturbances can be evidenced in 10% and 25% of the 45-55 year old and 65-75 year old population, respectively.

As a result of the enumerated processes there is a strong need for new and efficient pharmaceuticals ensuring a more effective treatment of these diseases than those available for the time being.

SUMMARY OF THE INVENTION

The object of the present invention is to develop pharmaceutical ingredients which are devoid of the above-specified drawbacks and undesired side-effects characteristic of the active agents binding to $5-HT_{1A}$ receptors and which, at the same time, can be used for the treatment of disorders of the central nervous system. The invention is based on the recognition that the 3,3-dialkyl-substituted indol-2-one derivatives of the general Formula (I) possess a significant anxiolytic effect, but surprisingly—in contrast to the prior art compounds of similar structure—do not bind to $5-HT_{1A}$ receptors. As an advantageous consequence, the compounds according to the invention are devoid of the above-listed side-effects of the compounds binding to said receptors. Besides, surprisingly it has been found that the compounds of the general Formula (I) according to the invention bind to $5-HT_{2C}$ and $\alpha_1$ receptors, too, and evoke dopamine release, which activities considerably widen the scope of therapeutic application.

DETAILED DESCRIPTION OF THE INVENTION

According to an aspect of the present invention there are provided novel 3,3-disubstituted indol-2-one derivatives of the general Formula (I), wherein
$R^1$ stands for hydrogen, halogen, alkyl having 1-7 carbon atom(s) or sulfonamido;
$R^2$ represents hydrogen or halogen;
$R^3$ denotes hydrogen, alkyl having 1-7 carbon atom(s) optionally containing an aryl substituent or aryl optionally containing one or two halogen substituent(s);
$R^4$ stands for alkyl having 1-7 carbon atom(s);
$R^5$ represents a group of the general Formula (II a) or (II b), wherein Q and W each represents nitrogen or CH;
$R^6$, $R^7$ and $R^8$ each stands for hydrogen, halogen, trifluoromethyl, alkyl or alkoxy having 1-7 carbon atom(s), or
$R^6$ and $R^7$ together represent ethylenedioxy;
m is 0, 1, or 2;
a is a single, double or triple bond;
n is 0, 1 or 2;

and pharmaceutically acceptable acid addition salts thereof.

The term "alkyl" used throughout this specification is intended to mean straight or branched chain saturated hydrocarbon groups having 1 to 7, preferably 1 to 4 carbon atom(s), (e.g. methyl, ethyl, 1-propyl, 2-propyl, n-butyl, isobutyl or tert. butyl group etc.)

The term "halogen" encompasses the fluorine, chlorine, bromine and iodine atoms and is preferably chlorine or bromine.

The leaving group can be an alkylsulfonyloxy or arylsulfonyloxy group, e.g. methylsulfonyloxy or p-toluenesulfonyloxy group; or a halogen atom, preferably bromine or chlorine.

The term "pharmaceutically acceptable acid addition salts" relates to non-toxic salts of the compounds of the general Formula (I) formed with pharmaceutically acceptable organic or inorganic acids. Inorganic acids suitable for salt formation are e.g. hydrogen chloride, hydrogen bromide, phosphoric, sulfuric or nitric acid. As organic acids formic, acetic, propionic, maleic, fumaric, succinic, lactic, malic, tartaric, citric, ascorbic, malonic, oxalic, mandelic, glycolic, phtalic, benzenesulfonic, p-toluene-sulfonic, naphthalic or methanesulfonic acids can be used. Furthermore, carbonates and hydro-carbonates are also considered as pharmaceutically acceptable salts.

To a subgroup of the compounds of the general Formula (I) possessing valuable pharmaceutical properties belong the compounds wherein
$R^1$ stands for hydrogen, halogen, alkyl having 1-7 carbon atom(s) or sulfonamido;
$R^2$ represents hydrogen or halogen;
$R^3$ is hydrogen;
$R^4$ stands for ethyl- or 2-methylpropyl;
$R^5$ represents a group of the general Formula (II a) or (II b), wherein Q stands for nitrogen and W is a CH group;
$R^6$, $R^7$ and $R^9$ each represents hydrogen, halogen or alkoxy having 1-7 carbon atom(s), or
$R^6$ and $R^7$ together form an ethylenedioxy group;
m is 0 or 1;
a stands for a single bond;
n is 1;

and pharmaceutically acceptable acid addition salts of the compounds of the general Formula (I).

To a subgroup of the compounds of the general Formula (I) possessing particularly preferable activity belong the derivatives wherein
$R^1$ stands for hydrogen or halogen;
$R^2$ represents hydrogen or halogen;
$R^3$ is hydrogen;
$R^4$ represents ethyl;
$R^5$ is a group of the general Formula (II a);
$R^6$, $R^7$ and $R^8$ each represents hydrogen, halogen or alkoxy having 1-7 carbon atom(s);
m is 1;
a stands for a single bond;
n is 0 or 1;

and pharmaceutically acceptable acid addition salts of the compounds of the general Formula (I).

Another subgroup of the compounds of the general Formula (I) possessing particularly preferable activity comprises the derivatives wherein
$R^1$ is hydrogen, halogen, alkyl having 1-7 carbon atom(s) or sulfonamido;
$R^2$ is hydrogen;
$R^3$ is hydrogen;
$R^4$ is ethyl- or 2-methylpropyl;
$R^5$ stands for a group of the general Formula (II a);
$R^6$, $R^7$ and $R^8$ each represents hydrogen, halogen, alkoxy having 1-7 carbon atom(s), or
$R^6$ and $R^7$ together form an ethylenedioxy group;
m is 1;
a is a single bond;
n is 1;

and pharmaceutically acceptable acid addition salts thereof.

According to a further aspect of the present invention there is provided a process for the preparation of the compounds of the general Formula (I) and pharmaceutically acceptable acid addition salts thereof, which comprises (a) reacting a compound of the general Formula (III),

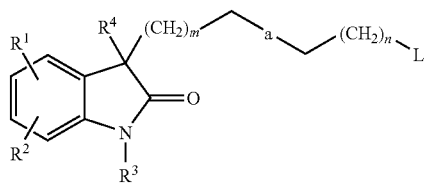

wherein L is a leaving group, preferably chlorine or bromine, m and n each stands for 0, 1 or 2 and a is a single, double or triple bond, with a piperazine derivative of the general Formula (IV)

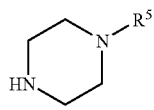

wherein $R^5$ is as stated above,
in the presence of an acid binding agent; or
(b) reacting a compound of the general Formula (VI),

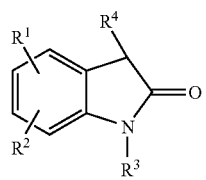

wherein $R^1$, $R^2$, $R^3$ and $R^4$ are as stated above, with a compound of the general Formula (VII),

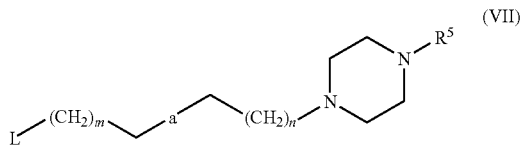

wherein m and n each stands for 0, 1 or 2, a represents a single, double or triple bond and L is a leaving group, preferably chlorine or bromine, in the presence of a strong base; or
(c) for the preparation of compounds of the general Formula (I), wherein n is 1 and a stands for a triple bond, reacting a compound of the general Formula (VIII),

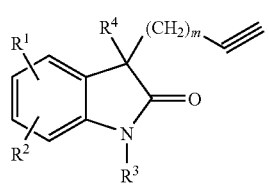

wherein $R^1$, $R^2$, $R^3$, $R^4$ and m are as stated above, with formaldehyde, optionally converting the thus-obtained compound of the general Formula (III), wherein L stands for a hydroxy group, into a compound of the general Formula (III), wherein L is a halogen atom or an arylsulfonyloxy or alkylsulfonyloxy group, and reacting the thus-obtained compound of the general Formula (III), wherein a is a triple bond and n is 1, with a compound of the general Formula (IV) in the presence of a strong base; or
(d) for the preparation of the compounds of the general Formula (I), wherein $R^1$, $R^2$, $R^3$, $R^4$, $R^5$, m and n are as stated above and a stands for a single or double bond, subjecting the corresponding compound of the general Formula (I), wherein a stands for a triple bond, to reduction; or
(e) for the preparation of the compounds of the general Formula (I), wherein $R^1$, $R^2$, $R^3$, $R^4$, $R^5$, m and n are as stated above and a represents a single bond, subjecting the corresponding compound of the general Formula (I), wherein a stands for a double or triple bond, to reduction, and, if desired, halogenating the product containing hydrogen in the place of $R^2$, or liberating the free base from its salt or converting it into a pharmaceutically acceptable acid addition salt with an organic or inorganic acid.

The compounds of the general Formula (I), wherein $R^1$-$R^5$, a, m and n are as stated above, can be prepared by reacting a compound of the general Formula (III), wherein $R^1$-$R^4$, a, m and n are as stated above and L is a leaving group, with a compound of the general Formula (IV), wherein $R^5$ is as stated above, in manners analogous to those known from the literature [Houben-Weyl: Methoden der organischen Chemie, Georg Thieme Verlag, Stuttgart, 1992, 4$^{th}$ Edition, vol. E16d (D. Klamann); R. C. Larock: Comprehensive Organic Transformations, 2$^{th}$ Edition, John Wiley & Sons, New York, 1999, 789; D. A. Walsh, Y-H, Chen, J. B. Green, J. C. Nolan, J. M. Yanni J. Med. Chem. 1990, 33, 1823-[827].

During the preparation of the compounds of the general Formula (III) the formation of the substituents can be carried out in optional succession according to methods known from the literature. It is expedient to prepare the compounds of the general Formula (III) by reacting a compound of the general Formula (V),

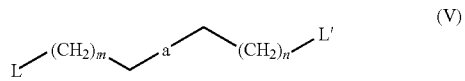

—wherein L, a, m and n are as stated above and L' is a leaving group or a group that can be converted into a leaving group— with a compound of the general Formula (VI), wherein $R^1$-$R^4$ are as stated above, which has been composed according to methods known from the literature [Houben-Weyl: Methoden der organischen Chemie, Georg Thieme Verlag, Stuttgart, 1977, 4$^{th}$ Edition, vol. V/2b; A. R. Katritzky, Ch. W. Rees: Comprehensive Heterocyclic Chemistry, 1$^{th}$ Edition, Pergamon, Oxford, 1984, vol. 4. (ed.: C. W. Bird, G. W. H. Cheeseman), 98-150 and 339-366; G. M. Karp Org. Prep. Proc. Int. 1993, 25, 481-513; B. Volk, T. Mezei, Gy. Simig Synthesis 2002, 595-597].

The compounds of the general Formula (I), wherein $R^1$-$R^5$, a, m and n are as stated above, can also be prepared by reacting a compound of the general Formula (VI)—wherein $R^1$-$R^4$ are as stated above—with a compound of the general Formula (VII)—wherein $R_5$, a, m and n are as stated above and L is a leaving group—according to methods known from the literature [R. J. Sundberg: The chemistry of indoles, Academic Press, New York, 1970, chapter VII.; G. M. Karp *Org. Prep. Proc. Int.* 1993, 25, 481-513; A. S. Kende, J. C. Hodges *Synth. Commun.* 1982, 12, 1-10; W. W. Wilkerson, A. A. Kergaye, S. W. Tam *J. Med. Chem.* 1993, 36, 2899-2907].

The compounds of the general Formula (I), wherein $R^1$-$R^5$ and m are as stated above, a is a triple bond and n is 1, can also be prepared by reacting a compound of the general Formula (VIII) —wherein $R^1$-$R^4$ and m are as stated above—in the presence of formaldehyde with a compound of the general Formula (IV)—wherein $R^5$ is as stated above—by methods known from the literature [Houben-Weyl: Methoden der organischen Chemie, Georg Thieme Verlag, Stuttgart, 1977, $4^{th}$ Edition, vol. V/2a (ed.: E. Müller), 545-549; B. M. Trost, I. Fleming: Comprehensive Organic Syntheses, $1^{th}$ Edition, Pergamon Press, Oxford, 1991, vol. 2 (ed.: C. H. Heathcock), 893-898; K Ishizumi, A. Kojima, F. Antoku *Chem. Pharm. Bull.* 1991, 39, 2288-2300].

In certain cases this reaction can also be performed in several steps, namely by reacting in the first step the compound of the general Formula (VIII)—wherein $R^1$-$R^4$ and m are as stated above—with formaldehyde and obtaining a compound of the general Formula (II), wherein $R^1$-$R^4$ and m are as stated above, n is 1, a is triple bond and L is hydroxy. The thus-obtained compound is then reacted either directly with the compound of the general Formula (IV), or the L=OH group is converted first into a more suitable leaving group by methods known from the literature and then reacted with a compound of the general Formula (IV) to obtain a compound of the general Formula (I), wherein $R^1$-$R^5$ and m are as stated above, a is a triple bond and n is 1.

The compounds of the general Formula (I), wherein $R^1$-$R^5$, m and n are as stated above and a is a single or double bond, can also be prepared by reducing a compound of the general Formula (I), wherein $R^1$-$R^5$, m and n are as stated above and a is a triple bond, by methods known from the literature [Houben-Weyl: Methoden der organischen Chemie, Georg Thieme Verlag, Stuttgart, 1980, $4^{th}$ Edition, vol. IV/1c and IV/1d (ed.: H. Kropf); J. March: Advanced Organic Chemistry, Reactions, mechanisms and structure, $4^{th}$ Edition, John Wiley & Sons, New York, 1992, 771-780].

The compounds of the general Formula (I), wherein $R^1$-$R^5$, m and n are as stated above and a is a single bond, can also be prepared by reducing a compound of the general Formula (I), wherein $R^1$-$R^5$, m and n are as stated above and a is a double bond, according to methods known from the literature [Houben-Weyl: Methoden der organischen Chemie, Georg Thieme Verlag, Stuttgart, 1980, $4^{th}$ Edition, vol. IV/1c and IV/1d (ed.: H. Kropf); J. March: Advanced Organic Chemistry, Reactions, mechanisms and structure, $4^{th}$ Edition, John Wiley & Sons, New York, 1992, 771-780].

The compounds of the general Formula (I), wherein $R^1$-$R^5$, a, m and n are as stated above, can also be prepared by carrying out the formation of the substituents $R^1$-$R^8$ in different succession in the last reaction step. In this case a compound of the general Formula (I) is used as starting substance wherein all substituents are as stated above except the one to be formed. The introduction and conversion of the substituents are carried out according to methods known from the literature [Houben-Weyl: Methoden der organischen Chemie, Georg Thieme Verlag, Stuttgart, 1977, $4^{th}$ Edition, IV/1a-d; vol. V/2b]. During the introduction of the substituents application or elimination of protecting groups may become necessary. Such methods are specified in T. W. Greene, Protective groups in organic synthesis, John Wiley & Sons, 1981.

The compounds of the general Formulae (IV), (V) and (VII) are known from the literature or can be prepared by analogous methods.

The compounds of the general Formula (VI), wherein $R^1$-$R^4$ are as stated above, can be produced by known methods, the formation of the substituents is carried out in optional succession according to methods known from the literature [A. R. Katritzky, Ch. W. Rees: Comprehensive Heterocyclic Chemistry, $1^{th}$ Edition Pergamon, Oxford, 1984, vol. 4 (ed.: C. W. Bird, G. W. H. Cheeseman), 98-150 and 339-366; C. Gautier, M. Aletru, Ph. Bovy WO 99/62900; B. Volk, T. Mezei, Gy. Simig *Synthesis* 2002, 595-597; G. M. Karp *Org. Prep. Proc. Int.* 1993, 25, 481-513; A. S. Kende, J. C. Hodges *Synth. Commun.* 1982, 12, 1-10].

During the preparation of compounds of the general Formula (VIII), wherein $R^1$-$R^4$ are as stated above and m is 1, 2 or 3, the introduction of the substituents $R^1$-$R^4$ and —$(CH_2)_m$—C≡CH can be performed in optional succession according to methods known from the literature [A. R. Katritzky, Ch. W. Rees: Comprehensive Heterocyclic Chemistry, $1^{th}$ Edition, Pergamon, Oxford, 1984, vol. 4 (ed.: C. W. Bird, G. W. H. Cheeseman), 98-150 and 339-366; C. Gautier, M. Aletru, Ph. Bovy WO 99/62900; B. Volk, T. Mezei, Gy. Simig *Synthesis* 2002, 595-597; G. M. Karp *Org. Prep. Proc. Int.* 1993, 25, 481-513; A. S. Kende, J. C. Hodges *Synth. Commun.* 1982, 12, 1-10]. The compound of the general Formula (VIII) is preferably prepared by alkylating a compound of the general Formula (VI)—wherein $R^1$-$R^4$ are as stated above—with a compound of the general Formula (IX), wherein m is 1, 2 or 3 and L is a leaving group, according to methods known from the literature.

The compounds of the general Formula (I) prepared by the methods according to the invention can be liberated from their salts or converted into pharmaceutically acceptable acid addition salts by methods known from the literature.

According to a further aspect of the present invention there are provided pharmaceutical compositions comprising as active ingredient a compound of the general Formula (I) or a pharmaceutically acceptable acid addition salt thereof in admixture with one or more conventional carrier(s) or auxiliary agent(s).

The pharmaceutical compositions according to the present invention contain generally 0.1-95% by weight, preferably 1-50% by weight, particularly preferably 5-30% by weight of the active ingredient.

The pharmaceutical compositions of the present invention may be suitable for oral (e.g. powders, tablets, coated tablets, capsules, microcapsules, pills, solutions, suspensions or emulsions), parenteral (e.g. injection solutions for intravenous, intramuscular, subcutaneous or intraperitoneal use), rectal (e.g. suppositories) transdermal (e.g. plasters) or local (e.g. ointments or plasters) administration or for the application in form of implants. The solid, soft or liquid pharmaceutical compositions according to the invention may be produced by methods conventionally applied in the pharmaceutical industry.

The solid pharmaceutical compositions for oral administration containing the compounds of the general Formula (I) or pharmaceutically acceptable acid addition salts thereof may comprise fillers or carriers (such as lactose, glucose, starch, potassium phosphate, microcrystalline cellulose), binding agents (such as gelatine, sorbite, polyvinyl pyrrolidone), disintegrants (such as croscarmelose, Na-carboxymethyl cellulose, crospovidone), tabletting auxiliary agents (such as magnesium stearate, talc, polyethylene glycol, silicic acid, silica dioxide) and surface-active agents (e.g. sodium lauryl sulfate).

The liquid compositions suitable for oral administration can be solutions, suspensions or emulsions. Such compositions can contain suspending agents (e.g. gelatine, carboxymethyl cellulose), emulsifiers (e.g. sorbitane monooleate, solvents (e.g. water, oils, glycerol, propylene glycol, ethanol), buffering agents (e.g. acetate, phosphate, citrate buffers) and preservatives (e.g. methyl-4-hydroxybenzoate etc.).

Liquid pharmaceutical compositions suitable for parenteral administration are generally sterile isotonic solutions optionally containing, in addition to the solvent, buffering agents and preservatives.

Soft pharmaceutical compositions containing as active ingredient a compound of the general Formula (I) or a pharmaceutically acceptable acid addition salt thereof, such as suppositories, contain the active ingredient evenly dispersed in the basic material of the suppository (e.g. in polyethylene glycol or cocoa butter).

According to a further aspect of the present invention there is provided the use of an indol-2-one derivative of the general Formula (I) or a pharmaceutically acceptable acid addition salt thereof for the preparation of pharmaceutical compositions suitable for the treatment or prophylaxis of disorders of the central nervous system or psychosomatic disorders including anxiety syndromes, particularly generalized anxiety disorders, panic disease, compulsive disease, social phobia, agoraphobia, phobias connected to specific situations, post-traumatic stress disorder, post-traumatic memory disturbances, cognitive disturbances, sexual dysfunction originating of central nervous system origin, depression, schizophrenia, gastrointestinal diseases and cardiovascular diseases.

The pharmaceutical compositions according to the present invention can be prepared by known methods of the pharmaceutical industry. The active ingredient is admixed with pharmaceutically acceptable solid or liquid carriers and/or auxiliary agents and the mixture is brought to galenic form. The carriers and auxiliary agents together with the methods which can be used in the pharmaceutical industry are disclosed in the literature (Remington's Pharmaceutical Sciences, Edition 18, Mack Publishing Co., Easton, USA, 1990).

The pharmaceutical compositions according to the present invention contain generally a dosage unit. The daily dosage for human adults can be generally 0.1-1000 mg/kg body weight of a compound of the general Formula (I) or a pharmaceutically acceptable acid addition salts thereof. Said daily dose can be administered in one or more portion(s). The actual daily dose depends on several factors and is determined by the physician.

According to a further aspect of the present invention there is provided the use of the compounds of the general Formula (I) or pharmaceutically acceptable acid addition salts thereof for the treatment or prophylaxis of disorders of the central nervous system and psychosomatic disorders including anxiety syndrome, particularly generalized anxiety disorders, panic disease, compulsive disease, social phobia, agoraphobia, phobias in connection with specific situations, stress disorder, post-traumatic stress disorder, post-traumatic memory disturbances, cognitive disturbances, sexual dysfunction of central nervous system origin, depression, schizophrenia, mental decline followed by cerebellar cell death, Alzheimer's disease, stroke, dementias, further-more gastrointestinal diseases and cardiovascular diseases, particularly hypertension. The compounds according to the invention can also be used for the treatment of disorders of the auditory organ developing as a consequence of a healing therapy, the treatment of tinnitus.

It is known from the European patent specification No. 376.607 and from the technical literature (A. Dekeyne, J. M. Rivet, A. Gobert, M. J. Millan: Neuropharmacology 40(7) p. 899-910 (2001); J. S: Sprouse et al.: Neuropsycho-pharmacology 21(5) p. 622-631 (1999); A. Newman-Tancredi et al.: Eur. J. Pharmacol. 355(2-3) pp. 245-246 (1998)) that the prior art compounds of 1,3-dihydro-2H-indol-2-one type bind to the 5-$HT_{1A}$ receptor in a selective manner, and thus affect the central nervous system. Accordingly, they can be used for the treatment of anxiolytic disorders, depression, furthermore cardiovascular, gastrointestinal and renal disorders.

The present invention is based on the surprising recognition that the 3,3-dialkyl indol-2-one derivatives of the general Formula (I) possess anxiolytic activity, but do not bind to 5-$HT_{1A}$ receptors. That is why it can be expected that the compounds according to the invention are devoid of the above-mentioned adverse side-effects characteristic to the active ingredients binding to 5-$HT_{1A}$ receptors. Another surprising recognition is that the compounds of the general Formula (I), besides their anxiolytic activity that can be brought in connection with their binding to 5-$HT_{2C}$ receptors, affect the dopamine release in the ear and also bind to $\alpha_1$ receptors.

Receptor bindings—with the exception of the 5-$HT_{2C}$ receptor binding—were determined by using cerebral region preparations of male Wistar rats weighing 120-200 g. For the preparation of 5-$HT_{1A}$ receptor binding frontal cortex preparations were used. The al receptor binding studies were performed from isolated frontal cortex pre-parations. For the 5-$HT_{2C}$ receptor binding experiments choroid plexus of pigs was used. The protein contents of membrane preparations were determined by the method of Lowry (1951).

5-$HT_{1A}$ receptor binding was measured according to the method of Peroutka (Peroutka, S. J.: J. Neurochem. 47, p. 529 (1986)). The ligand was tritiated 8-hydroxy-N,N-dipropyl-2-aminotetraline (8-OH-DPAT). For the determination of non-specific binding 10 µM serotonin was applied. Incubation blood volume was 250 µl. Incubation was carried out at a temperature of 25 C for 30 minutes. The reaction was terminated by the addition of 9 ml of ice-cold 50 mM TRIS-HCl (pH 7.7) buffer and quick vacuum filtration using Whatman GFIB fibreglass filtering paper. Radioactivity of the filter boards was measured by liquid scintillation spectrometry.

In the course of 5-$HT_{2C}$ and $\alpha_1$ receptor binding experiments the ligands were $^3$H-mesulergin (1.0 nM) and $^3$H-prazosine (0.3 nM), respectively. The non-specifically binding ligands were mianserine (1 µM and prazosine (1 µM), respectively.

The $IC_{50}$ value is the value of concentration where the difference between total and non-specific binding is 50% in the presence of a determined concentration of a specific ligand. The compounds with an $IC_{50}$ value less than 100 mmoles were considered to be effective in the test. The results are given in Tables 1 to 3.

TABLE 1

| -$HT_{1A}$ receptor binding | |
|---|---|
| No. of Example | $IC_{50}$ nmole |
| 61. | >200 |
| 68. | >200 |
| 72. | >200 |
| 75. | >200 |
| 78. | >200 |
| 79. | >400 |
| 86. | >300 |
| 89. | >300 |
| 90. | >300 |
| 87. | >400 |

TABLE 1-continued

5-HT$_{1A}$ receptor binding

| No. of Example | IC$_{50}$ nmole |
|---|---|
| 95. | >300 |
| 96. | >400 |

From the results disclosed in Table 1 it can be seen that the test compounds do not bind to 5-HT$_{1A}$ receptors.

TABLE 2

5-HT$_{2C}$ receptor binding

| No. of Example | IC$_{50}$ nmole |
|---|---|
| 57. | <50 |
| 61. | <100 |
| 68. | <100 |
| 72. | <100 |
| 78. | <100 |

TABLE 3

α$_1$ receptor binding experiment

| No. of Example | IC$_{50}$ nmol |
|---|---|
| 59. | <100 |
| 60. | <100 |
| 62. | <100 |
| 63. | <50 |
| 64. | <50 |
| 69. | <50 |
| 61. | <100 |
| 68. | <100 |
| 72. | <30 |
| 75. | <100 |
| 78. | <100 |

As it can be established from Tables 2 and 3, the compounds according to the invention show considerable binding to 5-HT$_{2C}$ and α$_1$ receptors.

The anxiolytic effect of the compounds according to the invention was investigated on rats according to Vogel's drinking conflict test and elevated plus-maze test (S. Pelow, P. Chopin, S. E. File, J. Briley: Neurosci. Methods 14, p. 149 (1985)).

Vogel's Drinking Conflict Test

Male Wistar rats weighing 160-180 g were used for the experiment. The animals were deprived of drinking water for 48 hours and fasted for 24 hours prior to test. The test compounds or vehicle were administered intraperitoneally, 30 min prior to test. In the test chamber the animals had a free access to drinking water. Following every 20 licks electric shocks (0.7 mA) were applied through the drinking spout during the 5 min test period. The number of punished licks were recorded. The effect of the test compounds was expressed as % increase in numbers of tolerated shocks. Minimal effective doses (MED) were determined for each compound. The results are given in Table 4.

TABLE 4

Vogel's drinking conflict test

| No. of Example | MED mg/kg i.p. |
|---|---|
| 68. | 10 |
| 69. | 10 |
| 71. | 20 |
| 75. | 10 |
| 76. | 10 |
| 85. | 5 |
| 87. | 5 |
| 95. | 10 |

Elevated Plus-Maze Test in Rats

A wooden cross elevated to 50 cm above the floor, 15 cm wide with 100 cm long arms was used for the experiments. The sides and ends of two opposite arms of the cross were equipped with 40 cm high walls, however, the arms were open to the 15×15 cm central area (closed arms). The two other opposite arms were not encircled by walls (open arms).

Male Sprague-Dawley rats weighing 200-220 g were used for the experiments. The animals were placed in the central area of the equipment 60 min after treatment and the following four parameters have been observed for the 5 min test time:

time spent in the open arms (sec),
time spent in the closed arms (see),
number of entries into the open arms,
number of entries into the closed arms.

The effect was expressed as percent increase in either the time spent in the open arms or number of entries into the open arms. MEDs (minimal effective doses) were determined for each compound. The results are summarized in Table 5.

TABLE 5

Elevated plus-maze in rats

| Compound (No. of Example) | MED (mg/kg p.o.) |
|---|---|
| 85 | 0.1 |
| 87 | 0.3 |
| 95 | 0.1 |

From the data of the above tables it can be seen that the compounds of the general Formula (I) possess significant anxiolytic effect.

The study of the effect on the hearing impairment and tinnitus were performed in guinea pigs weighing 145-375 g (Toxicoop, Hungary) according to the method of Gáboiján et al. (Gáboiján, A., Lendvai, B, Vizi, E. S.: Neuroscience 90, p. 131 (1999)). The dopamine release in the internal ear, as a correlate of hearing impairment, was measured in samples from cochlear preparations (lateral olivocochlear efferents) with high-pressure liquid chromatography (HPLC). The samples were collected in every 3 minutes during 60 minutes (20 fractions). Electric field stimulation was generally applied during the 3$^{rd}$ and 13$^{th}$ fraction (S1, S2, 2 Hz, 360 shocks, 60 V; Grass Medical Instruments). In the respective experiments ischemia (oxygen and glucose deprivation, OGD) was mimicked by the perfusion of a buffer saturated with 100% N2 and containing sacharose instead of glucose. Results are expressed as a percent of dopamine release per fraction. Statistical analysis was performed by analysis of variance (ANOVA) followed by Tukey test.

BRIEF DESCRIPTION OF THE DRAWING

From the thus-obtained results the effect of the compound of Example 76 on the dopamine release in the internal ear of guinea pig is shown (FIG. 1). The initial stimulation (SI) evoked considerable dopamine release. This release is decreased after the second stimulation after the oxygen and glucose deprivation, but in the presence of the compound of Example 76 the release stabilized at a significantly higher level than without oxygen and glucose deprivation. This effect can be interpreted as an inhibition of hearing impairment.

The neuroprotective effect of the compounds according to the invention was demonstrated in a model of global cerebral ischemia induced by bilateral carotid occlusion. Male Mongolian gerbils weighing 60-90 g were used as test animals. The test compounds were administered intraperitoneally at a dose of 30 mg/kg 45 min after surgery. Test substances were suspended in 0.4% methylcellulose solution. In diethylether narcosis, the right and left common carotid arteries were exposed through an anterior midline cervical incision and isolated from the vagus nerves and the surrounding tissues. Full arrest of carotid blood flow was achieved by tightening an aneurysm clip for 3 min. During surgery the body temperature of the animals was kept at the individual preoperative level (37.5±0.5° C.) with the help of a heating pad and a heating lamp.

Figure 1:
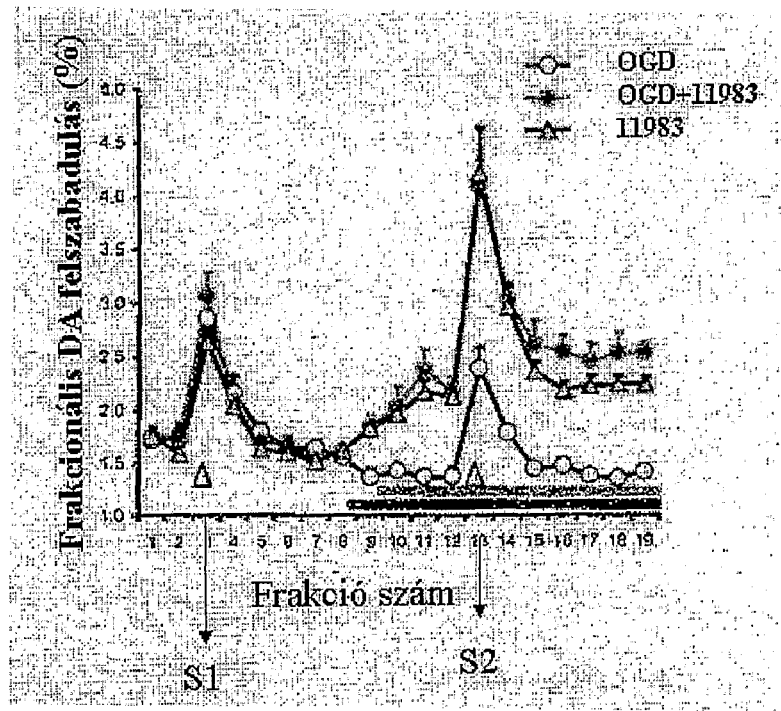

4 days after the surgery the animals were anaesthetized with 60 mg/kg i.p nembutal (10 ml/kg) and perfused through the heart first with saline then with a fixative solution containing 0.1% glutaraldehyde, 4% paraformaldehyde and 0.2% picric acid in 0.1 M phosphate buffer (pH 7.4) for 30 min. The brain was removed from the skull and post fixed for at least 1 week at 4° C. in the same fixative solution.

Alternate coronal sections of 60 µm thickness were cut from different levels of the dorsal hippocampus by a microtome. The sections were repeatedly washed in 0.1 M phosphate buffer (pH 7.4) and stained by silver impregnation. The sections were stored twice in a preparatory solution (2% sodium hydroxide and 0.875% ammonium hydroxide solution) for 5 minutes, impregnated for 10 minutes in 0.875% ammonium hydroxide and 0.5% silver nitrate solution) and placed into a washing solution (0.5% sodium carbonate and 0.01% ammonium nitrate dissolved in a 29.1% aqueous ethanol solution) twice for 2 minutes and once for one minute. The slices were then developed in 9.9% ethanol solution containing 1.5% formaldehyde and 0.01% ammonium nitrate and fixed three times for 3 minutes in a 0.5% acetic acid solution. The stained slices were placed in 0.1M phosphate buffer (pH 7.4) and chrome gelatine, applied on plates, dehydrated and treated with xylol. The cover plates were fixed with DPX glue (Fluka).

The sections were examined under light microscopy and the overall neuronal damage in the hippocampal CA1 subfield in both hippocampi was scored on a 6-point scale: (O) undamaged, (1)—0-10%; (2)—10-30%; (3)—30-50%; (4)—50-70%; (5)—70-90%; (6)—90-100% cell loss. Group differences between drug-treated and vehicle-treated groups were statistically analysed by Mann-Whitney U-test. The results are summarized in Table 6.

TABLE 6

Neuroprotective effect in global ischemia test

| Compound | Dose (mg/kg) i.p. | CA1 cell loss (score) | Effect (%) |
| --- | --- | --- | --- |
| Control | — | 5.00 | |
| Compound of Example 76 | 30 | 2.40* | −52 |
| Control | — | 5.00 | |
| Compound of Example 85 | 30 | 2.70* | −46 |
| Control | — | 4.40 | |
| Compound of Example 90 | 30 | 2.73* | −38 |

*$p < 0.05$, vs. control, Mann-Whitney U-test

The results of the above experiments demonstrate that the compounds according to the invention significantly decrease the cell death in the CA1 region of hippocampus in animals got over global cerebral ischemia. These results prove that the test compound possess a significant neuroprotective activity.

On the basis of the above experiments the new compounds according to the invention may prove to be effective for the treatment of certain disorders of the central nervous system and cardiovascular system. Such central nervous system disorders include different forms of anxiety (generalized anxiety disease, compulsive disorder, panic disease, post-traumatic stress disorder, social phobia, depression, mental decline followed by cerebellar cell death (e.g. Alzheimer's disease, stroke, dementias). Besides, the compounds according to the invention are suitable for the treatment of cardiovascular diseases, particularly hypertension. Further effects of the compounds according to the invention include hearing impairment and tinnitus occurring as a side-effect of medicinal therapies.

Surprisingly, in contrast to the prior art compounds having similar structure, the compounds according to the invention do not act on $5\text{-HT}_{1A}$ receptors. They show a considerable binding to $5\text{-HT}_{2C}$ receptors, which is supposed to play a role in the pathomechanism of anxiety. The $\alpha_1$ receptoral effect of the compounds according to the invention suggests that they can be used for the treatment of cardiovascular diseases. Dopamine release evoking activity in the internal ear of guinea pig indicates that they are useful for the treatment of loss impairment and tinnitus.

Further details of the present invention are provided in the following examples without limiting the scope of protection to said examples.

EXAMPLE 1

5-Chloro-3-ethyl-1,3-dihydro-2H-indol-2-one

The title compound is prepared from 5-chloro-oxindole according to methods known from the literature [B. Volk, T. Mezei, Gy. Simig *Synthesis* 2002, 595]. 1.68 g (0.01 mole) of 5-chloro-oxindole is dissolved in 20 ml of ethanol and 1.0 g of Raney-nickel is added to the solution. The mixture is allowed to react in an autoclave at 110° C. for 36 hours. The catalyst is then filtered off, the solvent is evaporated, and the residue is recrystallized from a mixture of hexane and ethyl acetate.

Yield: 0.86 g of white powder (44%).

M.p.: 121-123° C. (hexane-ethyl acetate).

IR (KBr): 3156, 1701 (C=O), 782 cm$^{-1}$.

¹H-NMR (CDCl₃): 9.27 (br s, 1H, NH), 7.21 (1H, s, H-4), 7.19 (d, 1H, J=8.8 Hz, H-6), 6.85 (d, 1H, J=8.1 Hz, H-7), 3.47 (t, 1H, J=5.5 Hz, H-3), 2.03 (m, 2H, CH₂), 0.92 (t, 3H, J=7.0 Hz, CH₃) ppm.

¹³C-NMR (CDCl₃): 180.5, 140.4, 131.2, 127.8, 127.6, 124.5, 110.7, 47.5, 23.5, 9.9 ppm.

Analysis for the Formula C₁₀H₁₀ClNO (195.65):
Calculated: C, 61.39; H, 5.15; N, 7.16; Cl, 18.12%.
Found: C, 61.16; H, 5.10; N, 6.93; Cl, 18.11%.

EXAMPLE 2

5-Bromo-3-ethyl-1,3-dihydro-2H-indol-2-one

A 3-ethyl-oxindole (16.1 g; 0.10 mole) is dissolved in 350 ml of acetonitrile, the solution is cooled to 0° C., and a solution of N-bromo-succinimide (17.8 g; 0.10 mole) in 150 ml of acetonitrile is dropped to it at the same temperature within 2 hours. The reaction mixture is stirred first at 0° C. for 1 hour and then at room temperature for 3 hours. The solution is evaporated, the white substance separated in crystalline form is extracted with dichloro-methane and 1 M NaOH solution, and the organic phase is extracted again with alkaline water in order to remove succinimide. The organic phase is dried over sodium sulfate, filtered and evaporated. The separated white substance is recrystallized from a mixture of heptane and ethyl acetate.

Yield: 15.24 g of white powder (63%).
M.p.: 125-127° C. (heptane-ethyl acetate).
IR (KBr): 3154, 1700 (C=O), 812 cm⁻¹.

¹H-NMR (CDCl₃, TMS, 400 MHz): 8.90 (1H, s), 7.36-7.32 (2H, m), 6.81 (1H, d, J=8.9 Hz), 3.43 (1H, t, J=5.8 Hz), 2.03 (2H, q, J=7.4 Hz), 0.92 (3H, t, J=7.4 Hz) ppm.

¹³C-NMR (CDCl₃, TMS, 101 MHz): 180.3, 140.8, 131.6, 130.7, 127.2, 114.9, 111.2, 47.2, 23.4, 9.9 ppm.

Analysis for the Formula C₁₀H₁₀BrNO (240.10):
Calculated: C, 50.03; H, 4.20; N, 5.83; Br, 33.28%.
Found: C, 50.16; H, 4.20; N, 5.85; Br, 32.70%.

EXAMPLE 3

4-(4-Pyrimidin-2-yl-piperazin-1-yl)-but-2-in-1-ol dihydrochloride 2-(piperazin-1-yl)-pyrimidine (10.8 g; 66 mmoles) is measured to propargyl alcohol (3.9 ml; 66 mmoles), copper(II) acetate monohydrate (0.75 g; 3.8 mmoles) is added to it, and 37% aqueous formaline (20 ml, 265 mmoles) is pipetted to the reaction mixture under stirring. The green suspension is refluxed for 2 hours. Then it is cooled, water and chloroform are added to it and the pale green substance insoluble in both phases are filtered off. The aqueous phase is extracted twice with chloroform, the organic phases are combined, dried over sodium sulfate and evaporated. The residual brown oil is dissolved in ethyl acetate, and a solution of 2 molar equivalents of hydrogen chloride in isopropanol is dropped to it under stirring. The separated white salt is filtered off, stirred in hot isopropanol, cooled and filtered.

Yield: 12.7 g of white powder (63%).
M.p.: 187-188° C. (methanol).
IR (KBr): 3295, 1625 cm⁻¹.

¹H-NMR (DMSO-d₆, TMS, 400 MHz): 12.1 (br s, 1H), 8.54 (d, J=4.9 Hz, 2H), 7.12 (br s, 4H), 6.88 (t, J=4.9 Hz, 1H), 4.82 (br s, 2H), 4.23 (s, 2H), 4.17 (s, 2H), 3.62-3.48 (m, 4H), 3.20 (m, 2H) ppm.

¹³C-NMR (DMSO-d₆, TMS, 101 MHz): 159.1, 158.2, 111.5, 90.5, 73.1, 49.8, 49.2, 44.9, 40.9 ppm.

C₁₂H₁₈Cl₂N₄O (305.21).

EXAMPLE 4

4-[4-(2-Methoxyphenyl)-piperazin-1-yl]-but-2-in-1-ol dihydrochloride 1-(2-Methoxyphenyl)-piperazine (12.7 g; 66 mmoles) is measured to propargyl alcohol (3.9 ml; 66 mmoles), copper (II) acetate monohydrate (0.75 g; 3.8 mmoles) is added to it, and 37% aqueous formaline (20 ml, 265 mmoles) is pipetted to the reaction mixture under stirring. The green suspension is refluxed for 1.5 hour. Then it is cooled, water and chloroform are added to it and the pale yellow substance insoluble in both phases is filtered off. The aqueous phase is extracted twice with chloroform, the combined organic phases are dried over sodium sulfate and evaporated. The residual brown oil is dissolved in ethyl acetate, and a solution of 2 molar equivalents of hydrogen chloride in isopropanol is dropped to it under stirring. The separated white salt is filtered, digested while hot in isopropanol, cooled and filtered.

Yield: 16.3 g of white powder (74%).
M.p.: 179-181° C. (ethyl acetate-etanol).
IR (KBr): 3324, 2853 cm⁻¹.

¹H-NMR (D₂O, DSS, 400 MHz): 7.45 (m, 2H), 7.25 (dd, J=8.8, 1.2 Hz, 1H), 7.15 (dt, J=7.7, 1.2 Hz, 1H), 4.41 (t, J=1.7 Hz, 2H), 4.33 (t, J=1.7 Hz, 2H), 3.99 (s, 3H), 3.85 (br s, 8H) ppm.

¹³C-NMR (D₂O, DSS, 101 MHz): 154.3, 134.6, 124.1, 122.8, 115.5, 92.4, 75.0, 58.4, 52.1, 51.7, 48.8 ppm.

C₁₅H₂₂Cl₂N₂O₂ (333.26).

EXAMPLE 5

4-[4-(3-Chlorophenyl)-piperazin-1-yl]-but-2-in-1-ol dihydrochloride 1-(3-Chlorophenyl)-piperazine (19.7 g; 0.10 mole) is weighed to propargyl alcohol (11.8 ml; 0.20 mole), copper(II) acetate monohydrate (1.0 g; 5.2 mmoles) is added to it, and 37% aqueous formaline (50 ml) is pipetted to the reaction mixture under stirring. The green suspension is refluxed for 2 hours. Then it is cooled, water and chloroform are added to it and the pale green substance insoluble in both phases are filtered off. The aqueous phase is extracted twice with chloroform, the combined organic phases are dried over sodium sulfate and evaporated. The residual brown oil is dissolved in ethyl acetate, and a solution of 2 molar equivalents of hydrogen chloride in ethyl acetate is dropped to it under stirring. The separated white salt is filtered, digested while hot with isopropanol, cooled and filtered.

Yield: 26.6 g of white powder (79%).
M.p.: 171-173° C.

¹H-NMR (DMSO-d₆, TMS, 200 MHz): 8.6 (2H, br s), 7.28 (1H, t, J=8.0 Hz), 7.07 (1H, s), 6.95 (1H, d, J=2.0 Hz), 6.87 (1H, d, J=2.0 Hz), 4.23 (2H, s), 4.18 (2H, s), 3.95 (2H, br s), 3.55 (2H, br s), 3.22 (4H, br s) ppm.

C₁₄H₁₉Cl₃N₂O (337.68).

EXAMPLE 6

4-(4-Phenylpiperazin-1-yl)-but-2-in-1-ol dihydrochloride

1-Phenylpiperazine (16.2 g; 0.10 mole) is weighed to propargyl alcohol (11.8 ml; 0.20 mole), copper(II) acetate monohydrate (1.0 g; 5.2 mmoles) is added to it, and 37% aqueous formaline (50 ml) is pipetted to the reaction mixture under stirring. The green suspension is refluxed for 2 hours. Then it is cooled, water and chloroform are added to it and the pale green substance insoluble in both phases are filtered off. The aqueous phase is extracted twice with chloroform, the combined organic phases are dried over sodium sulfate and evaporated. The residual brown oil is dissolved in ethyl acetate, and a solution of 2 molar equivalents of hydrogen chloride in ethyl acetate is dropped to it under stirring. The separated white salt is filtered off, digested while hot with isopropanol, cooled and filtered.

Yield: 18.5 g of white powder (61%).
M.p.: 190-193° C.
$^1$H-NMR (DMSO-$d_6$, TMS, 200 MHz): 7.4 (2H, br s), 7.30 (2H, t, J=7.3 Hz), 7.15 (2H,t, J=8.3 Hz), 6.95 (1H, t, J=7.8 Hz), 4.24 (2H, s), 4.19 (2H, s), 3.83 (2H, br s), 3.58 (2H, br s), 3.28 (2H, br s) ppm.
$C_{14}H_{20}Cl_2N_2O$ (303.23).

EXAMPLE 7

2-[4-(4-Chlorobut-2-inyl)-piperazin-1-yl]-pyrimidine dihydrochloride

To thionyl chloride (30 ml; 0.41 mole) 4-(4-pyrimidin-2-yl-piperazin-1-yl)-but-2-in-1-ol dihydrochloride (9.61 g; 31.5 mmoles) is added in small portions with a spatula, under stirring. When the addition has been completed, the reaction mixture is warmed to reflux temperature. A vigorous gas formation can be observed, the starting substance dissolves and the product separates in form of salt. 15 ml of toluene are added to the reaction mixture, and it is stirred until the gas formation has been ceased (about half an hour). The mixture is then cooled, the snow-white powder is filtered, washed with ethyl acetate and dried.

Yield: 8.77 g of white powder (86%).
M.p.: 178-179° C. (ethanol).
IR (KBr): 1622 cm$^{-1}$.
$^1$H-NMR (DMSO-$d_6$, TMS, 400 MHz): 12.4 (s, 1H), 8.49 (d, J=4.9 Hz, 2H), 6.82 (t, J=4.8 Hz, 6.7 (br s, 1H), 4.79 (s, 2H), 4.59 (s, 2H), 4.31 (s, 2H), 3.56 (m. 4H), 3.15 (m, 2H) ppm.
$^{13}$C-NMR (DMSO-$d_6$, TMS, 101 MHz): 160.1, 158.3, 111.5, 85.5, 75.7, 49.9, 44.6, 40.5, 30.7 ppm.
$C_{12}H_{17}Cl_3N_4$ (323.65).

EXAMPLE 8

1-(4-Chlorobut-2-inyl)-4-(2-methoxyphenyl)-piperazine dihydrochloride

To thionyl chloride (40 ml; 0.55 mole) 4-[4-(2-methoxyphenyl)-piperazin-1-yl]-but-2-in-1-ol dihydrochloride (13.3 g; 40 mmoles) is added in small portions with a spatula, under stirring. When the addition has been completed, the reaction mixture is warmed to reflux temperature. A vigorous gas formation can be observed, the starting substance dissolves and the product separates in form of salt. 30 ml of toluene is added to the reaction mixture, and it is stirred until the gas formation has been ceased. The mixture is then cooled, the white powder is filtered, washed with ethyl acetate and dried.

Yield: 12.52 g of white powder (89%).
M.p.: 174-175° C. (CH$_3$CN).
IR (KBr): 2400, 2200 cm$^{-1}$.
$^1$H-NMR (D$_2$O, DSS, 200 MHz): 7.51-7.43 (m, 2H), 7.24 (d, J=8.1 Hz, 1H), 7.16 (t, J=8.1 Hz, 1H), 4.41 (s, 2H), 4.35 (s, 2H), 3.99 (s, 3H), 3.87 (br s, 8H) ppm.
$^{13}$C-NMR (D$_2$O, DSS, 50 MHz): 154.3, 134.2, 132.2, 124.2, 122.9, 115.6, 89.6, 75.7, 58.5, 52.1, 48.7, 32.3 ppm.
$C_{15}H_{21}Cl_3N_2O$ (351.70).

EXAMPLE 9

1-(2,6-Dichlorophenyl)-3-isopropylidene-1,3-dihydro-2H-indol-2-one 1-(2,6-Dichlorophenyl)-oxindole (27.8 g; 0.10 mole) is dissolved in 300 ml of acetone, pyrrolidine (10 ml; 0.12 mole) is measured to the solution and it is warmed to reflux temperature. The reaction mixture is refluxed for 3 hours and the solution is evaporated. The product separated in crystalline form is dissolved in dichloro-methane, extracted twice with 10% hydrogen chloride, the organic phase is dried over sodium sulfate, clarified with bone coal, filtered and evaporated. The product is used for the catalytic hydrogenation without recrystallization. Analytical samples may be obtained by recrystal-lization from ethyl acetate.

Yield: 31.82 g of yellow crystal (97%).
M.p.: 180-182° C. (ethyl acetate).
IR (KBr): 1700 (C=O), 793 cm$^{-1}$.
$^1$H-NMR (CDCl$_3$, TMS, 400 MHz): 2.46 (3H, s), 2.66 (3H, s), 6.40 (1H, dd, J=0.6, 7.8 Hz), 7.09 (1H, dt, J=1.2, 7.6 Hz), 7.17 (1H, dt, J=1.0, 7.6 Hz), 7.35 (1H, dd, J=7.6, 8.7 Hz), 7.50 (2H, d, J=8.2 Hz), 7.64 (1H, d, J=7.5 Hz) ppm.
$^{13}$C-NMR (CDCl$_3$, TMS, 101 MHz): 23.4, 25.4, 108.5, 122.0, 122.3, 123.7, 123.8, 127.6, 128.9, 130.4, 130.9, 135.9, 140.0, 156.1, 166.2 ppm.
Analysis for the Formula $C_{17}H_{13}Cl_2NO$ (318.21):
Calculated: C, 64.17; H, 4.12; Cl, 22.28; N, 4.40%.
Found: C, 64.02; H, 4.11; Cl, 22.14; N, 4.39%.

EXAMPLE 10

1-(2,6-Dichlorophenyl)-3-isopropyl-1,3-dihydro-2H-indol-2-one 1-(2,6-Dichlorophenyl)-3-isopropylidene oxindole (23.7 g; 75 mmoles) is dissolved in 170 ml of methanol, 5% palladium on bone coal (2.0 g) is added to it and the reaction mixture is stirred in an autoclave for 3 hours at room temperature under a starting hydrogen pressure of 15 bar. Then it is clarified with bone coal, filtered and evaporated. The residual yellow oil gets crystal-line upon trituration with hexane. The product is stirred in hexane, filtered, dried and used without further purification.

Yield: 19.6 g of off-white powder (82%).
M.p.: 138-140° C. (ethyl acetate).
IR (KBr): 1720 (C=O), 752 cm$^{-1}$.
$^1$H-NMR (CDCl$_3$, TMS, 400 MHz): 7.49 (d, J=8.5 Hz, 2H), 7.37 (d, J=7.3 Hz, 1H), 7.35 (t, J=8.2 Hz, 1H), 7.19 (t, J=7.7 Hz, 1H), 7.09 (dt, J=0.9, 7.5 Hz, 1H), 6.38 (d, J=7.8 Hz, 1H), 3.64 (d, J=3.5 Hz, 1H), 2.63 (m, 1H), 1.20 (d, J=7.0 Hz, 3H), 1.07 (d, J=7.0 Hz, 3H) ppm.

$^{13}$C-NMR (CDCl$_3$, TMS, 101 MHz): 175.8, 142.8, 135.5, 135.4, 130.6, 130.5, 129.0, 128.9, 127.7, 127.6, 122.7, 121.7, 108.8, 51.7, 31.0, 20.1, 18.7 ppm.

C$_{17}$H$_{15}$Cl$_2$NO (320.22).

EXAMPLE 11

1-(2,6-Dichlorophenyl)-3-isopropyl-3-[4-(4-pyrimidin-2-yl-piperazin-1-yl)-but-2-inyl]-1,3-dihydro-2H-indol-2-one monohydrochloride Sodium hydride (2.7 g; 55% suspension; 62 mmoles) is washed three times with 10 ml each of hexane in order to remove the suspended oil, and suspended in 100 ml of DMF at room temperature. 1-(2,6-Dichlorophenyl)-3-isopropyl-oxindole (5.0 g; 15.6 mmoles) is added to it in small portions. When the gas formation has been ceased 2-[4-(4-chlorobut-2-inyl)-piperazin-1-yl]-pyrimidine di-hydrochloride (4.88 g; 15.1 mmoles) is added to it in small portions. The mixture is allowed to react for 1 hours. Then 2 ml of water is added to it in order to decompose excess of sodium hydride. The mixture is extracted with water and diethyl ether, and the aqueous phase is extracted again with ether. The combined organic phases are dried over sodium sulfate and evaporated. The thus-obtained yellowish brown oil is purified by column chromatography using ethyl acetate as eluent. The pure substance is dissolved in 100 ml of diethyl ether and a solution of 1 molar equivalent of hydrogen chloride in isopropanol is dropped to the solution under stirring. The separated hydrochloride salt is filtered, washed with a small amount of IPA and hexane and dried in a vacuum pistol.

Yield: 3.02 g of white powder (37%).

M.p.: 171-173° C.

IR (KBr): 2364, 1722 (C=O) cm$^{-1}$.

$^1$H-NMR (CDCl$_3$, TMS, 400 MHz): 13.3 (1H, s), 8.35 (2H, d, J=4.7 Hz), 7.54-7.49 (2H, m), 7.40 (1H, t, J=7.6 Hz), 7.28 (1H, d, J=6.8 Hz), 7.11 (1H, dt, J=1.2, 7.6 Hz), 6.91 (1H, dt, J=0.9, 7.6 Hz), 6.62 (1H, t, J=4.8 Hz), 6.40 (1H, d, J=7.8 Hz), 4.85, 4.76 (2×1H, d, J=14.4 Hz), 3.83, 3.68 (2×1H, d, 17.1 Hz), 3.62. 3.59 (2×1H, d, J=11.7 Hz), 3.14, 3.01 (2×1H d, J=11.0 Hz), 2.97, 2.91 (2×1H d, J=17.1 Hz), 2.88 (1H, m), 2.46 (1H, m), 2.30 (1H, q, J=6.9 Hz), 1.03 (3H, d, J=6.9 Hz), 0.98 (3H, d, J=6.9 Hz) ppm.

$^{13}$C-NMR (CDCl$_3$, TMS, 101 MHz): 176.4, 157.7, 150.8, 142.2, 135.1, 135.0, 130.8, 130.1, 129.9, 129.3, 129.2, 128.3, 124.0, 123.0, 111.2, 109.1, 88.8, 69.2, 54.8, 49.5, 46.4, 40.3, 34.9, 25.7, 17.4 ppm.

Analysis for the Formula C$_{29}$H$_{30}$Cl$_3$N$_5$O (570.95):
Calculated: C, 61.01; H, 5.30; Cl, 18.63; N, 12.27%.
Found: C, 59.81; H, 5.28; Cl, 18.41; N, 11.90%.

EXAMPLE 12

(E)-1-(2,6-Dichlorophenyl)-3-(4-methyl-benzylidene)-1,3-dihydro-2H-indol-2-one 1-(2,6-Dichlorophenyl)-oxindole (22.24 g; 80 mmoles) and 4-methyl benzaldehyde (10.0 g; 84 mmoles) are dissolved in 250 ml of toluene, pyrrolidine (4.0 ml; 0.30 mole) is measured to the solution, and the mixture is warmed to reflux temperature. It is refluxed for 1 hour, allowed to cool, extracted twice with 10% hydrogen chloride, the toluene phase is dried over sodium sulfate, clarified with bone coal, filtered, washed on the filter with toluene and evaporated. The residual orange-red oil gets crystalline upon trituration with hexane. The substance is stirred in hexane, filtered and washed with hexane. The product is used for the catalytic hydrogenation without recrystallization.

Yield: 18.59 g of yellow crystal (61%).

M.p.: 201-202° C. (ethyl acetate).

IR (KBr): 1716 (C=O), 791 cm$^{-1}$.

$^1$H-NMR (CDCl$_3$, TMS, 400 MHz): 2.44 (3H, s), 6.41 (1H, d, J=7.9 Hz), 6.95 (1H, t, J=7.7 Hz), 7.18 (1H, t, J=7.7 Hz), 7.30 (2H, d, J=8.0 Hz), 7.37 (1H, t, J=7.7 Hz), 7.51 (1H, d, J=7.9 Hz), 7.64 (2H, d, J=8.0 Hz), 7.81 (1H, d, J=7.7 Hz), 7.96 (1H, s) ppm.

$^{13}$C-NMR (CDCl$_3$, TMS, 101 MHz): 21.6, 109.2, 121.4, 122.4, 123.0, 125.5, 128.9, 129.3, 129.5, 129.6, 130.5, 130.6, 131.8, 135.7, 138.8, 140.2, 142.1, 167.2 ppm.

Analysis for the Formula C$_{22}$H$_{15}$Cl$_2$NO (380.28):
Calculated: C, 69.49; H, 3.98; Cl, 18.65; N, 3.68%.
Found: C, 69.53; H, 4.03; Cl, 18.49; N, 3.67%.

EXAMPLE 13

1-(2,6-Dichlorophenyl)-3-(4-methylbenzyl)-1,3-dihydro-2H-indol-2-one 1-(2,6-Dichlorophenyl)-3-(4-methyl-benzylidene)-oxindole (12.0 g; 31.6 mmoles) is dissolved in 170 ml of ethanol and saturated in an autoclave using 5% palladium on bone coal catalyst (2.0 g) under a hydrogen pressure of 10 bar. The reaction takes 2 hours. The catalyst is then filtered off, the mixture is clarified with bone coal and evaporated. The product gets crystalline in form of an off-white powder.

Yield: 10.21 g of off-white powder (84%).

M.p.: 123-124° C. (hexane-ethyl acetate).

IR (KBr): 1718 (C=O), 753 cm$^{-1}$.

$^1$H-NMR (CDCl$_3$, TMS, 400 MHz): 7.47 (dd, J=1.4, 8.0 Hz, 1H), 7.45 (dd, J=1.4, 8.2 Hz, 1H), 7.33 (t, J=8.1 Hz, 1H), 7.14 (t, J=7.6 Hz, 1H), 7.11 (d, J=8.0 Hz, 2H), 7.07 (d, J=8.0 Hz, 2H), 6.97 (dt, J=0.9, 7.5 Hz, 1H), 6.89 (d, J=7.4 Hz, 1H), 6.33 (d, J=7.8 Hz, 1H), 3.96 (dd, J=4.5, 9.2 Hz, 1H), 3.57 (dd, J=4.5, 13.7 Hz, 1H), 3.03 (dd, J=9.2, 13.7 Hz, 1H), 2.31 (s, 3H) ppm.

$^{13}$C-NMR (CDCl$_3$, TMS, 101 MHz): 175.5, 142.4, 136.2, 135.5, 135.4, 134.5, 130.6, 130.1, 129.5, 129.0, 128.9, 128.8, 127.9, 126.2, 125.0, 122.6, 108.9, 47.2, 36.5, 21.0 ppm.

C$_{22}$H$_{17}$Cl$_2$NO (382.29).

EXAMPLE 14

1-(2,6-Dichlorophenyl)-3-{4-[4-(2-methoxyphenyl)-piperazin-1-yl]-but-2-inyl}-3-(4-methylbenzyl)-1,3-dihydro-2H-indol-2-one dioxalate Sodium hydride (2.0 g; 55% suspension; 46 mmoles) is washed three times with 10 ml each of hexane in order to remove the suspended oil, and suspended in 50 ml of DMF at room temperature.

1-(2,6-Dichlorophenyl)-3-(4-methylbenzyl)-oxindole (5.0 g; 13 mmoles) is added to it in small portions, and when the formation of hydrogen gas has been ceased 1-(4-chlorobut-2-inyl)-4-(2-methoxyphenyl)-piperazine dihydrochloride (4.61 g; 13 mmoles) is added in small portions. After 1 hour 2 ml of water are added to the reaction mixture in order to decompose excess of sodium hydride. The mixture is extracted with water and ethyl acetate, the organic phase is acidified with 10% by volume of hydrogen chloride solution, and the acidic-aqueous phase is made alkaline again with 25% by volume of ammonia solution and extracted with ethyl acetate. The organic phase is dried over sodium sulfate and evaporated. The residual yellowish brown oil (7.0 g; 11.2 mmoles) is dissolved in 70 ml of hot ethyl acetate, and a solution of oxalic acid dihydrate (2.82 g; 22.4 mmoles) in 30 ml of hot ethyl acetate is dropped to it. Upon cooling the reaction mixture the dioxalate salt gets separated It is filtered off and washed with ethyl acetate and hexane.

Yield: 7.88 g of white powder (75%).

M.p.: 167-170° C.

IR (KBr): 1712 (C=O), 753 cm$^{-1}$.

$^1$H-NMR (CD$_3$OD, TMS, 400 MHz): 7.60 (1H, m), 7.58 (1H, dd, J=2.2, 7.3 Hz), 7.48-7.41 (1H, m), 7.47 (1H, t, J=8.2 Hz), 7.21-7.13 (2H, m), 7.06 (1H, dt, J=0.9, 1.8 Hz), 6.98-6.89 (3H, m), 6.86 (2H, d, J=7.9 Hz), 6.81 (2H, d, J=8.1 Hz,), 6.26 (1H, dd, J=1.2, 8.3 Hz), 4.09, 3.94 (2×1H, d, J=16.0 Hz), 3.82 (3H, s), 3.38, 3.22 (2×1H, d, J=13.3 Hz), 3.09, 2.99 (2×1H, d, J=16.8 Hz), 3.4-3.0 (8H, br s), 2.18 (3H, s) ppm.

$^{13}$C-NMR (CD$_3$OD, TMS, 101 MHz): 178.5, 164.3, 154.0, 143.4, 140.5, 137.7, 133.0, 132.7, 131.7, 131.5, 131.1, 130.8, 130.4, 130.3, 130.3, 129.8, 129.0, 126.2, 125.6, 124.7, 122.3, 120.8, 120.1, 113.1, 110.0, 88.5, 72.6, 56.2, 54.0, 52.5, 48.9, 47.3, 42.8, 28.8, 21.2 ppm.

Analysis for the Formula C$_{41}$H$_{39}$Cl$_2$N$_3$O$_{10}$ (804.69):

Calculated: C, 61.20; H, 4.89; Cl, 8.81; N, 5.22%.

Found: C, 61.12; H, 5.00; Cl, 8.73; N, 5.25%.

EXAMPLE 15

3-Ethyl-3-(prop-2-inyl)-1,3-dihydro-2H-indol-2-one

Into a flask rinsed with argon 2.5 M n-butyl lithium (60 ml; 0.15 mole) is measured. 40 ml of THF are added to it, and the solution is cooled in an acetone-dry ice bath to −78° C. At this temperature a solution of 3-ethyl oxindole (9.66 g; 0.06 mole) in 50 ml of THF is dropped to it under stirring, stirred for further 10 minutes, propargyl bromide (4.7 ml; 0.063 mole) is dropped to it, and the solution is allowed to warm up to room temperature. Then it is stirred further for 3 hours, 20 ml of ethanol is dropped to it in order to decompose excess of butyl lithium. The solution is distilled with a rotary evaporator, and the residual oil is extracted with water and ethyl acetate. The organic phase is dried over sodium sulfate. The residual oil is made crystalline by triturating it with hexane. The separated off-white crystals are stirred in 50 ml of hexane in order to remove excess of propargyl bromide, filtered and washed with hexane. The product is used for the further reactions without recrystallization.

Yield: 10.87 g of white powder (91%).

M.p.: 108-110° C. (hexane-ethyl acetate).

IR (KBr): 3308, 3150, 1719 cm$^{-1}$.

$^1$H-NMR (CDCl$_3$, TMS, 200 MHz): 9.19 (br s, 1H, NH), 7.36 (dt, 1H, J=7.3, 0.7 Hz, H-4), 7.24 (dt, 1H, J=7.7, 1.5 Hz, H-6), 7.07 (dt, 1H, J=7.7, 1.1 Hz, H-5), 6.96 (d, 1H, J=7.7 Hz, H-7), 2.65 (dq, 2H, J=16.5, 2.6 Hz, CH$_2$CCH), 2.10-1.88 (m, 2H, CH$_2$CH$_3$), 1.94 (t, 1H, J=2.6 Hz, CH), 0.67 (t, 3H, J=7.3 Hz, CH$_3$) ppm.

$^{13}$C-NMR (CDCl$_3$, TMS, 50 MHz): 181.4, 141.2, 131.4, 128.1, 123.6, 122.4, 109.8, 79.5, 70.7, 52.3, 29.1, 27.0, 8.6 ppm.

Analysis for the Formula C$_{13}$H$_{13}$NO (199.25):

Calculated: C, 78.36; H, 6.58; N, 7.03%.

Found: C, 78.29; H, 6.55; N, 6.99%.

EXAMPLE 16

3-Ethyl-1-methyl-3-(prop-2-inyl)-1,3-dihydro-2H-indol-2-one

Sodium hydride (3.71 g; 55% suspension; 85 mmoles) is washed three times with 10 ml each of hexane and suspended in 70 ml of DMF. The reaction mixture is cooled to 0-2° C., and at this temperature a solution of 3-ethyl-3-(prop-2-inyl)-oxindole (15.0 g; 75 mmoles) in 60 ml of DMF is dropped to it. When the formation of hydrogen has been ceased methyl iodide (5.3 ml; 85 mmoles) is dropped to the reaction mixture, it is stirred for 3 hours, 5 ml of water is dropped to it in order to decompose excess of sodium hydride and extracted with water and diethyl ether. The organic phase is dried over sodium sulfate, clarified with bone coal, filtered and evaporated. The residual pale yellow oil gets crystalline upon trituration with hexane.

Yield: 12.21 g of yellowish white powder (76%).

M.p.: 79-81° C. (hexane-ethyl acetate).

IR (KBr): 2970, 2930, 1710 (C=O) cm$^{-1}$.

$^1$H-NMR (CDCl$_3$, TMS, 200 MHz): 7.39 (d, J=7.3 Hz, 1H), 7.30 (dt, J=1.1, 7.7, 1H), 7.09 (dt, J=1.1, 7.6 Hz, 1H), 3.22 (s, 3H), 2.71, 2.51 (dd, J=2.5, 16.5 Hz, 2H), 2.00 (q, J=7.3 Hz, 2H), 1.92 (t, J=2.8 Hz, 1H), 0.59 (t, J=7.5 Hz, 3H) ppm.

$^{13}$C-NMR (CDCl$_3$, TMS, 50 MHz): 178.5, 143.8, 130.9, 128.1, 123.2, 122.4, 107.7, 79.5, 70.4, 51.5, 29.0, 26.9, 26.0, 8.5 ppm.

Analysis for the Formula C$_{14}$H$_{15}$NO (213.28): Calculated: C, 78.84; H, 7.09; N, 6.57%.

Found: C, 78.44; H, 7.08; N, 6.52%.

EXAMPLE 17

1-Benzyl-3-ethyl-3-(prop-2-inyl)-1,3-dihydro-2H-indol-2-one

Sodium hydride (3.71 g; 55% suspension; 85 mmoles) is washed three times with 10 ml each of hexane and suspended in 70 ml of DMF. The reaction mixture is cooled to 0-2° C., and at this temperature a solution of 3-ethyl-3-(prop-2-inyl)-oxindole (15.0 g; 75 mmoles) in 60 ml of DMF is dropped to it. When the formation of hydrogen gas has been ceased benzyl chloride (9.5 ml; 75 mmoles) is dropped to the mixture. It is stirred for 2 hours, 5 ml of water are dropped to it in order to decompose excess of sodium hydride and extracted with water and diethyl ether. The organic phase is dried over sodium sulfate, clarified with bone coal, filtered and evaporated. The residual pale yellow oil gets crystalline upon trituration with hexane.

Yield: 18.71 g of off-white powder (86%).

M.p.: 79-80° C. (hexane-ethyl acetate).

IR (KBr): 1703 (C=O) cm$^{-1}$.

$^1$H-NMR (CDCl$_3$, TMS, 400 MHz): 7.38-7.20 (m, 6H), 7.17 (dt, J=1.2, 7.7 Hz, 1H), 7.05 (dt, J=1.0, 7.6 Hz, 1H), 6.73 (d, J=7.8 Hz, 1H), 4.96, 4.90 (d, J=15.7 Hz, 2H), 2.75, 2.62 (dd, J=2.7, 16.5 Hz, 2H), 2.02 (q, J=7.4 Hz, 2H), 1.87 (t, J=2.7 Hz, 1H), 0.64 (t, J=7.4 Hz, 3H) ppm.

$^{13}$C-NMR (CDCl$_3$, TMS, 101 MHz): 178.6, 143.1, 135.9, 130.9, 128.6, 128.0, 127.5, 127.3, 123.3, 122.5, 108.9, 79.6, 70.6, 51.7, 43.7, 29.4, 27.2, 8.7 ppm.

Analysis for the Formula C$_{20}$H$_{19}$NO (289.38):

Calculated: C, 83.01; H, 6.62; N, 4.84%.

Found: C, 82.91; H, 6.67; N, 4.80%.

Process A (Mannich Reaction of Acetylene Hydrogen with piperazines)

To a mixture of an appropriate N-substituted 3-propargyl oxindole (50 mmoles), an appropriate piperazine (50 mmoles), 1.0 g of copper(II) acetate monohydrate and 100 ml of ethanol 35% aqueous formaline solution (50 ml; 0.63 mole) is dropped, and the solution is refluxed for 2 hours. It is filtered on a G4 glass filter in order to remove polymeric formaldehyde, evaporated and extracted with water and ethyl acetate. The organic phase is clarified with bone coal, dried over sodium sulfate and evaporated. The residual pale yellow oil is purified by column chromatography using ethyl acetate as eluent.

Purification method 1: The basic product is dissolved in 200 ml of ether, the small amount of floating precipitate is filtered off, and to the pure solution the calculated amount (1 or 2 molar equivalent(s)) of a solution of hydrogen chloride in ether diluted with 50 ml of diethyl ether is dropped at room temperature within half an hour, under vigorous stirring. The separated white salt is filtered off, washed with ether and hexane and dried in a vacuum pistol at room temperature for 3 hours. If necessary, the hydrochloride salt is recrystallized.

Purification method 2: If the basic product does not get crystalline upon the addition of diethyl ether and does not provide a well-filterable salt with hydrogen chloride, it is dissolved in 200 ml of hot ethyl acetate, and a solution of 1 molar equivalent of oxalic acid dihydrate in 50 ml of hot ethyl acetate is dropped to it within 10 minutes, under stirring. The white oxalate salt separates upon cooling. It is filtered off at room temperature, washed with ethyl acetate and hexane and dried.

EXAMPLE 18

3-Ethyl-3-{4-[4-(2-methoxyphenyl)-piperazin-1-yl]-but-2-inyl}-1-methyl-1,3-dihydro-2H-indol-2-one dihydrochloride The title compound is prepared according to process A by applying purification method 1 starting from 3-ethyl-1-methyl-3-(prop-2-inyl)-1,3-dihydro-2H-indol-2-one and 1-(2-methoxyphenyl)-piperazine.

M.p.: 189-192° C.

IR (KBr): 2840, 1710 (C=O) cm$^{-1}$.

$^1$H-NMR (CDCl$_3$, TMS, 400 MHz): kb. 13.7 (1H, br s), 8.17 (1H, d, J=7.6 Hz), 7.46 (1H, dt, J=1.5, 7.9 Hz), 7.37 (1H, dd, J=0.6, 7.3 Hz), 7.25 (1H, dd, J=1.1, 7.7 Hz), 7.11-7.03 (3H, m), 6.91 (1H, d, J=7.8 Hz), 4.8 (2H, m), 4.10 (1H, m), 4.06 (3H, s), 4.01 (1H, m), 3.85 (2H, m), 3.50 (2H, m), 3.36 (1H, d, J=12.5 Hz), 3.29 (3H, s), 3.21 (1H d, J=12.5 Hz), 2.85, 2.78 (2H, d, J=16.8 Hz), 2.05-1.83 (2H, m), 0.60 (3H, t, J=7.3 Hz) ppm.

$^{13}$C-NMR (CDCl$_3$, TMS, 101 MHz): 178.0, 152.4, 144.2, 131.4, 130.6, 128.6, 128.0, 123.7, 123.4, 122.4, 121.6, 113.3, 108.0, 68.2, 55.9, 52.1, 48.5, 47.3, 47.1, 46.0, 29.6, 27.1, 26.2, 8.5 ppm.

Analysis for the Formula C$_{26}$H$_{33}$Cl$_2$N$_3$O$_2$ (490.48):
Calculated: C, 63.67; H, 6.78; Cl, 14.46; N, 8.57%.
Found: C, 62.99; H, 6.84; Cl, 13.84; N, 8.65%.

EXAMPLE 19

3-Ethyl-1-methyl-3-[4-(4-pyrimidin-2-yl-piperazin-1-yl)-but-2-inyl]-1,3-dihydro-2H-indol-2-one monooxalate The title compound is prepared according to process A by applying purification method 2 starting from 3-ethyl-1-methyl-3-(prop-2-inyl)-1,3-dihydro-2H-indol-2-one and 2-(piperazin-1-yl)-pyrimidine.

M.p.: 119-121° C.

IR (KBr): 3452, 1702 (C=O) cm$^{-1}$.

$^1$H-NMR (DMSO-d$_6$, TMS, 400 MHz): 8.5 (2H, br s), 8.44 (2H, d, J=4.8 Hz), 7.35 (1H, dd, J=1.8, 7.3 Hz), 7.13 (1H, dt, J=1.3, 7.7 Hz), 7.00 (1H, dt, J=0.9, 7.5 Hz), 6.74 (1H, d, J=7.8 Hz), 3.70 (4H, s), 3.48, 3.36 (1+1H, d, J=16.6 Hz), 3.07 (3H, s), 2.79, 2.60 (+1H, d, J=16.3 Hz), 2.34-2.27 (4H, m), 1.81-1.72 (2H, m), 0.46 (3H, t, J=7.4 Hz) ppm.

$^{13}$C-NMR (DMSO-d$_6$, TMS, 101 MHz): 177.9, 162.5, 161.1, 158.2, 144.2, 130.8, 128.0, 123.2, 122.3, 110.6, 108.1, 82.9, 74.2, 52.3, 50.0, 45.8, 42.1, 29.4, 26.5, 25.9, 8.7 ppm.

Analysis for the Formula C$_{25}$H$_{29}$N$_5$O$_5$ (479.54):
Calculated: C, 62.62; H, 6.10; N, 14.60%.
Found: C, 62.62; H, 6.08; N, 14.30%.

EXAMPLE 20

3-{4-[4-(4-Chlorophenyl)-piperazin-1-yl]-but-2-inyl}-3-ethyl-1-methyl-1,3-dihydro-2H-indol-2-one monooxalate The title compound is prepared according to process A by applying purification method 2 starting from 3-ethyl-1-methyl-3-(prop-2-inyl)-1,3-dihydro-2H-indol-2-one and 1-(4-chlorophenyl)-piperazine.

M.p.: 69-72° C.

IR (KBr): 3453, 1710 (C=O) cm$^{-1}$.

$^1$H-NMR (CDCl$_3$, TMS, 400 MHz): 8.78 (3H, br s), 7.26-7.21 (4H, m), 7.08 (1H, dt, J=0.8, 7.5 Hz), 6.83-6.78 (3H, m), 3.7 (2H, br s), 3.26 (4H, br s), 3.20 (3H, s), 2.87 (4H, br s), 2.78 (1H, d, J=16.7 Hz), 2.71 (1H, d, J=16.7 Hz), 1.96-1.79 (2H, m), 0.58 (3H, t, J=7.3 Hz) ppm.

$^{13}$C-NMR (CDCl$_3$, TMS, 101 MHz): 178.2, 164.0, 148.3, 143.9, 130.6, 129.1, 128.1, 125.9, 122.9, 122.7, 117.7, 107.9, 86.5, 70.0, 52.4, 49.6, 46.7, 45.7, 30.0, 26.9, 26.1, 8.5 ppm.

Analysis for the Formula C$_{27}$H$_{30}$ClN$_3$O$_5$ (512.01):
Calculated: C, 63.34; H, 5.91; Cl, 6.92; N, 8.21%.
Found: C, 63.43; H, 5.97; Cl, 6.99; N, 8.20%.

EXAMPLE 21

3-Ethyl-1-methyl-3-[4-(4-phenylpiperazin-1-yl)-but-2-inyl]-1,3-dihydro-2H-indol-2-one monooxalate The title compound is prepared according to process A by applying purification method 2 starting from 3-ethyl-1-methyl-3-(prop-2-inyl)-1,3-dihydro-2H-indol-2-one and 1-phenylpiperazine.

M.p.: 73-76° C.

IR (KBr): 3453, 1710 (C=O) cm$^{-1}$.

$^1$H-NMR (CDCl$_3$, TMS, 400 MHz): 9.71 (3H, br s), 7.32-7.22 (4H, m), 7.08 (1H, dt, J=0.8, 7.5 Hz), 6.94 (1H, t, J=7.3 Hz), 6.89 (2H, d, J=7.9 Hz), 6.81 (1H, d, J=7.7 Hz), 3.77 (2H, s), 3.31 (4H, br s), 3.20 (3H, s), 2.95 (4H, br s), 2.79 (1H, d, J=16.6 Hz), 2.71 (1H, d, J=16.6 Hz), 2.04-1.77 (2H, m), 0.58 (3H, t, J=7.4 Hz) ppm.

$^{13}$C-NMR (CDCl$_3$, TMS, 101 MHz): 178.1, 163.5, 149.4, 143.9, 130.5, 129.2, 128.1, 122.9, 122.7, 121.1, 116.6, 108.0, 87.2, 69.2, 52.3, 49.7, 46.4, 45.6, 29.9, 26.8, 26.0, 8.4 ppm.
Analysis for the Formula C$_{27}$H$_{31}$N$_3$O$_5$ (477.57):
Calculated: C, 67.91; H, 6.54; N, 8.80%.
Found: C, 67.20; H, 6.60; N, 8.73%.

EXAMPLE 22

1-Benzyl-3-ethyl-3-{4-[4-(2-methoxyphenyl)-piperazin-1-yl]-but-2-inyl}-1,3-dihydro-2H-indol-2-one monohydrochloride The title compound is prepared according to process A by applying purification method 1 starting from 3-ethyl-1-benzyl-3-(prop-2-inyl)-1,3-dihydro-2H-indol-2-one and 1-(2-methoxy-phenyl)-piperazine.
M.p.: 199-202° C.
IR (KBr): 2337, 1713 (C=O) cm$^{-1}$.
$^1$H-NMR (CDCl$_3$, TMS, 400 MHz): 7.4-7.2 (5H, m), 7.25 (1H, dd, J=1.0, 7.3 Hz), 7.14 (1H, dt, J=1.3, 7.7 Hz), 7.10-7.04 (2H, m), 6.97-6.88 (3H, m), 6.81 (1H, d, J=7.7 Hz), 5.02, 4.92 (2H, d, J=15.4 Hz), 3.87 (3H, s), 3.64, 3.45 (2H, d, J=16.8 Hz), 3.35 (4H, br s), 2.88, 2.77 (2H, d, J=16.6 Hz), 3.00-2.60 (4H, s), 2.02, 1.91 (2H, m), 0.66 (3H, t, J=7.3 Hz) ppm.
$^{13}$C-NMR (CDCl$_3$, TMS, 101 MHz): 178.2, 151.8, 143.2, 138.7, 135.9, 130.5, 128.7, 128.2, 127.9, 127.7, 124.2, 123.1, 122.7, 121.2, 118.8, 111.3, 108.9, 88.0, 68.8, 55.2, 52.3, 50.0, 47.0, 45.8, 43.7, 29.9, 27.6, 8.8 ppm.
Analysis for the Formula C$_{32}$H$_{36}$ClN$_3$O$_2$ (530.12):
Calculated: C, 72.50; H, 6.85; Cl, 6.69; N, 7.93%.
Found: C, 72.16; H, 6.83; Cl, 6.50; N, 7.89%.

EXAMPLE 23

1-Benzyl-3-ethyl-3-[4-(4-pyrimidin-2-yl-piperazin-1-yl)-but-2-inyl]-1,3-dihydro-2H-indol-2-one monooxalate The title compound is prepared according to process A by applying purification method 2 starting from 3-ethyl-1-benzyl-3-(prop-2-inyl)-1,3-dihydro-2H-indol-2-one and 2-(piperazin-1-yl)-pyrimidine.
M.p.: 154-155° C.
IR (KBr): 1716 (C=O) cm$^{-1}$.
$^1$H-NMR (CDCl$_3$, TMS, 400 MHz): 10.83 (2H, br s), 8.39 (2H, d, J=4.8 Hz), 7.40-7.25 (5H, m), 7.15 (1H, d, J=7.3 Hz), 7.02 (1H, dt, J=1.1, 7.7 Hz), 6.87 (1H, t, J=7.2 Hz), 6.70 (1H, d, J=7.8 Hz), 6.64 (1H, t, J=4.8 Hz), 4.95 (1H, d, J=15.3 Hz), 4.77 (1H, d, J=15.3 Hz), 3.90 (4H, s), 3.71 (1H, d, J=16.8 Hz), 3.41 (1H, dt, J=16.8, 2.2 Hz), 2.88 (1H, d, J=16.6 Hz), 2.72 (1H, dt, J=16.6, 2.3 Hz,), 2.50 (4H, br s), 1.96 (1H, m), 1.82 (1H, m), 0.63 (3H, t, J=7.3 Hz) ppm.
$^{13}$C-NMR (CDCl$_3$, TMS, 101 MHz): 178.2, 163.1, 160.8, 157.8, 143.1, 136.0, 130.5, 128.8, 128.3, 128.0, 127.9, 122.9, 122.7, 111.3, 108.7, 87.5, 69.1, 52.4, 49.6, 45.7, 43.8, 40.2, 30.2, 27.2, 8.7 ppm.
Analysis for the Formula C$_{31}$H$_{33}$N$_5$O$_5$ (555.64):
Calculated: C, 67.01; H, 5.99; N, 12.60%.
Found: C, 66.44; H, 6.00; N, 12.44%.

Process B (Catalytic Hydrogenation of The Triple Bond to a Single Bond)

The compound containing a triple bond (6 mmoles) is dissolved in 20 ml of methanol, measured into an autoclave of 70 ml, 5% palladium on bone coal (0.30 g) is added to it, and saturation is carried out at a hydrogen pressure of 10 bar. After 2 hours the solution is filtered and evaporated. The residual product is a yellow oil.

Purification method 1 The oil is dissolved in 200 ml of ether, the small amount of floating precipitate is filtered off, and to the pure solution a solution of the calculated amount (1 molar equivalent) of hydrogen chloride in 50 ml of diethyl ether is dropped at room temperature within half an hour, under vigorous stirring. The separated white salt is filtered, washed with ether and hexane and dried in a vacuum pistol at room temperature for 3 hours. If it is necessary, the hydrogen chloride salt is recrystallized.

Purification method 2 If the basic product does not provide a well-filterable salt with hydrogen chloride, it is dissolved in 200 ml of hot ethyl acetate, and 1 molar equivalent of a solution of oxalic acid dihydrate in 50 ml of hot ethyl acetate is dropped to it under stirring within 10 minutes. The white oxalate salt separates upon cooling. It is filtered off at room temperature, washed with ethyl acetate and hexane and dried.

EXAMPLE 24

1-Benzyl-3-ethyl-3-[4-(4-pyrimidin-2-yl-piperazin-1-yl)-butyl]-1,3-dihydro-2H-indol-2-one monooxalate The title compound is prepared according to process B by applying purification method 2 starting from 1-benzyl-3-ethyl-3-[4-(4-pyrimidin-2-yl-piperazin-1-yl)-but-2-inyl]-1,3-dihydro-2H-indol-2-one.
M.p.: 145-146° C.
IR (KBr): 1702 (C=O) cm$^{-1}$.
$^1$H-NMR (CDCl$_3$, TMS, 400 MHz): 10.0 (1H, br s), 7.30-7.20 (5H, m), 7.17 (1H, t, J=7.6 Hz), 7.13 (1H, d, J=6.7 Hz), 7.05 (1H, t, J=7.4 Hz), 6.61 (1H, t, J=4.8 Hz,), 4.98, 4.83 (2H, d, J=15, 6 Hz), 4.13 (4H, br s), 3.10 (4H, br s), 2.84 (2H, m), 1.95 (2H, m), 1.84-1.74 (2H, m), 1.60 (2H, m), 1.01-0.84 (2H, m), 0.59 (3H, t, J=7.3 Hz) ppm.
$^{13}$C-NMR (CDCl$_3$, TMS, 101 MHz): 179.7, 163.2, 160.8, 157.9, 143.1, 136.1, 131.4, 128.7, 127.8, 127.6, 127.4, 122.8, 122.7, 111.4, 108.9, 57.1, 53.2, 51.8, 43.7, 40.8, 36.9, 31.2, 23.4, 21.6, 8.6 ppm
Analysis for the Formula C$_{31}$H$_{37}$N$_5$O$_5$ (559.67):
Calculated: C, 66.53; H, 6.66; N, 12.51%.
Found: C, 65.88; H, 6.65; N, 12.45%.

EXAMPLE 25

1-Benzyl-3-ethyl-3-{4-[4-(2-methoxyphenyl)-piperazin-1-yl]-butyl}-1,3-dihydro-2H-indol-2-one monooxalate The title compound is prepared according to process B by applying purification method 2 starting from 1-benzyl-3-ethyl-3-{4-[4-(2-methoxyphenyl)-piperazin-1-yl]-but-2-inyl}-1,3-dihydro-2H-indol-2-one.
M.p.: 128-129° C.
IR (KBr): 3432, 1704 (C=O) cm$^{-1}$.
$^1$H-NMR (CDCl$_3$, TMS, 400 MHz): 7.32-7.21 (5H, m), 7.18 (1H, dt, J=1.3, 7.7 Hz,), 7.13 (1H, d, J=6.5 Hz), 7.06 (2H, m), 6.90 (3H, m), 6.77 (1H, d, J=7.7 Hz), 5.7 (2H, br s), 4.99, 4.84 (2×1H, d, J=15.4 Hz), 3.86 (3H, s), 3.58 (2H, dd, J=11.6, 27.6), 3.46 (2H, m), 3.25 (2H, m), 2.97 (2H, t, J=10.6 Hz), 2.85 (2H, m), 1.96 (2H, m), 1.81 (2H, m), 1.67 (2H, q, J=8.0 Hz), 0.95 (2H, m), 0.60 (3H t, J=7.4 Hz) ppm.

¹³C-NMR (CDCl₃, TMS, 101 MHz): 179.8, 163.0, 151.9, 143.1, 136.8, 136.1, 131.4, 129.6, 128.6, 127.8, 127.6, 127.6, 127.4, 122.8, 122.7, 121.1, 118.7, 111.6, 108.9, 57.0, 55.4, 53.4, 52.4, 47.5, 43.7, 36.9, 31.1, 23.4, 21.6, 8.6 ppm.

Analysis for the Formula C₃₄H₄₁N₃O₆ (587.72):
Calculated: C, 69.49; H, 7.03; N, 7.15%.
Found: C, 69.08; H, 6.94; N, 7.13%.

EXAMPLE 26

3-Ethyl-1-methyl-3-[4-(4-phenylpiperazin-1-yl)-butyl]-1,3-dihydro-2H-indol-2-one monohydrochloride The title compound is prepared according to process B by applying purification method 1 starting from 3-ethyl-1-methyl-3-[4-(4-phenylpiperazin-1-yl)-but-2-inyl]-1,3-dihydro-2H-indol-2-one.

M.p.: 219-222° C.
IR (KBr): 2370, 1711 (C=O) cm⁻¹.
¹H-NMR (CDCl₃, TMS, 400 MHz): 12.8 (1H, br s), 7.4-7.35 (4H, m), 7.28 (1H, t, J=7.5 Hz), 7.18 (1H, m), 7.13 (1H, d, J=6.7 Hz), 7.09 (1H, t, J=7.3 Hz), 6.85 (1H, d, J=7.8 Hz), 4.10 (2H, br s), 3.65-3.50 (6H, m), 3.21 (3H, s), 2.97 (2H, br s), 2.03-1.70 (6H, m), 1.07-0.89 (2H, m), 0.54 (3H, t, J=7.3 Hz) ppm.
¹³C-NMR (CDCl₃, TMS, 101 MHz): 179.3, 143.7, 131.1, 129.7, 127.7, 125.5, 122.4, 118.8, 107.7, 56.6, 53.1, 50.1, 49.8, 48.4, 36.3, 30.7, 25.8, 23.2, 21.3, 8.2 ppm.

Analysis for the Formula C₂₅H₃₄ClN₃O (428.02):
Calculated: H, 8.01; N, 9.82%.
Found: H, 7.56; N, 9.35%.

EXAMPLE 27

3-Ethyl-1-methyl-3-[4-(4-pyrimidin-2-yl-piperazin-1-yl)-butyl]-1,3-dihydro-2H-indol-2-one monooxalate The title compound is prepared according to process B by applying purification method 2 starting from 3-ethyl-1-methyl-3-[4-(4-pyrimidin-2-yl-piperazin-1-yl)-but-2-inyl]-1,3-dihydro-2H-indol-2-one.

M.p.: 150-152° C.
IR (KBr): 1706 (C=O) cm⁻¹.
¹H-NMR (CDCl₃, TMS, 400 MHz): 9.7 (2H, br s), 8.33 (2H, d, J=4.8 Hz), 7.28 (1H, dt, J=1.8, 7.5 Hz), 7.12 (1H, dd, J=1.5, 7.2 Hz), 7.09 (1H, t, J=7.3 Hz), 6.84 (1H, d, J=7.8 Hz), 6.60 (1H, t, J=4.8 Hz), 4.14 (4H, br s), 3.20 (3H s), 3.15 (4H, br s), 2.88 (2H, m), 1.91 (1H, m), 1.88 (1H, m), 1.74 (2H, m), 1.62 (2H, m), 0.54 (3H, t, J=7.3 Hz) ppm.
¹³C-NMR (CDCl₃, TMS, 101 MHz): 179.7, 163.2, 160.8, 157.8, 143.9, 131.3, 127.9, 122.7, 122.6, 111.3, 107.9, 57.1, 53.3, 51.8, 40.7, 36.5, 31.0, 26.0, 23.4, 21.6, 8.4 ppm.

Analysis for the Formula C₂₅H₃₃N₅O₅ (483.57):
Calculated: C, 62.10; H, 6.88; N, 14.48%.
Found: C, 61.99; H, 6.89; N, 14.45%.

Process C (Bromination of the Butynol Compounds)

The appropriate substituted piperazin-1-yl-but-2-yn-1-ol dihydrochloride (20 mmoles) is measured into 50 ml of phosphorous tribromide and allowed to react for 2 hours at 100° C. It is cooled, 20 ml of dichloromethane are added to it, the off-white substance is filtered and used for the coupling reaction without further purification.

EXAMPLE 28

1-(4-Bromobut-2-ynyl)-4-(2-methoxyphenyl)-piperazine dihydrochloride

The title compound is prepared according to process C starting from 4-[4-(2-methoxyphenyl)-piperazin-1-yl]-but-2-yn-1-ol dihydrochloride.

M.p.: 185-190° C.
¹H-NMR (DMSO-d₆, TMS, 200 MHz): 9.8 (2H, br s), 7.14-6.88 (4H, m), 4.47 (2H, s), 4.42 (2H, s), 3.81 (3H, s), 3.00-3.71 (8H, m) ppm.

EXAMPLE 29

2-[4-(4-Bromobut-2-ynyl)-piperazin-1-yl]-pyrimidine dihydrochloride

The title compound is prepared according to process C starting from 4-(4-pyrimidin-2-yl-piperazin-1-yl)-but-2-yn-1-ol dihydrochloride.

M.p.: 148-151° C.
¹H-NMR (DMSO-d₆, TMS, 200 MHz): 8.56 (2H, m), 8.4 (2H, br s), 6.87 (1H, m), 4.66 (2H, s), 4.06 (2H, m), 3.8-3.1 (8H, m) ppm.

EXAMPLE 30

1-(4-Bromobut-2-ynyl)-4-phenylpiperazine dihydrochloride

The title compound is prepared according to process C starting from 4-(4-phenylpiperazin-1-yl)-but-2-yn-1-ol dihydrochloride.

M.p.: 195-200° C.
¹H-NMR (DMSO-d₆, TMS, 200 MHz): 9.5 (2H, m), 7.27 (2H, t, J=8.0 Hz), 7.02 (2H, d, J=7.9 Hz), 6.92 (1H, t, J=7.0 Hz), 4.43 (2H, s), 4.41 (2H, s), 4.0-3.0 (8H, m) ppm.

EXAMPLE 31

1-(4-Bromobut-2-ynyl)-4-(3-chlorophenyl)-piperazine dihydrochloride

The title compound is prepared according to process C starting from 4-[4-(3-chlorophenyl)-piperazin-1-yl]-but-2-yn-1-ol dihydrochloride.

M.p.: 168-170° C.
¹H-NMR (DMSO-d₆, TMS, 200 MHz): 8.4 (2H, m), 7.28 (1H, t, J=8.0 Hz), 7.07 (1H, s), 6.98 (1H, d, J=8.4 Hz), 6.89 (1H, d, J=8.4 Hz), 4.41 (4H, br s), 4.0 (2H, br s), 3.6 (2H, br s), 3.2 (2H, br s) ppm.

Process D (Coupling of 3-Ethyl Oxindole with Bromobutynyl Compounds)

Sodium hydride (6.75 g; 50% suspension; 0.14 mole) is washed three times with 20 ml each of hexane and suspended in 50 ml of DMF. The reaction mixture is cooled to −20° C. and a solution of 3-ethyl oxindole (6.45 g; 0.04 mmole) in 25 ml of DMF is dropped to it at the same temperature. When the formation of hydrogen has been ceased the hydrochloride salt of the appropriate bromine compound containing a triple bond (0.04 mole) dissolved in 75 ml of DMF is dropped to it at −20° C. The reaction mixture is stirred for 3 hour, 5 ml of water are dropped to it in order to decompose excess of sodium hydride, and the mixture is extracted with water and diethyl ether. The organic phase is dried over sodium sulfate, clarified with bone coal, filtered and evaporated. The residual pale yellow oil is purified by column chromatography using a 10:1 mixture of dichloromethane and methanol as eluent.

Purification method 1 If the product purified by column chromatography gets crystalline upon trituration with diethyl ether, it is filtered off and recrystallized from a mixture of hexane and ethyl acetate. The desired compounds are obtained in form of white crystals.

Purification method 2 If the basic product does not get crystalline upon the addition of diethyl ether, it is dissolved in 100 ml of hot ethyl acetate, and 1 molar equivalent of a solution of oxalic acid dihydrate in 50 ml of hot ethyl acetate is dropped to it under stirring within 10 minutes. The white oxalate salt separates upon cooling. It is filtered off at room temperature, washed with ethyl acetate and hexane and dried.

EXAMPLE 32

3-Ethyl-3-[4-(4-phenylpiperazin-1-yl)-but-2-inyl]-1,3-dihydro-2H-indol-2-one monooxalate The title compound is prepared according to process D by applying purification method 2 starting from 1-(4-bromobut-2-ynyl)-4-phenyl-piperazine dihydrochloride.

M.p.: 94-95° C.

IR (KBr): 3210, 1715 (C=O) cm$^{-1}$.

$^1$H-NMR (CDCl$_3$, TMS, 400 MHz): 9.99 (1H, br s), 7.28-7.20 (2H, m), 7.12 (1H, d, J=7.3 Hz), 7.06 (1H, t, J=7.5 Hz), 6.99-6.86 (5H, m), 3.84, 3.67 (2×1H, d, J=16.5 Hz), 3.27 (4H, br s), 2.89 (4H, br s), 2.76, 2.62 (2×1H, d, J=16.4 Hz), 1.87 (2H, m), 0.63 (3H, t, J=7.3 Hz) ppm.

$^{13}$C-NMR (CDCl$_3$, TMS, 101 MHz): 180.7, 164.3, 149.6, 142.3, 131.1, 129.2, 127.9, 122.7, 122.1, 120.9, 116.6, 110.7, 86.9, 69.5, 53.3, 49.9, 46.4, 45.6, 29.7, 27.2, 8.7 ppm.

Analysis for the Formula C$_{26}$H$_{29}$N$_3$O$_5$ (463.54):
Calculated: C, 67.37; H, 6.31; N, 9.07%.
Found: C, 66.71; H, 6.18; N, 8.90%.

EXAMPLE 33

3-Ethyl-3-[4-(4-pyrimidin-2-yl-piperazin-1-yl)-but-2-ynyl]-1,3-dihydro-2H-indol-2-one monooxalate The title compound is prepared according to process D by applying purification method 2 starting from 2-[4-bromobut-2-ynyl)-piperazin-1-yl]-pyrimidine dihydrochloride.

M.p.: 147-149° C.

IR (KBr): 1714 (C=O), 1644, 1227, 754 cm$^{-1}$.

$^1$H-NMR (DMSO-d$_6$, TMS, 400 MHz): 10.4 (1H, s), 9.8 (2H, br s), 8.36 (2H, d, J=4.8 Hz), 7.23(1H, d, J=7.1 Hz), 6.93 (1H, dt, J=1.2, 7.6 Hz), 6.84 (1H, dt, J=0.9, 7.4 Hz), 6.67 (1H, d, J=7.8 Hz), 6.64 (1H, t, J=4.8 Hz), 3.69 (4H, br s), 3.44 (2H, s), 2.70, 2.51 (2×1H, d, J=16.4 Hz), 2.44 (4H, m), 1.80-1.60 (2H, m), 0.45 (3H, t, J=7.3 Hz) ppm.

$^{13}$C-NMR (DMSO-d$_6$, TMS, 101 MHz): 179.8, 163.2, 142.7, 131.5, 127.3, 123.6, 121.7, 110.8, 109.4, 109.4, 83.8, 73.4, 52.4, 50.0, 45.7, 41.7, 29.3, 26.7, 8.7 ppm.

Analysis for the Formula C$_{24}$H$_{27}$N$_5$O$_5$ (465.51):
Calculated: C, 61.92; H, 5.85; N, 15.04%.
Found: C, 61.17; H, 5.84; N, 14.86%.

EXAMPLE 34

3-Ethyl-3-{4-[4-(2-methoxyphenyl)-piperazin-1-yl]-but-2-inyl}-1,3-dihydro-2H-indol-2-one The title compound is prepared according to process D by applying purification method 1 starting from 1-(4-bromobut-2-ynyl)-4-(2-methoxy-phenyl)-piperazine dihydrochloride.

M.p.: 161-163° C.

IR (KBr): 3077, 1715 (C=O) cm$^{-1}$.

$^1$H-NMR (CDCl$_3$, TMS, 400 MHz):9.19 (1H, s), 7.21 (1H, d, J=6.9 Hz), 7.11 (1H, dt, J=1.2, 7.7 Hz), 7.08-6.90 (5H, m), 6.65 (1H, d, J=7.5 Hz), 3.96 (3H, s), 3.29 (1H, d, J=16.2 Hz), 3.17 (1H, dt, J=2.3, 16.7 Hz), 3.15 (2H, br s), 2.91 (2H br s), 2.78 (1H, dt, J=2.3, 16.2 Hz), 2.65 (2H, d, J=16.7 Hz), 2.60 (2H, br s), 2.45 (2H, br s), 2.00-1.80 (2H, m), 0.68 (3H, t, J=7.4 Hz) ppm.

$^{13}$C-NMR (CDCl$_3$, TMS, 101 MHz): 180.6, 152.0, 141.9, 141.3, 131.7, 127.7, 123.3, 123.0, 122.3, 121.2, 118.7, 111.1, 109.7, 81.3, 75.6, 55.0, 53.4, 50.6, 50.2, 46.7, 29.7, 27.7, 8.7 ppm.

Analysis for the Formula C$_{25}$H$_{29}$N$_3$O$_2$ (403.53):
Calculated: C, 74.41; H, 7.24; N, 10.41%.
Found: C, 73.43; H, 7.36; N, 10.19%.

EXAMPLE 35

3-{4-[4-(3-Chlorophenyl)-piperazin-1-yl]-but-2-ynyl}-3-ethyl-1,3-dihydro-2H-indol-2-one monohydrochloride The preparation of ethyl-(3-ethyl-2-oxo-2,3-dihydroindol)-1-carboxylate is carried out according to methods known from the literature.

Sodium hydride (1.59 g; 50% suspension; 33 mmoles) is washed three times with 10 ml each of hexane and suspended in 30 ml of DMF. The reaction mixture is cooled to −20° C., and a solution of ethyl-(3-ethyl-2-oxo-2,3-dihydro-indole)-1-carboxylate (2.32 g; 10 mmoles) in 10 ml of DMF is dropped to it at the same temperature. When the formation of hydrogen has been ceased a solution of 1-(4-chlorobut-2-ynyl)-4-(3-chlorophenyl)-piperazine dihydrochloride (3.56 g; 10 mmoles) in 20 ml of DMF is dropped to it at −20° C. The mixture is stirred for 5 hours, 5 ml of water are dropped to it in order to decompose excess of sodium hydride and extracted with water and diethyl ether. The organic phase is dried over sodium sulfate, clarified with bone coal, filtered and evaporated. The residual pale yellow oil is dissolved in 100 ml of ethyl acetate, and a solution of 1 molar equivalent of hydrogen chloride in 20 ml of ethyl acetate is dropped to it under stirring. The separated off-white salt is filtered, washed with ethyl acetate and hexane and recrystallized from isopropanol.

Yield: 1.06 g of white powder (24%).

M.p.: 201-203° C.

IR (KBr): 3166, 1712 (C=O), 760 cm$^{-1}$.

$^1$H-NMR (CDCl$_3$, TMS, 400 MHz): 9.96 (1H, s), 7.22 (1H, t, J=8.1 Hz), 7.16 (1H, d, J=7.0 Hz), 7.10-6.85 (6H, m), 4.0-2.57 (11H, m), 2.82 (1H, d, J=16.4 Hz), 2.68 (1H, d, J=16.4 Hz), 1.91 (1H, m), 1.80 (1H, m), 0.65 (3H, t, J=7.3 Hz) ppm.

$^{13}$C-NMR (CDCl$_3$, TMS, 101 MHz): 180.4, 150.6, 141.9, 135.0, 131.0, 130.3, 127.9, 122.8, 122.3, 120.9, 116.7, 114.7, 110.6, 87.9, 68.5, 53.3, 49.5, 45.7, 29.7, 27.4, 8.7 ppm.

Analysis for the Formula C$_{24}$H$_{27}$Cl$_2$N$_3$O (444.41):
Calculated: C, 64.87; H, 6.12; Cl, 15.96; N, 9.46%.
Found: C, 64.82; H, 6.11; Cl, 15.94; N, 9.43%.

EXAMPLE 36

(Z)-3-{4-[4-(3-Chlorophenyl)-piperazin-1-yl]-but-2-enil}-3-ethyl-1,3-dihydro-2H-indol-2-one monohydrochloride 3-{4-[4-(3-Chlorophenyl)-piperazin-1-yl]-but-2-ynyl}-3-ethyl-1,3-dihydro-2H-indol-2-one monohydrochloride (7.15 g; 16 mmoles) is suspended in 150 ml of THF and Raney-nickel (1.0 g) is added to it. Hydrogenation is carried out for 10 hours in an autoclave under a starting pressure of 10 bar at a temperature of 90° C. The product is then dissolved in methanol, the catalyst is filtered off and the filtrate is evaporated. The hydrochloride salt of the compound of (Z) configuration containing a double bond separates in form of off-white substance.

Yield: 3.49 g of off-white powder (49%).
M.p.: 219-222° C.
IR (KBr): 3116, 2569, 1699 (C=O) cm$^{-1}$.
$^1$H-NMR (DMSO-d$_6$, TMS, 400 MHz): 11.4 (1H, br s), 10.5 (1H, s), 7.29 (1H, d, J=47.9 Hz), 7.25 (1H, d, J=8.1 Hz), 7.18 (1H, t, J=7.4 Hz), 7.03 (1H, s), 6.99 (1H, t, J=7.4 Hz), 6.94 (1H, dd, J=1.8, 8.4 Hz), 6.86 (2H, d, J=7.5 Hz), 5.58 (1H, m), 5.43 (1H, m), 3.84 (2H, br s), 3.71 (2H, br s), 3.30 (2H, br s), 3.00 (2H, br s), 2.65, 2.55 (2×1H, dd, J=7.3, 14.2 Hz), 1.80 (2H, m), 052 (3H, t, J=7.3 Hz) ppm.
$^{13}$C-NMR (DMSO-d$_6$, TMS, 101 MHz): 180.2, 150.8, 142.4, 134.0, 133.1, 131.4, 130.7, 127.3, 123.5, 121.5, 121.5, 120.9, 119.2, 115.3, 109.4, 52.9, 51.3, 49.7, 44.9, 34.6, 29.6, 8.5 ppm.

Analysis for the Formula C$_{24}$H$_{29}$Cl$_2$N$_3$O (446.42):
Calculated: C, 64.57; H, 6.55; Cl, 15.88; N, 9.41%.
Found: C, 64.11; H, 6.95; Cl, 15.65; N, 9.27%.

Process E (Preparation of ω-Haloalkyl Compounds)

Into a flask rinsed with argon 2.5 M n-butyl lithium (60 ml; 0.15 mole) is measured. 200 ml of THF are added to it, and the solution is cooled in an acetone-dry ice bath to −78° C. At this temperature a solution of 3-alkyl oxindole (0.20 mole) in 250 ml of THF is dropped to it under stirring. The mixture is stirred for further 10 minutes, a dihaloalkane (1-bromo-4-chlorobutane, 1-bromo-3-chloropropane, 1,5-dibromopentane or 1,6-dibromohexane; 0.50 mole) is dropped to it, and the solution is allowed to warn up to room temperature. Then it is stirred further for 3 hours, and 20 ml of ethanol is dropped to it in order to decompose excess of butyl lithium. The solution is distilled in a rotary evaporator, and the residual oil is extracted with water and ethyl acetate. The organic phase is dried over sodium sulfate. The residual oil is made crystalline by trituration with hexane. The separated off-white crystals are stirred in 200 ml of hexane in order to remove excess of dihaloalkane, filtered and washed with hexane. The product is used for the further reactions without recrystal-lization. Analytical samples may be obtained by recristallization from the indicated solvent.

EXAMPLE 37

3-(4-Chlorobutyl)-3-ethyl-1,3-dihydro-2H-indol-2-one

The title compound is prepared according to process E starting from 3-ethyl-1,3-dihydro-2H-indol-2-one and 1-bromo-4-chlorobutane.

M.p.: 104-105° C. (hexane-ethyl acetate).
IR (KBr): 3181, 2941, 1700, 1306, 755 cm$^{-1}$.
$^1$H-NMR (CDCl$_3$, TMS, 400 MHz): 8.57 (br s, 1H, NH), 7.21 (dt, 1H, J=7.6, 1.5 Hz, H-6), 7.12 (d, 1H, J=7.4 Hz, H-4), 7.06 (dt, 1H, J=7.5, 1.0 Hz, H-5), 6.92 (d, 1H, J=7.7 Hz, H-7), 3.39 (t, 2H, J=6.7 Hz, CH$_2$Cl), 1.96-1.84 (m, 2H, CH$_2$), 1.83-1.74 (m, 2H, CH$_2$), 1.74-1.60 (m, 2H, CH$_2$), 1.24-1.18 (m, 1H), 1.08-1.03 (m, 1H), 0.64 (t, 3H, J=7.4 Hz, CH$_3$) ppm.
$^{13}$C-NMR (CDCl$_3$, TMS, 101 MHz): 182.4, 141.2, 132.3, 127.7, 123.0, 122.5, 109.6, 54.1, 44.4, 36.8, 32.7, 31.0, 21.8, 8.5 ppm.

Analysis for the Formula C$_{14}$H$_{18}$ClNO (251.76):
Calculated: C, 66.79; H, 7.21; N, 5.56; Cl, 14.08%.
Found: C, 66.89; H, 7.16; N, 5.84; Cl, 14.19%.

EXAMPLE 38

3-(4-Chlorobutyl)-3-ethyl-5-fluoro-1,3-dihydro-2H-indol-2-one

The title compound is prepared according to process E starting from 3-ethyl-5-fluoro-1,3-dihydro-2H-indol-2-one and 1-bromo-4-chloro-butane.

M.p.: 96-97° C. (hexane-ethyl acetate).
IR (KBr): 3159, 1716, 817 cm$^{-1}$.
$^1$H-NMR (CDCl$_3$, TMS, 400 MHz): 8.99 (br s, 1H, NH), 6.95-6.85 (m, 3H), 3.40 (t, 2H, J=6.7 Hz, CH$_2$Cl), 1.97-1.88 (m, 2H, CH$_2$), 1.83-1.75 (m, 2H, CH$_2$), 1.73-1.62 (m, 2H), 1.25-1.20 (m, 1H), 1.09-1.04 (m, 1H), 0.65 (t, 3H, J=7.4 Hz, CH$_3$) ppm.
$^{13}$C-NMR (CDCl$_3$, TMS, 101 MHz): 182.5, 159.3 (d, J=240.7 Hz), 137.2, 134.1 (d, J=7.6 Hz), 114.1 (d, J=23.7 Hz), 111.9 (d, J=24.4 Hz), 110.2 (d, J=2.0 Hz), 54.8 (d, J=2.0 Hz), 44.4, 36.8, 32.5, 31.0, 21.7, 8.4 ppm.

Analysis for the Formula C$_{14}$H$_{17}$ClFNO (269.75).
Calculated: C, 62.34; H, 6.35; N, 5.19; Cl, 13.14%.
Found: C, 62.49; H, 6.20; N, 4.98; Cl, 13.48%.

EXAMPLE 39

3-(4-Chlorobutyl)-3-ethyl-6-fluoro-1,3-dihydro-2H-indol-2-one

The title compound is prepared according to process E starting from 3-ethyl-6-fluoro-1,3-dihydro-2H-indol-2-one and 1-bromo-4-chloro-butane.

M.p.: 95-97° C. (hexane-ethyl acetate).
IR (KBr): 3195, 1728, 1132 cm$^{-1}$.
$^1$H-NMR (CDCl$_3$, TMS, 400 MHz): 9.34 (br s, 1H, NH), 7.05 (dd, 1H, J=8.1, 5.3 Hz, H-4), 6.75 (ddd, 1H, J=9.6, 8.1, 2.4 Hz, H-5), 6.71 (dd, 1H, J=8.8, 2.4 Hz, H-7), 3.44 (t, 2H, J=6.7 Hz, CH$_2$Cl), 2.00-1.70 (m, 4H, 2×CH$_2$), 1.70-1.60 (m, 2H, CH$_2$), 1.23-1.18 (m, 1H), 1.08-1.04 (m, 1H), 0.64 (t, 3H, J=7.4 Hz, CH$_3$) ppm.
$^{13}$C-NMR (CDCl$_3$, TMS, 101 MHz): 183.3, 162.5 (d, J=244.1 Hz), 142.5 (d, J=7.8 Hz), 127.5 (d, J=13.0 Hz), 123.8 (d, J=9.5 Hz), 108.8 (d, J=22.5 Hz), 98.5 (d, J=27.4 Hz), 53.8, 44.4, 36.8, 32.5, 31.0, 21.6, 8.4 ppm.

Analysis for the Formula C$_{14}$H$_{17}$ClFNO (269.75):
Calculated: C, 62.34; H, 6.35; N, 5.19; Cl, 13.14%.
Found: C, 62.09; H, 6.22; N, 5.28; Cl, 13.43%.

EXAMPLE 40

3-(4-Chlorobutyl)-3-ethyl-5-methyl-1,3-dihydro-2H-indol-2-one

The title compound is prepared according to process E starting from 3-ethyl-5-methyl-1,3-dihydro-2H-indol-2-one and 1-bromo-4-chloro-butane.

M.p.: 79-80° C. (hexane).
IR (KBr): 3286, 1719 cm$^{-1}$.
$^1$H-NMR (CDCl$_3$, TMS, 400 MHz): 8.70 (br s, 1H, NH), 7.00 (d, 1H, J=7.8 Hz, H-6), 6.92 (s, 1H, H-4), 6.81 (d, 1H, J=7.9 Hz, H-7), 3.39 (t, 2H, J=6.8 Hz, CH$_2$Cl), 1.95-1.85 (m, 2H), 1.82-1.70 (m, 2H), 1.70-1.58 (m, 2H), 1.30-1.12 (m, 1H), 1.10-0.98 (m, 1H), 0.63 (t, 3H, J=7.3 Hz, CH$_3$) ppm.
$^{13}$C-NMR (CDCl$_3$, TMS, 101 MHz): 182.5, 138.8, 132.4, 131.9, 128.0, 123.7, 109.3, 54.1, 44.4, 36.9, 32.7, 31.0, 21.8, 8.4 ppm.
Analysis for the Formula C$_{15}$H$_{20}$ClNO (265.79):
Calculated: C, 67.79; H, 7.58; N, 5.27; Cl 13.34%.
Found: C, 67.98; H, 7.43; N, 5.11; Cl, 13.09%.

EXAMPLE 41

3-(4-Chlorobutyl)-3-ethyl-7-methyl-1,3-dihydro-2H-indol-2-one

The title compound is prepared according to process E starting from 3-ethyl-7-methyl-1,3-dihydro-2H-indol-2-one and 1-bromo-4-chloro-butane.

M.p.: 112-113° C. (hexane-ethyl acetate).
IR (KBr): 3181, 1703 (C=O), 748 cm$^{-1}$.
$^1$H-NMR (CDCl$_3$, TMS, 400 MHz): 0.63 (3H, t, J=7.4 Hz), 1.07-1.02 (1H, m), 1.25-1.17 (1H, m), 1.70-1.60 (2H, m), 1.81-1.72 (2H, m), 1.96-1.86 (2H, m), 2.31 (3H, s), 3.36 (2H, t, J=6.8 Hz), 6.94 (1H, dd, J=1.7, 7.3 Hz), 6.97 (1H, t, J=7.3 Hz), 7.03 (1H, dd, J=1.4, 7.2 Hz), 9.4 (1H, br s) ppm.
$^{13}$C-NMR (CDCl$_3$, TMS, 101 MHz): 8.5, 16.5, 21.8, 31.0, 32.7, 36.8, 44.4, 54.4, 119.1, 120.3, 122.4, 129.1, 131.9, 140.1, 183.1 ppm.
Analysis for the Formula C$_{15}$H$_{20}$ClNO (265.79): Calculated: C, 67.79; H, 7.58; N, 5.27; Cl, 13.34%. Found: C, 67.56; H, 7.49; N, 5.24; Cl, 13.29%.

EXAMPLE 42

3-(3-Chloropropyl)-3-ethyl-1,3-dihydro-2H-indol-2-one

The title compound is prepared according to process E starting from 3-ethyl-1,3-dihydro-2H-indol-2-one and 1-bromo-3-chloropropane.

M.p.: 91-93° C. (hexane).
IR (KBr): 3183, 1701, 751 cm$^{-1}$.
$^1$H-NMR (CDCl$_3$, TMS, 400 MHz): 9.15 (br s, 1H, NH), 7.23 (dt, 1H, J=7.7, 1.3 Hz, H-6), 7.14 (d, 1H, J=6.8 Hz, H-4), 7.06 (dt, 1H, J=7.4, 0.9 Hz, H-5), 6.95 (d, 1H, J=7.7 Hz, H-7), 3.48-3.36 (m, 2H, CH$_2$Cl), 2.02-1.93 (m, 3H), 1.85-1.78 (m, 1H), 1.66-1.54 (m, 1H), 1.44-1.30 (m, 1H), 0.65 (t, 3H, J=7.4 Hz, CH$_3$) ppm.
$^{13}$C-NMR (CDCl$_3$, TMS, 101 MHz): 182.6, 141.3, 132.0, 127.9, 123.0, 122.6, 109.8, 53.7, 44.8, 34.8, 31.0, 27.5, 8.5 ppm.
Analysis for the Formula C$_{13}$H$_{16}$ClNO (237.73):
Calculated: C, 65.68; H, 6.78; N, 5.89; Cl, 14.91%.
Found: C, 65.51; H, 6.70; N, 5.82; Cl, 14.68%.

EXAMPLE 43

3-(5-Bromopentyl)-3-ethyl-1,3-dihydro-2H-indol-2-one

The title compound is prepared according to process E starting from 3-ethyl-1,3-dihydro-2H-indol-2-one and 1,5-dibromopentane.

M.p.: 77-78° C. (hexane).
IR (KBr): 3290, 1718, 772 cm$^{-1}$.
$^1$H-NMR (CDCl$_3$, TMS, 400 MHz): 9.11 (br s, 1H, NH), 7.20 (dt, 1H, J=7.6, 1.4 Hz, H-6), 7.11 (d, 1H, J=7.3 Hz, H-4), 7.05 (dt, 1H, J=7.4, 1.0 Hz, H-5), 6.94 (d, 1H, J=7.4 Hz), 3.27 (t, 2H, J=6.9 Hz, CH$_2$Br), 1.98-1.86 (m, 2H, CH$_2$), 1.84-1.74 (m, 2H, CH$_2$), 1.71 (quintet, 2H, J=7.2 Hz, CH$_2$), 1.38-1.24 (m, 2H), 1.18-1.04 (m, 1H), 0.96-0.84 (m, 1H), 0.63 (t, 3H, J=7.4 Hz, CH$_3$) ppm.
$^{13}$C-NMR (CDCl$_3$, TMS, 101 MHz): 182.9, 141.4, 132.5, 127.6, 122.9, 122.4, 109.7, 54.2, 37.4, 33.6, 32.4, 31.0, 28.2, 23.4, 8.5 ppm.
Analysis for the Formula C$_{15}$H$_{20}$BrNO (310.24):
Calculated: C, 58.07; H, 6.50; N, 4.51; Br, 25.76%.
Found: C, 57.95; H, 6.42; N, 4.67; Br, 25.58%.

EXAMPLE 44

3-(4-Chlorobutyl)-3-isobutyl-1,3-dihydro-2H-indol-2-one

The title compound is prepared according to process E starting from 3-isobutyl-1,3-dihydro-2H-indol-2-one and 1-bromo-4-chlorobutane.

M.p.: 124-125° C. (hexane-ethyl acetate).
IR (KBr): 3208, 1713, 747 cm$^{-1}$.
$^1$H-NMR (CDCl$_3$, TMS, 400 MHz): 9.02 (br s, 1H, NH), 7.21 (dt, 1H, J=7.5, 1.4 Hz, H-6), 7.11 (td, 1H, J=7.4, 0.6 Hz, H-4), 7.04 (dt, 1H, J=7.4, 1.0 Hz, H-5), 6.95 (d, 1H, J=7.7 Hz, H-7), 3.37 (t, 2H, J=6.7 Hz, CH$_2$Cl), 1.95-1.70 (m, 4H, 2×CH$_2$), 1.70-1.58 (m, 2H, CH$_2$), 1.38-1.30 (m, 1H), 1.23-1.17 (m, 1H), 1.02-0.98 (m, 1H), 0.73 (d, 3H, J=6.6 Hz, CH$_3$), 0.61 (d, 3H, J=6.6 Hz, CH$_3$) ppm.
$^{13}$C-NMR (CDCl$_3$, TMS, 101 MHz): 183.1, 141.1, 132.6, 127.7, 123.3, 122.3, 109.8, 53.0, 46.3, 44.4, 39.2, 32.6, 25.3, 24.2, 23.6, 21.1 ppm.
Analysis for the Formula C$_{16}$H$_{22}$ClNO (279.81):
Calculated: C, 68.68; H, 7.93; N, 5.01; Cl, 12.67%.
Found: C, 68.49; H, 7.89; N, 4.92; Cl, 12.89%.

EXAMPLE 45

3-(5-Bromopentyl)-3-ethyl-5-fluoro-1,3-dihydro-2H-indol-2-one

The title compound is prepared according to process E starting from 3-ethyl-5-fluoro-1,3-dihydro-2H-indol-2-one and 1,5-dibromopentane.

M.p.: 82-83° C. (hexane).
IR (KBr): 3293, 1720, 1690, 1175, 817 cm$^{-1}$.
$^1$H-NMR (CDCl$_3$, TMS, 400 MHz): 7.96 (br s, 1H, NH), 6.92 (dt, 1H, J=8.8, 2.6 Hz, H-6), 6.86 (dd, 1H, J=8.0, 2.6 Hz, H-4), 6.82 (dd, 1H, J=8.4, 4.3 Hz, H-7), 3.30 (t, 2H, J=6.9 Hz, CH$_2$Br), 1.96-1.87 (m, 2H, CH$_2$), 1.80-1.68 (m, 4H, 2×CH$_2$), 1.40-1.25 (m, 2H, CH$_2$), 1.18-1.04 (m, 1H), 0.96-0.84 (m, 1H), 0.64 (t, 3H, J=7.4 Hz, CH$_3$) ppm.

¹³C-NMR (CDCl₃, TMS, 101 MHz): 181.8, 159.3 (d, J=240.7 Hz), 136.9, 134.4 (d, J=8.0 Hz), 114.0 (d, J=23.3 Hz), 111.0 (d, J=24.4 Hz), 109.9 (d, J=8.0 Hz), 54.7, 37.5, 33.6, 32.4, 31.1, 28.2, 23.5, 8.5 ppm.

Analysis for the Formula $C_{15}H_{19}BrFNO$ (328.23):
Calculated: C, 54.89; H, 5.83; N, 4.27; Br, 24.34%.
Found: C, 54.68; H, 5.89; N, 4.35; Br, 24.16%.

EXAMPLE 46

3-(5-Bromopentyl)-3-ethyl-5-methyl-1,3-dihydro-2H-indol-2-one

The title compound is prepared according to process E starting from 3-ethyl-5-methyl-1,3-dihydro-2H-indol-2-one and 1,5-dibromopentane.

M.p.: 72-73° C. (hexane).
IR (KBr): 3262, 1726, 1694, 812 cm⁻¹.

¹H-NMR (CDCl₃, TMS, 400 MHz): 7.55 (br s, 1H, NH), 7.00 (d, 1H, J=7.9 Hz, H-6), 6.92 (s, 1H, H-4), 6.75 (d, 1H, J=7.8 Hz, H-7), 3.30 (t, 2H, J=6.8 Hz, CH₂Br), 1.94-1.84 (m, 2H, CH₂), 1.79-1.68 (m, 4H, 2×CH₂), 1.35-1.24 (m, 2H, CH₂), 1.24-1.13 (m, 1H), 0.93-0.84 (m, 1H), 0.63 (t, 3H, J=7.4 Hz, CH₃) ppm.

¹³C-NMR (CDCl₃, TMS, 101 MHz): 181.8, 159.3 (d, J=240.7 Hz), 136.9, 134.4 (d, J=8.0 Hz), 114.0 (d, J=23.3 Hz), 111.0 (d, J=24.4 Hz), 109.9 (d, J=8.0 Hz), 54.7, 37.5, 33.6, 32.4, 31.1, 28.2, 23.5, 8.5 ppm.

Analysis for the Formula $C_{16}H_{22}BrNO$ (324.26):
Calculated: C, 59.27; H, 6.84; N, 4.32; Br, 24.64%.
Found: C, 59.18; H, 6.92; N, 4.55; Br, 24.51%.

EXAMPLE 47

3-(5-Bromopentyl)-3-ethyl-6-fluoro-1,3-dihydro-2H-indol-2-one

The title compound is prepared according to process E starting from 3-ethyl-6-fluoro-1,3-dihydro-2H-indol-2-one and 1,5-dibromopentane.

M.p.: 95-96° C. (hexane).
IR (KBr): 3300, 1722, 857 cm⁻¹.

¹H-NMR (CDCl₃, TMS, 400 MHz): 9.24 (br s, 1H, NH), 7.01 (dd, 1H, J=8.1, 5.3 Hz, H-5), 6.72 (ddd, 1H, J=9.6, 8.2, 2.3 Hz, H-5), 6.68 (d, 1H, J=8.8, 2.3 Hz, H-7), 3.26 (t, 2H, J=7.4 Hz, CH₂Br), 1.92-1.83 (m, 2H, CH₂), 1.80-1.65 (m, 4H, 2×CH₂), 1.35-1.25 (m, 2H, CH₂), 1.09-1.00 (m, 1H), 0.92-0.84 (m, 1H), 0.60 (t, 3H, J=7.4 Hz, CH₃) ppm.

¹³C-NMR (CDCl₃, TMS, 101 MHz): 183.3, 162.4 (d, J=244.1 Hz), 142.5 (d, J=11.8 Hz), 127.7 (d, J=3.1 Hz), 123.8 (d, J=9.9 Hz), 108.7 (d, J=22.1 Hz), 98.4 (d, J=27.1 Hz), 53.9, 37.4, 33.6, 32.3, 31.0, 28.2, 23.4, 8.4 ppm.

Analysis for the Formula $C_{15}H_{19}BrFNO$ (328.23):
Calculated: C, 54.89; H, 5.83; N, 4.27; Br, 24.34,
Found: C, 54.69; H, 5.67; N, 4.39; Br, 24.19%.

Process F (Chlorination of ω-haloalkyl Compounds in Position 5)

The haloalkyl compound (5 mmoles) is dissolved in 15 ml of glacial acetic acid, the solution is cooled until glacial acetic acid begins to separate (14-16° C.) and a solution of 0.5 ml (5.7 mmoles) of sulfuryl chloride in 5 ml of glacial acetic acid is dropped to it. The mixture is stirred for 2 hours at the same temperature and then pipetted onto ice-water. The separated white substance is filtered, washed with water and hexane, dried and used for the coupling reaction without purification. Analytical samples may be obtained by recrystallization from the indicated solvent.

EXAMPLE 48

5-Chloro-3-(4-chlorobutyl)-3-ethyl-1,3-dihydro-2H-indol-2-one

The title compound is prepared according to process F starting from 3-(4-chlorobutyl)-3-ethyl-1,3-dihydro-2H-indol-2-one.

M.p.: 116-117° C. (hexane-ethyl acetate).
IR (KBr): 3285, 1717, 818 cm⁻¹.

¹H-NMR (CDCl₃, TMS, 400 MHz): 8.72 (br s, 1H, NH), 7.15 (dd, 1H, J=8.2, 2.1 Hz, H-6), 7.12 (d, 1H, J=2.1 Hz, H-4), 6.86 (d, 1H, J=8.2 Hz, H-7), 3.41 (t, 2H, J=6.7 Hz, CH₂Cl), 2.00-1.86 (m, 2H, CH₂), 1.84-1.74 (m, 2H, CH₂), 1.74-1.60 (m, 2H), 1.29-1.15 (m, 1H), 1.12-0.95 (m, 1H), 0.65 (t, 3H, J=7.4 Hz, CH₃) ppm.

¹³C-NMR (CDCl₃, TMS, 101 MHz): 182.0, 139.8, 134.2, 127.9, 127.8, 123.4, 110.7, 54.5, 44.4, 36.8, 32.5, 31.0, 21.7, 8.5 ppm.

Analysis for the Formula $C_{14}H_{17}Cl_2NO$ (286.20):
Calculated: C, 58.75; H, 5.99; N, 4.89; Cl, 24.77%.
Found: C, 58.61; H, 5.96; N, 4.80; Cl, 24.66%.

EXAMPLE 49

5-Chloro-3-(3-chloropropyl)-3-ethyl-1,3-dihydro-2H-indol-2-one

The title compound is prepared according to process F starting from 3-(3-chloropropyl)-3-ethyl-1,3-dihydro-2H-indol-2-one.

M.p.: 105-107° C. (hexane).
IR (KBr): 3221, 2963, 1700 (C=O), 1677, 1474 cm⁻¹.

¹H-NMR (CDCl₃, TMS, 400 MHz): 9.15 (br s, 1H, NH), 7.21 (dd, 1H, J=8.2, 2.1 Hz, H-6), 7.12 (d, 1H, J=2.0 Hz, H-4), 6.88 (d, 1H, J=8.2 Hz, H-7), 3.43-3.39 (m, 2H, CH₂Cl), 2.10-1.77 (m, 4H, 2×CH₂), 1.62-1.55 (m, 1H), 1.42-1.38 (m, 1H), 0.66 (t, 3H, J=7.4 Hz, CH₃) ppm.

¹³C-NMR (CDCl₃, TMS, 101 MHz): 182.1, 139.8, 133.9, 128.1, 128.0, 123.5, 110.8, 54.1, 44.6, 34.7, 30.9, 27.5, 8.5 ppm.

Analysis for the Formula $C_{13}H_{15}Cl_2NO$ (272.18):
Calculated: C, 57.37; H, 5.56; N, 5.15; Cl, 26.05%.
Found: C, 57.19; H, 5.64; N, 5.28; Cl, 25.88%.

EXAMPLE 50

5-Chloro-3-(4-chlorobutyl)-3-ethyl-6-fluoro-1,3-dihydro-2H-indol-2-one

The title compound is prepared according to process F starting from 6-fluoro-3-(4-chloro-butyl)-3-ethyl-1,3-dihydro-2H-indol-2-one.

M.p.: 131-133° C. (hexane-ethyl acetate).
IR (KBr): 3289, 1720, 1143 cm⁻¹.

¹H-NMR (CDCl₃, TMS, 400 MHz): 8.90 (br s, 1H, NH), 7.12 (d, 1H, J=7.1, H-4), 6.79 (d, 1H, J=8.8 Hz, H-7), 3.42 (t, 2H, J=6.7 Hz, CH₂Cl), 1.96-1.84 (m, 2H, CH₂), 1.80-1.63 (m, 4H, 2×CH₂), 1.30-1.20 (m, 1H), 1.20-1.04 (m, 1H), 0.65 (t, 3H, J=7.4 Hz, CH₃) ppm.

¹³C-NMR (CDCl₃, TMS, 101 MHz): 182.3, 157.6 (d, J=247.2 Hz), 140.9 (d, J=11.1 Hz), 128.8 (d, J=3.8 Hz), 124.8, 114.3 (d, J=18.3 Hz), 99.5 (d, J=26.7 Hz), 54.2, 44.3, 36.8, 32.4, 31.0, 21.6, 8.4 ppm.

Analysis for the Formula $C_{14}H_{16}Cl_2FNO$ (304.19):
Calculated: C, 55.28; H, 5.30; N, 4.60; Cl, 23.31%.
Found: C, 55.19; H, 5.27; N, 4.58; Cl, 23.34%.

Process G (5,7-Dichlorination of ω-Chloroalkyl Compounds)

A chloroalkyl compound (40 mmoles) is dissolved in 80 ml of glacial acetic acid, and 9.6 ml (120 mmoles) of sulfuryl chloride are dropped to it at room temperature. The solution is kept at 60° C. for 3 hours. Then it is cooled, poured onto ice and extracted with diethyl ether. The ether phase is extracted twice with 10% by volume NaOH solution, dried over sodium sulfate and evaporated. The thus-obtained pale yellow oil is triturated with hexane, the crystalline white substance is stirred in hexane, filtered, washed with hexane, dried and used for the coupling reaction without purification. Analytical samples may be obtained by recrystallization from the indicated solvent.

EXAMPLE 51

5,7-Dichloro-3-(4-chlorobutyl)-3-ethyl-1,3-di-hydro-2H-indol-2-one

The title compound is prepared according to process G starting from 3-(4-chlorobutyl)-3-ethyl-1,3-dihydro-2H-indol-2-one.
M.p.: 65-67° C. (hexane).
IR (KBr): 3165, 2964, 1713 (C=O), 1455 cm$^{-1}$.
$^1$H-NMR (CDCl$_3$, TMS, 400 MHz): 8.38 (br s, 1H, NH), 7.20 (d, 1H, J=1.9 Hz, H-6), 6.97 (d, 1H, J=1.8 Hz, H-4), 3.38 (t, 2H, J=6.7 Hz, CH$_2$Cl), 1.95-1.84 (m, 2H, CH$_2$), 1.76-1.60 (m, 4H, 2×CH$_2$), 1.19-1.16 (m, 1H), 1.04-0.96 (m, 1H), 0.62 (t, 3H, J=7.4 Hz, CH$_3$) ppm.
$^{13}$C-NMR (CDCl$_3$, TMS, 101 MHz): 180.5, 137.7, 135.1, 128.3, 127.6, 121.9, 115.7, 55.7, 44.3, 36.8, 32.5, 31.0, 21.7, 8.5 ppm.

Analysis for the Formula $C_{14}H_{16}Cl_3NO$ (320.65):
Calculated: C, 52.44; H, 5.03; N, 4.37; Cl, 33.17%.
Found: C, 52.37; H, 4.97; N, 4.27; Cl, 33.18%.

EXAMPLE 52

5,7-Dichloro-3-(4-chlorobutyl)-3-isobutyl-1,3-dihydro-2H-indol-2-one

The title compound is prepared according to process G starting from 3-(4-chlorobutyl)-3-isobutyl-1,3-dihydro-2H-indol-2-one.
M.p.: 93-94° C. (hexane).
IR (KBr): 3144, 1719, 1459 cm$^{-1}$.
$^1$H-NMR (CDCl$_3$, TMS, 400 MHz): 8.49 (br s, 1H, NH), 7.24 (dt, 1H, J=1.9 Hz, H-6), 7.01 (d, 1H, J=1.7 Hz, H-4), 3.41 (t, 2H, J=6.7 Hz, CH$_2$Cl), 1.91 (m, 2H, CH$_2$), 1.67 (m, 4H, 2×CH$_2$), 1.34 (m, 1H), 1.20 (m, 1H), 1.01 (m, 1H), 0.74 (d, 3H, J=6.7 Hz, CH$_3$), 0.66 (d, 3H, J=6.7 Hz, CH$_3$) ppm.
$^{13}$C-NMR (CDCl$_3$, TMS, 101 MHz): 181.0, 137.5, 135.4, 128.2, 127.6, 122.2, 115.4, 54.5, 46.3, 44.3, 39.2, 32.4, 25.3, 24.3, 23.1, 21.1 ppm.

Analysis for the Formula $C_{16}H_{20}Cl_3NO$ (348.70):
Calculated: C, 55.11; H, 5.78; N, 4.02; Cl, 30.50%.
Found: C, 55.29; H, 5.67; N, 4.12; Cl, 30.18%.

EXAMPLE 53

7-Chloro-3-(4-chlorobutyl)-3-ethyl-5-fluoro-1,3-dihydro-2H-indol-2-one 3-(4-Chlorobutyl)-3-ethyl-5-fluoro-1,3-dihydro-2H-indol-2-one (5.40 g; 20 mmoles) is dissolved in 40 ml of glacial acetic acid, 3.2 ml (40 mmoles) of sulfuryl chloride are dropped to the solution at room temperature and it is kept at 60° C. for 4 hours. Then it is cooled, poured onto ice and extracted with diethyl ether. The ether phase is extracted twice with 10% by volume NaOH solution, dried over sodium sulfate and evaporated. The thus-obtained pale yellow oil is triturated with hexane, the crystalline white substance is stirred in hexane, filtered, washed with hexane, dried and used for the coupling reaction without purification. Analytical samples may be obtained by recrystallization from a mixture of hexane and ethyl acetate.
M.p.: ° C. (hexane-ethyl acetate).
IR (KBr): 3184, 1709, 1080, 853 cm$^{-1}$.

allowed to cool, and 500 ml of water is dropped to it. The product separates in the form of white substance. The separated substance is filtered, washed with water and hexane and used for the coupling reaction without purification. Analytical samples may be obtained by recrystallization from a mixture of hexane and ethyl acetate.
M.p.: 117-118° C. (hexane-ethyl acetate).
IR (KBr): 3286, 1717, 1198, 817 cm$^{-1}$.
$^1$H-NMR (CDCl$_3$, TMS, 400 MHz): δ 9.28 (br s, 1H, NH), 7.35 (dd, 1H, J=8.2, 2.0 Hz, H-6), 7.24 (d, 1H, J=2.0 Hz, H-4), 6.84 (d, 1H, J=8.2 Hz, H-7), 3.41 (t, 2H, J=6.8 Hz, CH$_2$Cl), 1.98-1.75 (m, 2H, CH$_2$), 1.74-1.60 (m, 4H, 2×CH$_2$), 1.27-1.16 (m, 1H), 1.11-1.01 (m, 1H), 0.64 (t, 3H, J=7.4 Hz, CH$_3$);
$^{13}$C-NMR (CDCl$_3$, TMS, 101 MHz): 182.3, 140.4, 134.6, 130.7, 126.1, 115.3, 111.3, 54.5, 44.3, 36.7, 32.8, 30.9, 21.7, 8.5.

Analysis for the Formula $C_{14}H_{17}BrClNO$ (330.65):
Calculated: C, 50.86; H, 5.18; N, 4.24%.
Found: C, 50.79; H, 5.09; N, 4.38%.

EXAMPLE 55

3-(4-Chlorobutyl)-3-ethyl-2-oxoindoline-5-sulfonyl chloride 90 ml of chlorosulfonic acid are cooled to 0° C., and 3-(4-chlorobutyl)-3-ethyl-oxindole (11.34 g; 45 mmoles) is added to it in portions, so that the temperature does not exceed 2° C. The solution is then allowed to warm to room temperature under stirring and carefully pipetted onto ice in half an hour. The separated white precipitate is filtered, washed with water and hexane and used for the coupling reaction without purification. Analytical samples may be obtained by recrystallization from a mixture of hexane and ethyl acetate.
M.p.: ° C.
IR (KBr): 3197, 1729, 1371, 1176 cm$^{-1}$.
$^1$H-NMR (CDCl$_3$, TMS, 400 MHz): 9.39 (br s, 1H, NH), 7.99 (dd, 1H, J=8.4, 1.9 Hz, H-6), 7.80 (d, 1H, J=1.9 Hz, H-4), 7.16 (d, 1H, J=8.4 Hz, H-7), 3.46-3.41 (m, 2H, CH$_2$Cl), 2.10-1.83 (m, 4H, 2×CH$_2$), 1.73-1.66 (m, 2H), 1.32-1.18 (m, 1H), 1.14-1.00 (m, 1H), 0.68 (t, 3H, J=7.4 Hz, CH$_3$) ppm.
$^{13}$C-NMR (CDCl$_3$, TMS, 101 MHz): 182.4, 147.6, 138.4, 133.9, 128.8, 121.9, 110.1, 54.5, 44.3, 36.4, 32.2, 30.9, 21.5, 8.5 ppm.

Analysis for the Formula $C_{14}H_{17}Cl_2NO_3S$ (350.27):
Calculated: C, 48.01; H, 4.89; N, 4.00; Cl, 20.24, S 9.15%.
Found: C, 47.89; H, 4.76; N, 4.18; Cl, 20.01, S 9.38%.

EXAMPLE 56

3-(4-Chlorobutyl)-3-ethyl-2-oxoindoline 5-sulfonamide 3-(4-Chlorobutyl)-3-ethyl-2-oxoindoline 5-sulfonyl chloride (9.96 g; 30 mmoles) is dissolved in 450 ml of ethanol, and 25% aqueous ammonia solution (9 ml, 120 mmoles) is dropped to the solution at 0-2° C. The mixture is allowed to warm to room temperature. It is stirred further for 1 hour, evaporated, the residual white substance is stirred in water, filtered, washed with water and hexane and used for the coupling reaction without purification. Analytical samples may be obtained by recrystallization from a mixture of hexane and ethyl acetate.

M.p.: 171-172° C. (ethyl acetate).
IR (KBr): 3343, 3265, 1725, 1327, 1169 $cm^{-1}$.
$^1$H-NMR (DMSO-$d_6$, TMS, 400 MHz): 10.8 (br s, 1H, NH), 7.70 (dd, 1H, J=8.1, 1.8 Hz, H-6), 7.65 (d, 1H, J=1.7 Hz, H-4), 6.98 (d, 1H, J=8.1 Hz, H-7), 3.54-3.49 (m, 2H, $CH_2Cl$), 1.82-1.73 (m, 4H, 2×$CH_2$), 1.59 (quintet, 2H, J=7.2 Hz, $CH_2$), 1.15-1.00 (m, 1H), 1.00-0.85 (m, 1H), 0.52 (t, 3H, J=7.4 Hz, $CH_3$) ppm.
$^{13}$C-NMR (DMSO-$d_6$, TMS, 101 MHz): 181.0, 145.7, 137.6, 132.6, 126.6, 120.9, 109.1, 53.4, 45.1, 36.2, 32.3, 30.3, 21.5, 8.5 ppm.

Analysis for the Formula $C_{14}H_{19}ClN_2O_3S$ (330.84):
Calculated: C, 50.83; H, 5.79; N, 8.47; Cl, 10.72, S 9.69%.
Found: C, 50.79; H, 5.74; N, 8.51; Cl, 10.71, S 9.72%.

Process H (Coupling Reactions of ω-Chloroalkyl Compounds)

In the coupling reaction the appropriate chloroalkyl compound is coupled with the secondary amine. The melt of the base (12 mmoles) is heated to 180° C. under slow stirring, and a chloroalkyl compound (12 mmoles) and sodium carbonate (1.36 g; 12 mmoles) are measured to it at the same temperature. The mixture is allowed to react for 1 hour. The melt is then allowed to cool, ethyl acetate and water are added to it and the phases are separated. The organic phase is evaporated, and the residual oil is subjected to chromatography on a short column using ethyl acetate as eluent. The desired compounds are prepared as main products of the column chromatography.

Processing method 1 If the product purified by column chromatography gets crystalline upon trituration with diethyl ether, it is filtered off and recrystallized from the solvent indicated after the melting point of the given substance. The desired compounds are obtained in form of white crystals.

Processing method 2 If the basic product does not get crystalline upon the addition of diethyl ether, it is dissolved in 200 ml of ether, the slight amount of floating precipitate is filtered off, and to the pure solution a solution of the calculated amount (one molar equivalent) of hydrogen chloride in 50 ml of diethyl ether is added under vigorous stirring. The separated white salt is filtered, washed with ether and hexane and dried in a vacuum pistol at room temperature for 3 hours. If necessary, the hydrochloride salt is recrystallized.

Processing method 3 If the basic product does not get crystalline upon the addition of diethyl ether and does not provide a well-filterable salt with hydrogen chloride, it is dissolved in 100 ml of hot ethyl acetate, and a solution of 1 molar equivalent of oxalic acid dihydrate in 50 ml of hot ethyl acetate is dropped to it within 10 minutes, under stirring. The white oxalate salt gets separated upon cooling. It is filtered off at room temperature, washed with ethyl acetate and hexane and dried.

EXAMPLE 57

5-Chloro-3-{3-[4-(3-chlorophenyl)-piperazin-1-yl]-propyl}-3-ethyl-1,3-dihydro-2H-indol-2-one The title compound is prepared according to process H by applying processing method 1 starting from 5-chloro-3-(3-chloropropyl)-3-ethyl-1,3-dihydro-2H-indol-2-one and 2-chloro-6,7-dihydro-4H-tieno[3,2-c]pyridine.

M.p.: 117-119° C. (hexane-ethyl acetate).
IR (KBr): 3172 (NH), 1718 (C=O) $cm^{-1}$.
$^1$H-NMR (CDCl$_3$, TMS, 400 MHz): 0.65 (3H, t, J=7.4 Hz), 1.28-1.04 (1H, m), 1.40-1.24 (1H, m), 1.82-1.75 (2H, m), 2.00-1.89 (2H, m), 2.27 (2H, t, J=7.4 Hz), 2.41 (4H, t, J=5.0 Hz), 3.12 (4H, t, J=5.0 Hz), 6.73 (1H, dd, J=2.4, 8.4 Hz), 6.78 (1H,dd, J=1.7, 7.9 Hz), 6.82 (1H, t, J=2.2 Hz), 6.84 (1H, d, J=8.2 Hz), 7.10 (1H, d, J=2.0 Hz), 7.13 (1H, t, J=8.1 Hz), 7.19 (1H, dd, J=2.1, 8.2 Hz) 9.17 (1H, s) ppm.
$^{13}$C-NMR (CDCl$_3$, TMS, 101 MHz): 182.3, 152.2, 139.9, 134.9, 134.4, 129.9, 127.9, 127.7, 123.4, 119.2, 115.6, 113.7, 110.6, 58.1, 54.5, 52.9, 48.5, 35.1, 31.0, 21.6, 8.5 ppm.

Analysis for the Formula $C_{23}H_{27}Cl_2N_3O$ (432.40):
Calculated: C, 63.89; H, 6.29; Cl, 16.40; N, 9.72%.
Found: C, 63.50; H, 6.34; Cl, 16.00; N, 9.69%.

EXAMPLE 58

3-Ethyl-3-[3-(4-pyridin-2-yl-piperazin-1-yl)-propyl]-1,3-dihydro-2H-indol-2-one

The title compound is prepared according to process H by applying processing method 1 starting from 3-(3-chloropropyl)-3-ethyl-1,3-dihydro-2H-indol-2-one and 2-(pyridin-1-yl)-piperazine.

M.p.: 122-124° C. (hexane-ethyl acetate).
IR (KBr): 3194, 1710 (C=O) $cm^{-1}$.
$^1$H-NMR (CDCl$_3$, TMS, 400 MHz): 0.64 (3H, t, J=7.4 Hz), 1.28-1.23 (1H, m), 1.38-1.32 (1H, m), 1.80-1.78 (2H, m), 1.97-1.81 (2H, m), 2.26 (2H, t, J=7.5 Hz), 2.40 (4H, t, J=4.7 Hz), 3.49-3.44 (4H, m), 6.61-6.57 (2H, m), 6.90 (1H, d, J=7.7 Hz), 7.04 (1H, dt, J=1.0, 7.5 Hz), 7.12 (1H, d, J=6.4 Hz), 7.19 (1H, dt, J=1.3, 7.7 Hz), 7.44 (1H, dt, J=2.0, 7.9 Hz), 8.16 (1H, dd, J=1.9, 5.6 Hz), 9.02 (1H, s) ppm.
$^{13}$C-NMR (CDCl$_3$, TMS, 101 MHz): 182.6, 159.5, 147.8, 141.4, 137.3, 132.4, 127.6, 122.9, 122.3, 113.1, 109.6, 106.9, 58.4, 54.0, 52.9, 45.0, 35.2, 31.0, 21.5, 8.5 ppm.

Analysis for the Formula $C_{22}H_{28}N_4O$ (364.49):
Calculated: C, 72.50; H, 7.74; N, 15.37%.
Found: C, 72.23; H, 7.69; N, 15.28%.

EXAMPLE 59

5-Bromo-3-ethyl-3-[4-(4-pyridin-2-yl-piperazin-1-yl)-butyl]-1,3-dihydro-2H-indol-2-one The title compound is prepared according to process H by applying processing method 1 starting from 5-bromo-3-(4-chlorobutyl)-3-ethyl-1,3-dihydro-2H-indol-2-one and 2-(pyridin-1-yl)-piperazine.

M.p.: 114-115° C. (hexane-ethyl acetate).
IR (KBr): 3096, 1731 (C=O), 812 $cm^{-1}$.

¹H-NMR (CDCl₃, TMS, 400 MHz): 9.15 (1H, br s), 8.17 (1H, dd, J=1.6, 5.3 Hz), 7.46 (1H, dt, J=2.0, 7.8 Hz), 7.32 (1H, dd, J=1.9, 8.2 Hz), 7.22 (1H, d, J=1.9 Hz), 6.80 (1H, d, J=8.2 Hz), 6.64-6.60 (2H, m), 3.56 (4H, br s), 2.54 (4H, br s), 2.33 (2H, br s), 1.96-1.86 (2H, m), 1.79-1.71 (2H, m), 1.58-1.38 (2H, m), 1.18-1.03 (1H, m), 0.98-0.85 (1H, m), 0.63 (3H, t, J=7.4 Hz) ppm.

¹³C-NMR (CDCl₃, TMS, 101 MHz): 182.9, 159.2, 149.5, 147.9, 139.5, 137.5, 134.8, 126.1, 115.1, 113.4, 111.1, 107.1, 57.9, 54.5, 52.7, 44.7, 37.3, 31.0, 26.3, 22.1, 8.5 ppm.

Analysis for the Formula C₂₃H₂₉BrN₄O (457.42):
Calculated: C, 60.39; H, 6.39; Br, 17.47; N, 12.25%.
Found: C, 59.90; H, 6.38; Br, 17.24; N, 11.98%.

EXAMPLE 60

3-{4-[4-(3-Chlorophenyl)-piperazin-1-yl]-butyl}-3-ethyl-1,3-dihydro-2H-indol-2-one·H₂O—HCl-isopropanol (1:1:1:1)

The title compound is prepared according to process H by applying processing method 2 starting from 3-(4-chlorobutyl)-3-ethyl-1,3-di-hydro-2H-indol-2-one and 1-(3-chlorophenyl)-piperazine.

M.p.: 109-111° C.
IR (KBr): 1701 (C=O), 1180 cm⁻¹.
¹H-NMR (DMSO-d₆, TMS, 400 MHz): 11.14 (1H, br s), 10.44 (1H, s), 7.25 (1H, t, J=8.2 Hz), 7.22 (1H, d, J=7.9 Hz), 7.18 (1H, dt, J=1.2, 7.7 Hz), 7.03 (1H, t, J=2.1 Hz), 6.99 (1H, dt, J=0.9, 7.6 Hz), 6.94 (1H, dd, J=1.9, 8.3 Hz), 6.86 (1H, d, J=7.8 Hz), 6.86 (1H, d, J=7.9 Hz), 4.37 (1H, br s), 3.84 (2H, br s), 3.83-3.75 (1H, m), 3.5-3.3 (4H, br s), 3.21 (2H, t), 3.10-2.85 (4H, br s), 1-85-1.65 (4H, m), 1.65-1.55 (2H, m), 1.04 (2H, d, J=6.1 Hz), 1.01-0.94 (1H, m), 0.9-0.7 (1H, m), 0.51 (3H, t, J=7.3 Hz) ppm.

¹³C-NMR (DMSO-d₆, TMS, 101 MHz): 180.8, 151.0, 142.7, 134.1, 132.1, 130.8, 127.8, 123.2, 121.8, 119.3, 115.4, 114.3, 109.4, 62.2, 55.1, 53.2, 50.3, 44.9, 36.6, 30.3, 25.7, 23.2, 21.4, 8.6 ppm.

Analysis for the Formula C₂₇H₄₁Cl₂N₃O₃ (526.55):
Calculated: C, 61.59; H, 7.85; Cl, 13.47; N, 7.98%.
Found: C, 61.88; H, 7.58; Cl, 13.68; N, 8.05%.

EXAMPLE 61

5-Bromo-3-{4-[4-(3-chlorophenyl)-piperazin-1-yl]-butyl}-3-ethyl-1,3-dihydro-2H-indol-2-one monooxalate The title compound is prepared according to process H by applying processing method 3 starting from 5-bromo-3-(4-chlorobutyl)-3-ethyl-1,3-dihydro-2H-indol-2-one and 1-(3-chloro-phenyl)-piperazine.

M.p.: 200-202° C.
IR (KBr): 3200, 1706 (C=O) cm⁻¹.
¹H-NMR (DMSO-d₆, TMS, 400 MHz): 10.5 (1H, s), kb. 7.8 (2H, br s), 7.45 (1H, d, J=2.0 Hz), 7.35 (1H, dd, J=1.8, 8.2 Hz), 7.23 (1H, t, J=8.1 Hz), 7.00 (1H, t, J=2.1 Hz), 6.92 (1H, dd, J=2.2, 8.0 Hz), 6.83 (1H, dd, J=1.8, 8.2 Hz), 6.81 (1H, d, J=8.2 Hz), 3.36 (4H, br s), 3.04 (4H, br s), 2.80 (2H, t, J=8.1 Hz), 1.85-1.66 (4H, m), 1.54-1.48 (2H, m), 0.97-0.89 (1H, m), 0.84-0.77 (1H, m), 0.50 (3H, t, J=7.3 Hz) ppm.

¹³C-NMR (DMSO-d₆, TMS, 101 MHz): 180.4, 164.2, 151.9, 142.0, 134.1, 134.0, 130.7, 130.5, 126.2, 119.1, 115.2, 114.2, 113.7, 111.3, 55.0, 53.6, 50.9, 45.6, 36.5, 30.2, 23.9, 21.5, 8.5 ppm.

Analysis for the Formula C₂₆H₃₁BrClN₃O₅ (580.91):
Calculated: C, 53.76; H, 5.38; N, 7.23%.
Found: C, 53.89; H, 5.60; N, 7.11%.

EXAMPLE 62

3-Isobutyl-3-[4-(4-pyridin-2-yl-piperazin-1-yl)-butyl]-1,3-dihydro-2H-indol-2-one The title compound is prepared according to process H by applying processing method 1 starting from 3-(4-chlorobutyl)-3-ethyl-1,3-dihydro-2H-indol-2-one and 2-(pyridin-1-yl)-piperazine.

M.p.: 158-159° C. (hexane-ethyl acetate).
IR (KBr): 3192, 1719 (C=O) cm⁻¹.
¹H-NMR (CDCl₃, TMS, 400 MHz): 9.03 (1H, s), 8.17 (1H, ddd, J=1.0, 1.9, 4.8 Hz), 7.44 (1H, dt, J=2.0 7.9 Hz), 7.19 (1H, dt, J=1.3, 7.6 Hz), 7.10 (1H, d, J=6.8 Hz), 7.03 (1H, dt, J=0.9, 7.4 Hz), 6.90 (1H, d, J=7.7 Hz), 6.60 (1H, dd, J=0.7.7.4 Hz), 6.60 (dt, J=0.7, 7.0 Hz), 3.48 (4H, t, J=5.2 Hz), 2.44 (4H, t, J=5.1 Hz), 2.21 (2H, t, J=7.8 Hz), 1.86-1.82 (2H, m), 1.80-1.66 (2H, m), 1.50-1.28 (3H, m), 1.16-1.14 (1H, m), 0.92.0.80 (1H, m), 0.69 (3H, d, J=6.7 Hz), 0.58 (3H, d, J=6.7 Hz) ppm.

¹³C-NMR (CDCl₃, TMS, 101 MHz): 183.2, 159.5, 147.9, 141.2, 137.3, 132.0, 127.5, 123.3, 122.2, 113.2, 109.6, 107.0, 58.3, 53.1, 52.9, 46.3, 45.1, 39.9, 26.8, 25.3, 24.2, 23.1, 21.6 ppm.

Analysis for the Formula C₂₅H₃₄N₄O (406.58):
Calculated: C, 73.86; H, 8.43; N, 13.78%.
Found: C, 73.39; H, 8.34; N, 13.50%.

EXAMPLE 63

3-{4-[4-(2,3-Dihydrobenzo[1,4]dioxin-5-yl)-piperazin-1-yl]-butyl}-3-ethyl-1,3-dihydro-2H-indol-2-one The title compound is prepared according to process H by applying processing method 1 starting from 3-(4-chlorobutyl)-3-ethyl-1,3-dihydro-2H-indol-2-one and 4-(2,3-dihydrobenzo[1,4]dioxin-5-yl)-piperazine.

M.p.: 169-170° C. (hexane-ethyl acetate).
IR (KBr): 3025, 1710 (C=O) cm⁻¹.
¹H-NMR (CDCl₃, TMS, 400 MHz): 0.63 (3H, t, J=7.3 Hz), 0.92-0.89 (1H, m), 1.13-1.09 (1H, m), 1.49-1.42 (2H, m), 1.82-1.74 (2H, m), 1.95-1.87 (2H, m), 2.30 (2H, t, J=7.9 Hz), 2.61 (4H, br s), 3.07 (4H, br s), 4.24-4.21 (2H, m), 4.31-4.27 (4H, m), 6.50 (1H, dd, J=1.4, 8.0 Hz), 6.58 (1H, dd, J=1.4, 8.2 Hz), 6.75 (1H, 1H, t, J=8.1 Hz), 6.89 (1H, d, J=7.7 Hz), 7.04 (1H, dt, J=0.9, 7.4 Hz), 7.11 (1H, d, J=6.7 Hz), 7.19 (1H, dt, J=1.3, 7.6 Hz), 8.80 (1H, s) ppm.

¹³C-NMR (CDCl₃, TMS, 101 MHz): 182.4, 144.0, 141.5, 141.4, 136.4, 132.5, 127.6, 123.0, 122.3, 120.6, 111.9, 110.7, 109.5, 64.3, 63.9, 58.2, 54.1, 53.1, 50.3, 37.5, 31.0, 26.6, 22.2, 8.5 ppm.

Analysis for the Formula C₂₆H₃₃N₃O₃ (435.57):
Calculated: C, 71.70; H, 7.64; N, 9.65%.
Found: C, 71.50; H, 7.60; N, 9.60%.

EXAMPLE 64

3-{4-[4-(2,3-Dihydrobenzo[1,4]dioxin-5-yl)-piperazin-1-yl]-butyl}-3-isobutyl-1,3-dihydro-2H-indol-2-one The title compound is prepared according to process H by applying processing method 1 starting from 3-(4-chlorobutyl)-3-isobutyl-1,3-dihydro-2H-indol-2-one and 4-(2,3-dihydro-benzo[1,4]dioxin-5-yl)-piperazine.

M.p.: 152-154° C. (hexane-ethyl acetate).

IR (KBr): 3331, 3081, 1706 (C=O) cm$^{-1}$.

$^1$H-NMR (CDCl$_3$, TMS, 400 MHz): 0.61 (3H, d, J=6.7 Hz), 0.72 (3H, d, J=6.7 Hz), 0.89-0.83 (1H, m), 1.11-1.06 (1H, m), 1.33 (1H, m), 1.47-1.38 (2H, m), 1.79-1.67 (2H, m), 1.93-1.84 (2H, m), 2.29 (2H, t, J=7.9 Hz), 2.61 (4H, br s), 3.07 (4H, br s), 4.24-4.21 (2H, m), 4.31-4.27 (4H, m), 6.51 (1H, dd, J=1.4, 8.1 Hz), 6.58 (1H, dd, J=1.4, 8.2 Hz), 6.75 (1H, 1H, t, J=8.2 Hz), 6.89 (1H, d, J=7.7 Hz), 7.03 (1H, dt, J=0.8, 7.4 Hz), 7.10 (1H, d, J=6.9 Hz), 7.19 (1H, dt, J=1.3, 7.6 Hz), 8.88 (1H, s) ppm.

$^{13}$C-NMR (CDCl$_3$, TMS, 101 MHz): 182.9, 144.0, 141.5, 141.2, 136.4, 132.8, 127.5, 123.3, 122.2, 120.6, 111.9, 110.7, 109.6, 64.3, 63.9, 58.2, 53.1, 53.0, 50.3, 46.3, 39.9, 26.6, 25.3, 24.2, 23.1, 21.6 ppm.

Analysis for the Formula C$_{28}$H$_{37}$N$_3$O$_3$ (463.63):

Calculated: C, 72.54; H, 8.04; N, 9.06%.

Found: C, 72.53; H, 8.00; N, 9.02%.

EXAMPLE 65

5,7-Dichloro-3-ethyl-3-[4-(4-pyridin-2-yl-piperazin-1-yl)-butyl]-1,3-dihydro-2H-indol-2-one The title compound is prepared according to process H by applying processing method 1 starting from 5,7-dichloro-3-(4-chlorobutyl)-3-ethyl-1,3-dihydro-2H-indol-2-one and 2-(pyridin-1-yl)-piperazine.

M.p.: 144-146° C. (hexane-ethyl acetate).

IR (KBr): 3081, 1737 (C=O), 772 cm$^{-1}$.

$^1$H-NMR (CDCl$_3$, TMS, 400 MHz): 0.65 (3H, t, J=7.4 Hz), 0.98-0.86 (1H, m), 1.18-1.04 (1H, m), 1.48-1.38 (2H, m), 1.80-1.70 (2H, m), 2.00-1.90 (2H, m), 2.26 (2H, t, J=7.7 Hz), 2.48 (4H, t, J=5.1 Hz), 3.50 (4H, t, J=5.1 Hz), 6.62-6.58 (2H, m), 7.00 (1H, d, J=1.9 Hz), 7.22 (1H, d, J=1.9 Hz), 7.45 (1H, dt, J=2.0, 7.9 Hz), 8.17 (1H, ddd, J=0.9, 1.9, 4.9 Hz), 8.79 (1H, s) ppm.

$^{13}$C-NMR (CDCl$_3$, TMS, 101 MHz): 180.8, 159.5, 147.9, 137.9, 137.3, 135.4, 128.0, 127.5, 121.9, 115.1, 113.2, 107.0, 58.0, 55.6, 52.9, 45.0, 37.4, 31.0, 26.6, 22.2, 8.5 ppm.

Analysis for the Formula C$_{23}$H$_{28}$Cl$_2$N$_{40}$ (447.41):

Calculated: C, 61.75; H, 6.31; Cl, 15.85; N, 12.52%.

Found: C, 62.14; H, 6.34; Cl, 15.74; N, 12.21%.

EXAMPLE 66

5-Chloro-3-ethyl-3-[4-(4-pyridin-2-yl-piperazin-1-yl)-butyl]-1,3-dihydro-2H-indol-2-one The title compound is prepared according to process H by applying processing method 1 starting from 5-chloro-3-(4-chlorobutyl)-3-ethyl-1,3-dihydro-2H-indol-2-one and 2-(pyridin-1-yl)-piperazine.

M.p.: 154-156° C. (hexane-ethyl acetate).

IR (KBr): 3157, 1729 (C=O), 1597, 775 cm$^{-1}$.

$^1$H-NMR (CDCl$_3$, TMS, 40 MHz): 0.63 (3H, t, J=7.4 Hz), 0.98-0.85 (1H, m), 1.18-1.04 (1H, m), 1.53-1.35 (2H, m), 1.83-1.70 (2H, m), 1.96-1.86 (2H, m), 2.25 (2H, t, J=7.6 Hz), 2.47 (4H, t, J=5.1 Hz), 3.49 (4H, t, J=5.1 Hz), 6.62-6.58 (2H, m), 6.83 (1H, d, J=8.2 Hz), 7.09 (1H, d, J=2.1 Hz), 7.17 (1H, dd, J=2.1, 8.2 Hz), 7.45 (1H, dt, J=2.0, 7.9 Hz), 8.17 (1H, dm, J=4.7 Hz), 9.13 (1H, s) ppm.

$^{13}$C-NMR (CDCl$_3$, TMS, 101 MHz): 182.3, 159.5, 147.9, 140.0, 137.4, 127.7, 127.6, 123.4, 113.2, 110.5, 107.0, 58.1, 54.6, 52.9, 45.1, 37.4, 31.0, 26.8, 22.2, 8.5 ppm.

Analysis for the Formula C$_{23}$H$_{29}$ClN$_4$O (412.97):

Calculated: C, 66.90; H, 7.08; Cl, 8.58; N, 13.57%.

Found: C, 66.22; H, 7.04; Cl, 8.33; N, 13.27%.

EXAMPLE 67

5-Chloro-3-{4-[4-(3-chlorophenyl)-piperazin-1-yl]-butyl}-3-ethyl-1,3-dihydro-2H-indol-2-one The title compound is prepared according to process H by applying processing method 1 starting from 5-chloro-3-(4-chlorobutyl)-3-ethyl-1,3-dihydro-2H-indol-2-one and 6,7-dihydro-4H-tieno[3,2-c]pyridine.

M.p.: 139-142° C. (hexane-ethyl acetate).

IR (KBr): 3412, 1712 (C=O), 780 cm$^{-1}$.

$^1$H-NMR (CDCl$_3$, TMS, 400 MHz): 0.64 (3H, t, J=7.4 Hz), 0.95-0.88 (1H, m), 1.13-1.07 (1H, m), 1.45-1.36 (2H, m), 1.80-1.71 (2H, m), 1.96-1.88 (2H, m), 2.24 (2H, t, J=7.5 Hz), 2.48 (4H, t, J=5.0 Hz), 3.13 (4H, t, J=5.0 Hz), 6.73 (1H, ddd, J=0.5, 2.3, 8.4 Hz), 6.78 (1H, ddd, J=0.6, 1.8, 7.8 Hz), 6.84 (1H, d, J=8.0 Hz), 6.84 (1H, t, J=2.1 Hz), 7.09 (1H, d, J=2.1 Hz), 7.13 (1H, t, J=8.2 Hz), 7.18 (1H, dd, J=2.1, 8.2 Hz) ppm.

$^{13}$C-NMR (CDCl$_3$, TMS, 101 MHz): 182.4, 152.3, 140.0, 134.8, 134.5, 129.9, 127.8, 127.6, 123.4, 119.1, 115.6, 113.7, 110.6, 57.9, 54.7, 52.9, 48.5, 37.4, 31.0, 26.8, 22.1, 8.5 ppm.

Analysis for the Formula C$_{24}$H$_{29}$Cl$_2$N$_3$O (446.42):

Calculated: C, 64.57; H, 6.55; Cl, 15.88; N, 9.41%.

Found: C, 64.55; H, 6.53; Cl, 15.75; N, 9.40%.

EXAMPLE 68

3-[4-(4-Phenylpiperazin-1-yl)-butyl]-3-ethyl-1,3-dihydro-2H-indol-2-one monooxalate The title compound is prepared according to process H by applying processing method 3 starting from 3-(4-chlorobutyl)-3-ethyl-1,3-dihydro-2H-indol-2-one and 1-phenylpiperazine.

M.p.: 121-123° C.

IR (KBr): 3245, 1710, 1620 (C=O) cm$^{-1}$.

$^1$H-NMR (DMSO-d$_6$, TMS, 400 MHz): 10.77 (2H, br s), 10.46 (1H, s), 7.30-7.16 (4H, m), 7.02-6.91 (3H, m), 6.89 (1H, d, J=7.7 Hz), 6.84 (1H, t, J=7.3 Hz), 3.37 (4H, br s), 3.20 (4H, br s), 2.93, 2.90 (2H, d, J=6.0 Hz), 2.0-1.72 (4H, m), 1.56 (2H, m), 0.98 (1H, m), 0.83 (1H, m), 0.51 (3H, t, J=7.3 Hz) ppm.

$^{13}$C-NMR (DMSO-d$_6$, TMS, 101 MHz): 180.9, 149.9, 142.7, 132.2, 129.3, 127.6, 123.2, 121.8, 120.1, 116.1, 109.4, 55.4, 53.2, 50.8, 45.7, 36.8, 30.4, 23.5, 21.5, 8.6 ppm.

Analysis for the Formula C$_{26}$H$_{33}$N$_3$O$_5$ (467.57):

Calculated: C, 66.79; H, 7.11; N, 8.99%.

Found: C, 65.09; H, 7.21; N, 8.73%.

EXAMPLE 69

3-Ethyl-3-{4-[4-(2-methoxyphenyl)-piperazin-1-yl]-butyl}-1,3-dihydro-2H-indol-2-one monooxalate The title compound is prepared according to process H by applying processing method 3 starting from 3-(4-chlorobutyl)-3-ethyl-1,3-di-hydro-2H-indol-2-one and 1-(2-methoxyphenyl)-piperazine.

M.p.: 180-183° C.

IR (KBr): 3201, 1707 (C=O) cm$^{-1}$.

$^1$H-NMR (DMSO-d$_6$, TMS, 400 MHz): 10.4 (1H, br s), 9.1 (2H, br s), 7.21 (1H, d, J=7.9 Hz), 7.18 (1H, dt, J=7.7, 1.1 Hz), 7.02-6.94 (3H, m), 6.91-6.87 (2H, m), 6.86 (1H, d, J=7.7 Hz), 3.78 (3H, s), 3.15 (8H, br s), 2.88 (2H, t, J=7.8 Hz), 1.78-1.68 (4H, m), 1.53 (2H, m), 0.99-0.94 (1H, m), 0.83-0.77 (1H, m), 0.51 (3H, t, J=7.3 Hz) ppm.

$^{13}$C-NMR (DMSO-d$_6$, TMS, 101 MHz): 180.8, 164.6, 152.0, 142.7, 139.8, 132.2, 127.8, 123.5, 123.2, 121.7, 121.0, 118.4, 112.1, 109.3, 55.5, 55.5, 53.2, 51.4, 47.4, 36.6, 30.4, 23.7, 21.5, 8.6 ppm.

Analysis for the Formula C$_{27}$H$_{35}$N$_3$O$_6$ (497.60):
Calculated: C, 65.17; H, 7.09; N, 8.44%.
Found: C, 65.10; H, 7.07; N, 8.46%.

EXAMPLE 70

3-Ethyl-3-[4-(4-pyrimidin-2-yl-piperazin-1-yl)-butyl]-1,3-dihydro-2H-indol-2-one monooxalate The title compound is prepared according to process H by applying processing method 3 starting from 3-(4-chlorobutyl)-3-ethyl-1,3-dihydro-2H-indol-2-one and 4-(pyrimidin-2-yl)-piperazine.

M.p.: 132-134° C.
IR (KBr): 3200, 1700, 1622, 1198 cm$^{-1}$.
$^1$H-NMR (DMSO-d$_6$, TMS, 400 MHz): 10.4 (1H, s), 8.42 (2H, d, J=4.8 Hz), 8.4 (2H, br s), 7.20 (1H, d, J=7.7 Hz), 7.17 (1H, dt, J=1.1, 7.6 Hz), 6.99 (1H, dt, J=0.8, 7.5 Hz), 6.86 (1H, d, J=7.7 Hz), 3.92 (4H, br s), 3.05 (4H, br s), 2.82 (2H, t, J=8.0 Hz), 1.79-1.67 (4H, m), 1.53 (2H, m), 0.98-0.95 (1H, m), 0.82-0.78 (1H, m), 0.50 (3H, t, J=7.4 Hz) ppm.

$^{13}$C-NMR (DMSO-d$_6$, TMS, 101 MHz): 180.9, 164.5, 142.7, 132.2, 127.8, 123.2, 121.7, 109.4, 55.7, 53.2, 50.8, 40.9, 36.6, 30.4, 23.8, 21.5, 8.6 ppm.

Analysis for the Formula C$_{24}$H$_{31}$N$_5$O$_5$ (469.55):
Calculated: C, 61.39; H, 6.65; N, 14.92%.
Found: C, 61.38; H, 6.61; N, 14.84%.

EXAMPLE 71

3-Ethyl-3-[4-(4-pyridin-2-yl-piperazin-1-yl)-butyl]-1,3-dihydro-2H-indol-2-one

The title compound is prepared according to process H by applying processing method 1 starting from 3-(4-chlorobutyl)-3-ethyl-1,3-dihydro-2H-indol-2-one and 2-(pyridin-1-yl)-piperazine.

M.p.: 131-133° C. (hexane-ethyl acetate).
IR (KBr): 3237, 1720 (C=O), 1691 cm$^{-1}$.
$^1$H-NMR (CDCl$_3$, TMS, 400 MHz): 8.88 (1H, s), 8.17 (1H, dd, J=1.9, 5.4 Hz), 7.46 (1H, dt, J=2.0, 7.9 Hz), 7.19 (1H, dt, J=1.4, 7.6 Hz), 7.11 (1H, d, J=7.4 Hz), 7.04 (1H, dt, J=0.9, 7.4 Hz), 6.91 (1H, d, J=7.7 Hz), 6.62 (1H, d, J=7.2 Hz), 6.61 (1H, d, J=7.9 Hz), 3.56 (4H, t, J=4.2 Hz), 2.55 (4H, br s), 2.31 (2H, t, J=7.8 Hz), 1.97-1.87 (2H, m), 1.83-1.74 (2H, m), 1.53-1.44 (2H, m), 1.14-1.08 (1H, m), 0.95-0.89 (1H, m), 0.63 (3H, t, J=7.4 Hz) ppm.

$^{13}$C-NMR (CDCl$_3$, TMS, 101 MHz): 182.5, 159.3, 147.9, 141.4, 137.4, 132.4, 127.6, 123.0, 122.3, 113.4, 109.6, 107.0, 58.1, 54.1, 52.7, 44.7, 37.4, 31.0, 26.4, 22.2, 8.5 ppm.

Analysis for the Formula C$_{23}$H$_{30}$N$_4$O (378.52):
Calculated: C, 72.98; H, 7.99; N, 14.80%.
Found: C, 72.66; H, 8.01; N, 14.67%.

EXAMPLE 72

3-{4-[4-(3-Chlorophenyl)-piperazin-1-yl]-butyl}-3-ethyl-1,3-dihydro-2H-indol-2-one 5-sulfonamide monooxalate The title compound is prepared according to process H by applying processing method 3 starting from 3-(4-chlorobutyl)-3-ethyl-2-oxo-indoline 5-sulfonamide and 2-(pyridin-1-yl)-piperazine.

M.p.: 188-190° C.
IR (KBr): 3352, 1720 (C=O), 1319, 1161 cm$^{-1}$.
$^1$H-NMR (DMSO-d$_6$, TMS, 400 MHz): 0.53 (3H, t, J=7.4 Hz), 0.90-0.76 (1H, m), 1.04-0.90 (1H, m), 1.60-1.46 (2H, m), 1.86-1.70 (4H, m), 2.82 (2H, t, J=7.8 Hz), 3.06 (4H, br s), 3.37 (4H, br s), 6.84 (1H, dd, J=1.2, 7.8 Hz), 6.92 (1H, dd, J=1.8, 8.4 Hz), 7.00 (1H, t, J=2.1 Hz), 7.01 (1H, d, J=7.9 Hz), 7.24 (1H, t, J=8.1 Hz), 7.67 (1H, d, J=1.7 Hz), 7.70 (1H, dd, J=1.8, 8.2 Hz), 8.0-6.8 (4H, br s), 10.84 (1H, s) ppm.

$^{13}$C-NMR (DMSO-d$_6$, TMS, 101 MHz): 181.0, 164.3, 151.3, 145.8, 137.6, 134.1, 132.5, 130.7, 126.6, 120.9, 119.1, 115.3, 114.2, 109.2, 55.6, 53.4, 50.9, 45.5, 36.4, 30.2, 23.9, 21.5, 8.5 ppm.

Analysis for the Formula C$_{26}$H$_{33}$ClN$_4$O$_7$S (581.09):
Calculated: C, 53.74; H, 5.72; Cl, 6.10; N, 9.64, S 5.52%.
Found: C, 53.38; H, 5.67; Cl, 6.06; N, 9.41, S 5.33%.

EXAMPLE 73

3-{4-[4-(4-Chlorophenyl)-piperazin-1-yl]-butyl}-3-ethyl-5-methyl-1,3-dihydro-2H-indol-2-one The title compound is prepared according to process H by applying processing method 1 starting from 3-(4-chlorobutyl)-3-ethyl-5-methyl-1,3-dihydro-2H-indol-2-one and 1-(4-chloro-phenyl)-piperazine.

M.p.: 175-177° C. (ethyl acetate).
IR (KBr): 3171, 1712 (C=O), 815 cm$^{-1}$.
$^1$H-NMR (CDCl$_3$, TMS, 400 MHz): 0.62 (3H, t, J=7.4 Hz), 0.90-0.85 (1H, m), 1.20-0.90 (1H, m), 1.50-1.30 (2H,m), 1.94-1.73 (4H, m), 2.24 (2H, t, J=7.8 Hz), 2.34 (3H, s), 2.49 (4H, t, J=5.0 Hz), 3.10 (4H, t, J=5.0 Hz), 6.78 (1H, d, J=7.9 Hz), 6.79 (2H, d, J=9.1 Hz), 6.92 (1H, d, J=0.6 Hz), 6.99 (1H, d, J=7.9 Hz), 7.18 (2H, d, J=9.1 Hz), 8.45 (1H, s) ppm.

$^{13}$C-NMR (CDCl$_3$, TMS, 101 MHz): 182.8, 149.8, 139.0, 132.6, 131.6, 128.8, 127.8, 124.3, 123.6, 117.0, 109.2, 58.1, 54.2, 52.9, 48.9, 37.5, 31.0, 26.9, 22.2, 21.2, 8.5 ppm.

Analysis for the Formula C$_{25}$H$_{32}$ClN$_3$O (426.01):
Calculated: C, 70.49; H, 7.57; Cl, 8.32; N, 9.86%.
Found: C, 70.16; H, 7.34; Cl, 8.16; N, 9.61%.

EXAMPLE 74

3-Ethyl-3-{4-[4-(4-methoxyphenyl)-piperazin-1-yl]-butyl}-1,3-dihydro-2H-indol-2-one The title compound is prepared according to process H by applying processing method 1 starting from 3-(4-chlorobutyl)-3-ethyl-1,3-dihydro-2H-indol-2-one and 1-(4-methoxyphenyl)-piperazine.

M.p.: 109-110° C. (hexane-ethyl acetate).
IR (KBr): 3172, 1713 (C=O) cm$^{-1}$.
$^1$H-NMR (CDCl$_3$, TMS, 400 MHz): 0.63 (3H, t, J=7.4 Hz), 0.96-0.86 (1H, m), 1.18-1.06 (1H, m), 1.49-1.34 (2H, m), 1.84-1.74 (2H, m), 1.97-1.88 (2H, m), 2.24 (2H, t, J=7.8 Hz), 2.51 (4H, t, J=4.9 Hz), 3.04 (4H, t, J=4.9 Hz), 3.76 (3H, s), 6.91-6.79 (5H, m), 7.05 (1H, dt, J=0.9, 7.4 Hz), 7.12 (1H, dd, J=0.6, 7.4 Hz), 7.20 (1H, dt, J=1.4, 7.7 Hz), 8.23 (1H, s) ppm.

$^{13}$C-NMR (CDCl$_3$, TMS, 101 MHz): 182.2, 153.7, 145.7, 141.4, 132.6, 127.6, 123.1, 122.4, 118.1, 114.4, 109.4, 58.3, 55.5, 54.1, 53.2, 50.5, 37.6, 31.1, 27.0, 22.3, 8.5 ppm.

Analysis for the Formula C$_{25}$H$_{33}$N$_3$O$_2$ (407.56):
Calculated: C, 73.68; H, 8.16; N, 10.31%.
Found: C, 72.89; H, 8.27; N, 10.14%.

EXAMPLE 75

3-{4-[4-(3-Chlorophenyl)-piperazin-1-yl]-butyl}-3-isobutyl-1,3-dihydro-2H-indol-2-one monohydrochloride The title compound is prepared according to process H by applying processing method 2 starting from 3-(4-chlorobutyl)-3-isobutyl-1,3-dihydro-2H-indol-2-one and 1-(3-chlorophenyl)-piperazine.

M.p.: 214-216° C.

IR (KBr): 3166, 2411, 1701 (C=O) cm$^{-1}$.

$^1$H-NMR (DMSO-d$_6$, TMS, 400 MHz): 0.56 (3H, d, J=6.7 Hz), 0.67 (3H, d, J=6.7 Hz), 0.79-0.72 (1H, m), 1.03-0.91 (1H, m), 1.25-1.15 (1H, m), 1.80-1.55 (6H, m), 2.94 (4H, br s), 3.18 (2H, d, J=11.9 Hz), 3.44-3.35 (4H, m), 6.86 (1H, d, J=7.9 Hz), 6.86 (1H, dd, J=2.0, 7.8 Hz), 6.93 (1H, dd, J=1.9, 8.4 Hz), 6.98 (1H, dt, J=0.9, 7.5 Hz), 7.03 (1H, t, J=2.1 Hz), 7.17 (1H, dt, J=1.2, 7.7 Hz), 7.22 (1H, d, J=7.7 Hz), 7.25 (1H, t, J=8.1 Hz), 10.4 (1H, s), 11.1 (1H, br s) ppm.

$^{13}$C-NMR (DMSO-d$_6$, TMS, 101 MHz): 181.2, 151.0, 142.4, 134.1, 132.4, 130.8, 127.7, 123.5, 121.6, 119.3, 115.4, 114.3, 109.4, 55.0, 52.1, 50.3, 45.7, 44.9, 38.9, 25.7, 25.1, 24.2, 23.2, 20.8 ppm.

Analysis for the Formula C$_{26}$H$_{35}$Cl$_2$N$_3$O (476.49):
Calculated: C, 65.54; H, 7.40; Cl, 14.88; N, 8.82%.
Found: C, 65.05; H, 7.35; Cl, 14.45; N, 8.65%.

EXAMPLE 76

3-{4-[4-(4-Chlorophenyl)-piperazin-1-yl]-butyl}-3-ethyl-1,3-dihydro-2H-indol-2-one The title compound is prepared according to process H by applying processing method 1 starting from 3-(4-chlorobutyl)-3-ethyl-1,3-dihydro-2H-indol-2-one and 1-(4-chlorophenyl)-piperazine.

M.p.: 145-146° C. (hexane-ethyl acetate).

IR (KBr): 3163, 1712 (C=O) cm$^{-1}$.

$^1$H-NMR (CDCl$_3$, TMS, 400 MHz): 0.63 (3H, t, J=7.4 Hz), 0.98-0.84 (1H, m), 1.18-1.06 (1H, m), 1.50-1.36 (2H, m), 1.96-1.73 (4H, m), 2.24 (2H, t, J=7.8 Hz), 2.49 (4H, t, J=5.0 Hz), 3.10 (4H, t, J=5.0 Hz), 6.80 (2H, d, J=9.0 Hz), 6.88 (1H, dt, J=0.7, 7.7 Hz), 7.05 (1H, dt, J=1.0, 7.5 Hz), 7.12 (1H, dt, J=0.7, 7.4 Hz), 7.18 (2H, d, J=9.2 Hz), 7.20 (1H, dt, J=1.4, 7.6 Hz), 7.92 (1H, s) ppm.

$^{13}$C-NMR (CDCl$_3$, TMS, 101 MHz): 182.6, 149.9, 141.3, 132.6, 128.9, 127.6, 124.4, 123.0, 122.3, 117.1, 109.5, 58.1, 54.2, 52.9, 49.0, 37.5, 31.0, 26.9, 22.2, 8.5 ppm.

Analysis for the Formula C$_{24}$H$_{30}$ClN$_3$O (411.98):
Calculated: C, 69.97; H, 7.34; Cl, 8.61; N, 10.20%.
Found: C, 69.49; H, 7.37; Cl, 8.63; N, 10.06%.

EXAMPLE 77

3-{4-[4-(3-Chlorophenyl)-piperazin-1-yl]-butyl}-3-ethyl-6-fluoro-1,3-dihydro-2H-indol-2-one The title compound is prepared according to process H by applying processing method 1 starting from 3-(4-chlorobutyl)-3-ethyl-6-fluoro-1,3-dihydro-2H-indol-2-one and 1-(3-chloro-phenyl)-piperazine.

M.p.: 116-117° C. (hexane-ethyl acetate).

IR (KBr): 3163, 1717 (C=O) cm$^{-1}$.

$^1$H-NMR (CDCl$_3$, TMS, 400 MHz): 0.62 (3H, t, J=7.4 Hz), 0.98-0.84 (1H, m), 1.16-1.04 (1H, m), 1.50-1.34 (2H, m), 1.80-1.72 (2H, m), 1.95-1.87 (2H, iii), 2.24 (2H, t, J=7.8 Hz), 2.48 (4H, t, J=5.0 Hz), 3.13 (4H, t, J=5.0 Hz), 6.67 (1H, dd, J=2.3, 8.8 Hz), 6.76-6.70 (2H, m), 6.78 (1H, ddd, J=0.8, 1.9, 8.0 Hz), 6.83 (1H, t. J=2.1 Hz), 7.03 (1H, dd, J=5.4, 8.1 Hz), 7.13 (1H, t, J=8.0 Hz) ppm.

$^{13}$C-NMR (CDCl$_3$, TMS, 101 MHz): 8.5, 22.2, 26.8, 31.0, 37.5, 48.5, 52.9, 53.9, 58.1, 98.3 (d, J=26.7 Hz), 108.6 (d, J=22.1 Hz), 113.7, 115.6, 119.1, 123.8 (d, J=9.5 Hz), 127.8 (d, J=3.1 Hz), 129.9, 134.8, 142.6 (d, J=11.8 Hz), 152.2, 162.4 (d, J=244.1 Hz) ppm.

Analysis for the Formula C$_{24}$H$_{29}$ClFN$_3$O (429.97):
Calculated: C, 67.04; H, 6.80; Cl, 8.25; N, 9.77%.
Found: C, 66.97; H, 6.86; Cl, 8.18; N, 9.74%.

EXAMPLE 78

3-{4-[4-(3-Chlorophenyl)-piperazin-1-yl]-butyl}-3-ethyl-5-methyl-1,3-dihydro-2H-indol-2-one The title compound is prepared according to process H by applying processing method 1 starting from 3-(4-chlorobutyl)-3-ethyl-5-methyl-1,3-dihydro-2H-indol-2-one and 1-(3-chloro-phenyl)-piperazine.

M.p.: 142-144° C. (hexane-ethyl acetate).

IR (KBr): 3178, 1714 (C=O) cm$^{-1}$.

$^1$H-NMR (CDCl$_3$, TMS, 400 MHz): 0.63 (3H, t, J=7.4 Hz), 0.98-0.86 (1H, m), 1.16-1.04 (1H, m), 1.32-1.50 (2H, m), 1.80-1.70 (2H, m), 1.96-1.86 (2H, m), 2.24 (2H, t, J=7.8 Hz), 2.34 (3H, s), 2.48 (4H, t, J=5.0 Hz), 3.13 (4H, t, J=5.0 Hz), 6.74 (1H, dd, J=2.1, 8.3 Hz), 6.78 (1H, dd, J=2.5, 7.9 Hz, 6.78 (1H, d, J=7.9 Hz), 6.84 (1H, t, J=2.1 Hz), 6.92 (1H, s), 6.99 (1H, d, J=7.8 Hz), 7.13 (1H, t, J=8.1 Hz), 8.26 (1H, s) ppm.

$^{13}$C-NMR (CDCl$_3$, TMS, 101 MHz): 182.3, 152.3, 138.8, 134.9, 132.6, 131.8, 129.9, 127.9, 123.8, 119.1, 115.6, 113.7, 109.1, 58.1, 54.2, 52.9, 48.5, 37.6, 31.1, 26.9, 22.3, 21.2, 8.6 ppm.

Analysis for the Formula C$_{25}$H$_{32}$ClN$_3$O (426.01):
Calculated: C, 70.49; H, 7.57; Cl, 8.32; N, 9.86%.
Found: C, 70.37; H, 7.56; Cl, 8.26; N, 9.79%.

EXAMPLE 79

5,7-Dichloro-3-[4-[4-(3-chlorophenyl)-piperazin-1-yl]-butyl]-3-ethyl-1,3-dihydro-2H-indol-2-one The title compound is prepared according to process H by applying processing method 1 starting from 5,7-dichloro-3-(4-chlorobutyl)-3-ethyl-1,3-dihydro-2H-indol-2-one and 1-(3-chloro-phenyl)-piperazine.

M.p.: 182-183° C. (etanol)

IR (KBr): 3100, 1732 (C=O), 744 cm$^{-1}$.

$^1$H-NMR (DMSO-d$_6$, TMS, 400 MHz): 0.52 (3H, t, J=7.3 Hz), 0.88-0.75 (1H, m), 0.98-0.90 (1H, m), 1.40-1.20 (2H, m), 1.85-1.70 (4H, m), 2.20-2.09 (2H, m), 2.37 (4H, t, J=4.6 Hz), 3.09 (4H, t, J=4.6 Hz), 6.76 (1H, dd, J=1.3, 7.8 Z), 6.85 (1H, dd, J=1.8, 8.3 Hz), 6.89 (1H, t, J=2.0 Hz), 7-19 (1H, t, J=8.1 Hz), 7.36 (1H, d, J=2.0 Hz), 7.39 (1H, d, J=1.9 Hz) ppm.

$^{13}$C-NMR (DMSO-d$_6$, TMS, 101 MHz): 180.5, 152.4, 139.5, 136.0, 133.9, 130.4, 127.2, 126.4, 122.4, 118.0, 114.5, 114.1, 113.6, 57.2, 55.0, 52.5, 47.7, 36.7, 30.4, 26.2, 21.8, 8.5 ppm.

Analysis for the Formula C$_{24}$H$_{28}$Cl$_3$N$_3$O (480.87):
Calculated: C, 59.95; H, 5.87; Cl, 22.12; N, 8.74%.
Found: C, 59.86; H, 5.94; Cl, 21.43; N, 8.58%.

EXAMPLE 80

3-Ethyl-5-methyl-3-[4-(4-pyridin-2-yl-piperazin-1-yl)-butyl]-1,3-dihydro-2H-indol-2-one The title compound is prepared according to process H by applying processing method 1 starting from 3-(4-chlorobutyl)-3-ethyl-5-methyl-1,3-dihydro-2H-indol-2-one and 2-(pyridin-1-yl)-piperazine.

M.p.: 168-170° C. (ethyl acetate-etanol).

IR (KBr): 1717 (C=O) cm$^{-1}$.

$^1$H-NMR (CDCl$_3$, TMS, 400 MHz): 0.62 (3H, t), 0.92-0.60 (1H, m), 1.26-1.09 (1H, m), 1.50-1.37 (2H, m), 1.79-1.71 (2H, m), 1.95-1.85 (2H, m), 2.23 (2H, t, J=7.8 Hz), 2.45 (4H, t, J=5.1 Hz), 3.48 (4H, t, J=5.1 Hz), 6.59 (1H, m), 6.60 (1H, d, J=7.8 Hz), 6.78 (1H, d, J=7.9 Hz), 6.92 (1H, s), 6.98 (1H, dd, J=0.9, 7.9 Hz), 7.45 (1H, dt, J=2.0, 7.7 Hz), 8.18-8.16 (1H, m), 8.77 (1H, s) ppm.

$^{13}$C-NMR (CDCl$_3$, TMS, 101 MHz): 182.6, 159.5, 147.9, 138.9, 137.4, 132.6, 131.7, 127.9, 123.7, 113.1, 109.2, 107.0, 58.3, 54.2, 52.9, 45.1, 37.6, 31.0, 26.9, 22.3, 21.2, 8.5 ppm.

Analysis for the Formula C$_{24}$H$_{32}$N$_4$O (392.55):
Calculated: C, 73.43; H, 8.22; N, 14.27%.
Found: C, 73.11; H, 8.19; N, 14.26%.

EXAMPLE 81

3-{4-[4-(2-Chlorophenyl)-piperazin-1-yl]-butyl}-3-ethyl-1,3-dihydro-2H-indol-2-one The title compound is prepared according to process H by applying processing method 1 starting from 3-(4-chlorobutyl)-3-ethyl-1,3-dihydro-2H-indol-2-one and 1-(2-chlorophenyl)-piperazine.

M.p.: 145-148° C. (hexane-ethyl acetate).

IR (KBr): 3178, 1705 (C=O) cm$^{-1}$.

$^1$H-NMR (CDCl$_3$, TMS, 400 MHz): 0.64 (3H, t, J=7.4 Hz), 0.93-0.86 (1H, m), 1.20-1.15 (1H, m), 1.52-1.34 (2H, m), 1.84-1.74 (2H, m), 1.98-1.86 (2H, m), 2.27 (2H, t, J=7.8 Hz), 2.55 (4H, br s), 3.03 (4H, br s), 6.91 (1H, d, J=7.7 Hz), 6.94 (1H, dt, J=1.5, 7.6 Hz), 7.01 (1H, dd, J=1.5, 8.1 Hz), 7.05 (1H, dt, J=1.0, 7.5 Hz), 7.12 (1H, dd, J=1.2, 7.3 Hz), 7.23-7.17 (2H, m), 7.33 (1H, dd, J=1.5, 7.6 Hz) ppm.

$^{13}$C-NMR (CDCl$_3$, TMS, 101 MHz): 182.4, 149.3, 141.3, 132.6, 130.6, 128.7, 127.6, 127.5, 123.5, 123.0, 122.3, 120.3, 109.5, 58.2, 54.2, 53.2, 51.1, 37.6, 31.0, 27.0, 22.3, 8.5 ppm.

Analysis for the Formula C$_{24}$H$_{30}$ClN$_3$O (411.98):
Calculated: C, 69.97; H, 7.34; Cl, 8.61; N, 10.20%.
Found: C, 69.88; H, 7.36; Cl, 8.90; N, 9.89%.

EXAMPLE 82

3-Ethyl-6-fluoro-[4-(4-pyridin-2-yl-piperazin-1-yl)-butyl]-1,3-dihydro-2H-indol-2-one The title compound is prepared according to process H by applying processing method 1 starting from 3-(4-chlorobutyl)-3-ethyl-6-fluoro-1,3-dihydro-2H-indol-2-one and 2-(pyridin-1-yl)-piperazine.

M.p.: 137-139° C. (hexane-ethyl acetate).

IR (KBr): 3150, 1712 (C=O), 1141 cm$^{-1}$.

$^1$H-NMR (CDCl$_3$, TMS, 400 MHz): 0.63 (3H, t, J=7.3 Hz), 0.96-0.85 (1H, m), 1.16-1.14 (1H, m), 1.52-1.34 (1H, m), 1.82-1.72 (2H, m), 1.98-1.86 (2H, m), 2.25 (2H, t, J=7.8 Hz), 2.47 (4H, t, J=5.0 Hz), 3.50 (4H, t, J=5.0 Hz), 6.65-6.61 (2H, m), 6.66 (1H, dd, J=2.2, 8.8 Hz), 6.75 (1H, dt, J=2.2, 8.9 Hz), 7.05 (1H, dd, J=5.4, 8.1 Hz), 7.47 (1H, dt, J=1.9, 7.8 Hz), 8.20-8.18 (1H, m), 8.79 (1H, br s) ppm.

$^{13}$C-NMR (CDCl$_3$, TMS, 101 MHz): 8.5, 22.2, 26.9, 31.0, 37.6, 45.1, 52.9, 53.8, 58.3, 98.2 (d, J=27.1 Hz), 107.0, 108.6 (d, J=22.5 Hz), 113.2, 123.9 (d, J=9.6 Hz), 127.8 (d, J=2.7 Hz), 137.4, 142.5 (d, J=11.4 Hz), 147.9, 159.5, 162.4 (d, J=244.1 Hz), 182.8 ppm.

Analysis for the Formula C$_{23}$H$_{29}$FN$_4$O (396.51):
Calculated: C, 69.67; H, 7.37; N, 14.13%.
Found: C, 69.04; H, 7.40; N, 13.93%.

EXAMPLE 83

3-{4-[4-(2,3-Dihydrobenzo[1,4]dioxin-5-yl)-piperazin-1-yl]-butyl}-3-ethyl-6-fluoro-1,3-dihydro-2H-indol-2-one The title compound is prepared according to process H by applying processing method 1 starting from 3-(4-chlorobutyl)-3-ethyl-6-fluoro-1,3-dihydro-2H-indol-2-one and 4-(2,3-dihydro-benzo[1,4]dioxin-5-yl)-piperazine.

M.p.: 146-147° C. (hexane-ethyl acetate).

IR (KBr): 1714 (C=O), 1000 cm$^{-1}$.

$^1$H-NMR (CDCl$_3$, TMS, 400 MHz): 0.62 (3H, t, J=7.4 Hz), 10.95-0.84 (1H, m), 1.16-1.04 (1H, m), 1.50-1.32 (2H, m), 2.00-1.70 (4H, m), 2.26 (2H, t, J=7.8 Hz), 2.56 (4H, br s), 3.00 (4H, br s), 4.31-4.21 (4H, m), 6.51 (1H, dd, J=1.5, 8.0 Hz), 6.58 (1H, dd, J=1.4, 8.2 Hz), 6.63 (1H, dd, J=2.3, 8.8 Hz), 6.78-6.70 (2H, m), 7.03 (1H, dd, J=5.3, 8.2 Hz), 8.89 (1H, s) ppm.

$^{13}$C-NMR (CDCl$_3$, TMS, 101 MHz): 8.7, 22.5, 27.1, 31.3, 37.8, 50.9, 53.4, 54.0, 58.5, 64.2, 64.5, 98.4 (d, J=27.5 Hz), 108.8 (d, J=22.2 Hz), 110.9, 112.1, 120.8, 124.1 (d, J=9.5 Hz), 128.1 (d, J=2.7 Hz), 136.6, 141.9, 142.8 (d, J=11.8 Hz), 144.2, 162.5 (d, J=244.1 Hz), 183.0 ppm.

Analysis for the Formula C$_{26}$H$_{32}$FN$_3$O$_3$ (453.56):
Calculated: C, 68.85; H, 7.11; N, 9.26%.
Found: C, 68.76; H, 7.07; N, 9.30%.

EXAMPLE 84

3-Ethyl-5-fluoro-3-[4-(4-pyridin-2-yl-piperazin-1-yl)-butyl]-1,3-dihydro-2H-indol-2-one The title compound is prepared according to process H by applying processing method 1 starting from 3-(4-chlorobutyl)-3-ethyl-5-fluoro-1,3-dihydro-2H-indol-2-one and 2-(pyridin-1-yl)-piperazine.

M.p.: 144-147° C. (hexane-ethyl acetate).

IR (KBr): 1710, 1592, 1486 cm$^{-1}$.

$^1$H-NMR (CDCl$_3$, TMS, 400 MHz): 8.73 (1H, br s), 8.17 (1H, m), 7.45 (1H, m), 6.87 (3H, m), 6.61 (1H, m), 6.60 (1H, m), 3.49 (4H, t, J=5.1 Hz), 2.46 (4H, t, J=5.1 Hz), 2.24 (2H, t, J=7.6 Hz), 1.93 (2H, m), 1.76 (2H, m), 1.43 (2H, m), 1.12 (1H, m), 0.91 (1H, m), 0.64 (3H, t, J=7.4 Hz) ppm.

$^{13}$C-NMR (CDCl$_3$, TMS, 101 MHz): 182.3, 159.5, 159.2 (d, J=240.3 Hz), 147.9, 137.4, 137.2 (d, J=1.9 Hz), 134.5 (d, J=7.6 Hz), 114.0 (d, J=23.3 Hz), 113.2, 110.9 (d, J=24.0 Hz), 110.0 (d, J=8.0 Hz), 107.0, 58.2, 54.9 (d, J=1.9 Hz), 53.0, 45.1, 37.5, 31.0, 26.8, 22.2, 8.5 ppm.

Analysis for the Formula C$_{23}$H$_{29}$FN$_4$O (396.51):
Calculated: C, 69.67; H, 7.37; N, 14.13%.
Found: C, 69.15; H, 7.30; N, 14.09%.

EXAMPLE 85

3-{4-[4-(3-Chlorophenyl)-piperazin-1-yl]-butyl}-3-ethyl-5-fluoro-1,3-dihydro-2H-indol-2-one monohydrochloride The title compound is prepared according to process H by applying processing method 2 starting from 3-(4-chlorobutyl)-3-ethyl-5-fluoro-1,3-dihydro-2H-indol-2-one and 1-(3-chloro-phenyl)-piperazine.

M.p.: 121-124° C.

IR (KBr): 1711 (C=O), 1178 cm$^{-1}$.

$^1$H-NMR (DMSO-d$_6$, TMS, 400 MHz): 0.51 (3H, t, J=7.3 Hz), 0.82-0.76 (1H, m), 1.00-0.92 (1H, m), 1.83-1.61 (6H, m), 2.96 (4H, br s), 3.17 (2H, br s), 3.41 (2H, br s), 3.80 (2H, br s), 6.87-6.83 (2H, m), 6.94 (1H, dd, J=2.1, 8.3 Hz), 6.99 (1H, dd, J=2.6, 8.5 Hz), 7.03 (1H, t, J=2.0 Hz), 7.18 (H, dd, J=2.7, 8.5 Hz), 7.24 (1H, t, J=8.1 Hz) 10.5 (1H, s), 11.0 (1H, br s) ppm.

$^{13}$C-NMR (DMSO-d$_6$, TMS, 101 MHz): 8.5, 21.4, 23.2, 30.2, 36.5, 44.9, 50.4, 53.9, 54.0, 55.1, 110.0 (d, J=8.0 Hz), 111.2 (d, J=24.0 Hz), 114.0 (d, J=23.3 Hz), 114.3, 115.4, 119.3, 130.8, 134.1, 134.2 (d, J=8.0 Hz), 138.8 (d, J=1.5 Hz), 151.0, 158.3 (d, J=236.5 Hz), 180.6 ppm.

Analysis for the Formula C$_{24}$H$_{30}$Cl$_2$FN$_3$O (466.43):
Calculated: C, 61.80; H, 6.48; Cl, 15.20; N, 9.01%.
Found: C, 60.57; H, 6.50; Cl, 14.70; N, 8.77%.

EXAMPLE 86

3-{4-[4-(4-Chlorophenyl)-piperazin-1-yl]-butyl}-3-ethyl-6-fluoro-1,3-dihydro-2H-indol-2-one The title compound is prepared according to process H by applying processing method 1 starting from 3-(4-chlorobutyl)-3-ethyl-6-fluoro-1,3-dihydro-2H-indol-2-one and 1-(4-chloro-phenyl)-piperazine.

M.p.: 145-147° C. (hexane-ethyl acetate).

IR (KBr): 3284, 1716 (C=O), 1088 cm$^{-1}$.

$^1$H-NMR (CDCl$_3$, TMS, 400 MHz): 0.63 (3H, t, J=7.4 Hz), 0.96-0.84 (1H, m), 1.12-1.04 (1H, m), 1.48-1.35 (2H, m), 1.80-1.71 (2H, m), 1.95-1.81 (2H, m), 2.25 (2H, t, J=7.8 Hz), 2.50 (4H, t, J=5.0 Hz), 3.11 (4H, t, J=5.0 Hz), 6.64 (1H, dd, J=2.4, 8.7 Hz), 6.75 (1H, ddd, J=2.4, 8.2, 9.7 Hz), 6.81 (2H, d, J=9.0 Hz), 7.04 (1H, dd, J=5.3, 8.2 Hz), 7.18 (2H, d, J=8.9 Hz), 8.28 (1H, s) ppm.

$^{13}$C-NMR (CDCl$_3$, TMS, 101 MHz): 8.5, 22.2, 26.9, 31.1, 37.6, 49.0, 53.0, 53.8, 58.1, 98.2 (d, J=27.1 Hz), 108.7 (d, J=22.1 Hz), 117.1, 123.9 (d, J=9.9 Hz), 124.4, 127.8 (d, J=2.7 Hz), 128.9, 142.4 (d, J=11.4 Hz), 149.9, 162.4 (d, J=244.2 Hz), 182.6 ppm.

Analysis for the Formula C$_{24}$H$_{29}$ClFN$_3$O (429.97):
Calculated: C, 67.04; H, 6.80; Cl, 8.25; N, 9.77%.
Found: C, 66.81; H, 6.79; Cl, 8.10; N, 9.70%.

EXAMPLE 87

5,7-Dichloro-3-{4-[4-(4-chlorophenyl)-piperazin-1-yl]-butyl}-3-ethyl-1,3-dihydro-2H-indol-2-one The title compound is prepared according to process H by applying processing method 2 starting from 5,7-dichloro-3-(4-chlorobutyl)-3-ethyl-1,3-dihydro-2H-indol-2-one and 1-(4-chloro-phenyl)-piperazine.

M.p.: 152-154° C. (heptane-ethyl acetate).

IR (KBr): 3137, 1719 (C=O), 826 cm$^{-1}$.

$^1$H-NMR (CDCl$_3$, TMS, 400 MHz): 0.65 (3H, t, J=7.4 Hz), 0.98-0.86 (1H, m), 1.16-1.04 (1H, m), 1.50-1.36 (2H, m), 1.80-1.70 (2H, m), 1.98-1.88 (2H, m), 2.27 (2H, t, J=7.8 Hz), 2.51 (4H, t, J=5.0 Hz), 3.12 (4H, t, J=5.0 Hz), 6.81 (2H, d, J=9.1 Hz), 7.01 (1H, d, J=1.8 Hz), 7.18 (2H, d, J=9.1 Hz), 7.23 (1H, d, J=1.8 Hz), 8.15 (1H, s) ppm.

$^{13}$C-NMR (CDCl$_3$, TMS, 101 MHz): 180.3, 149.9, 137.7, 135.3, 128.9, 128.2, 127.5, 124.4, 122.0, 117.1, 115.7, 57.9, 55.8, 53.0, 49.1, 37.5, 31.1, 26.7, 22.2, 8.5 ppm.

Analysis for the Formula C$_{24}$H$_{28}$Cl$_3$N$_3$O (480.87):
Calculated: C, 59.95; H, 5.87; Cl, 22.12; N, 8.74%.
Found: C, 59.80; H, 5.86; Cl, 21.83; N, 8.72%.

EXAMPLE 88

7-Chloro-3-{4-[4-(3-chlorophenyl)-piperazin-1-yl]-butyl}-3-ethyl-5-fluoro-1,3-dihydro-2H-indol-2-one monohydrochloride The title compound is prepared according to process H by applying processing method 2 starting from 7-chloro-3-(4-chlorobutyl)-3-ethyl-5-fluoro-1,3-dihydro-2H-indol-2-one and 1-(3-chlorophenyl)-piperazine.

M.p.: 205-207° C.

IR (KBr): 3127, 3088, 1713 (C=O), 779 cm$^{-1}$.

$^1$H-NMR (DMSO-d$_6$, TMS, 400 MHz): 0.53 (3H, t, J=7.3 Hz), 0.83-0.78 (1H, m), 0.99-0.93 (1H, m), 1.88-1.64 (6H, m), 2.98 (4H, br s), 3.21 (2H, t, J=11.5 Hz), 3.43 (2H, br s), 3.84 (2H, d, J=11.7 Hz), 6.86 (1H, dd, J=1.5, 7.8 Hz), 6.94 (1H, dd, J=2.0, 8.1 Hz), 7.03 (1H, t, J=2.0 Hz), 10.9 (1H, s), 11.3 (1H, br s) ppm.

$^{13}$C-NMR (DMSO-d$_6$, TMS, 101 MHz): 8.5, 21.4, 23.2, 30.3, 36.5, 44.9, 50.3, 55.0, 110.5 (d, J=24.4 Hz), 113.5 (d, J=11.1 Hz), 114.3, 114.7 (d, J=26.7 Hz), 115.4, 119.3, 130.8, 134.1, 135.4 (d, J=8.4 Hz), 136.8 (d, J=2.3 Hz), 151.0, 158.0 (d, J=240.7 Hz), 180.5 ppm.

Analysis for the Formula C$_{24}$H$_{29}$Cl$_3$FN$_3$O (500.88):
Calculated: C, 57.55; H, 5.84; Cl, 21.23; N, 8.39%.
Found: C, 56.80; H, 5.77; Cl, 20.93; N, 8.33%.

EXAMPLE 89

5-Chloro-3-{4-[4-(3-chlorophenyl)-piperazin-1-yl]-butyl}-3-ethyl-6-fluoro-1,3-dihydro-2H-indol-2-one monohydrochloride The title compound is prepared according to process H by applying processing method 2 starting from 5-chloro-3-(4-chlorobutyl)-3-ethyl-6-fluoro-1,3-dihydro-2H-indol-2-one and 1-(3-chlorophenyl)-piperazine.

M.p.: 237-239° C.

IR (KBr): 3133, 2446, 1710 (C=O), 1150, 946 cm$^{-1}$ $^1$H-NMR (DMSO-d$_6$, TMS, 400 MHz): 0.51 (3H, t, J=7.3 Hz), 0.96-0.78 (2H, m), 1.87-1.63 (6H, m), 2.98 (4H, s), 3.20 (2H, t, J=11.8 Hz), 3.48-3.42 (2H, m), 3.83 (2H, d, J=12.5 Hz), 6.86 (1H, dd, J=1.4, 7.8 Hz), 6.90 (1H, d, J=9.4 Hz), 6.94 (1H, dd, J=2.0, 8.2 Hz), 7.03 (1H, t, J=2.0 Hz), 7.25 (1H, t, J=8.2 Hz), 7.52 (1H, d, J=7.4 Hz), 10.79 (1H, s), 11.15 (1H, br s) ppm.

$^{13}$C-NMR (DMSO-d$_6$, TMS, 101 MHz): 8.5, 21.4, 23.2, 30.2, 36.4, 44.9, 50.3, 53.4, 55.0, 99.0 (d, J=26.3 Hz), 111.7 (d, J=18.3 Hz), 114.3, 115.4, 119.3, 125.1, 129.4 (d, J=3.4 Hz), 130.8, 134.1, 143.0 (d, J=11.5 Hz), 151.0, 156.9 (d, J=243.8 Hz), 180.6 ppm.

Analysis for the Formula C$_{24}$H$_{29}$Cl$_3$FN$_3$O (500.88):
Calculated: C, 57.55; H, 5.84; Cl, 21.23; N, 8.39%.
Found: C, 57.08; H, 5.71; Cl, 20.76; N, 8.27%.

EXAMPLE 90

3-{4-[4-(4-Chlorophenyl)-piperazin-1-yl]-butyl}-3-ethyl-5-fluoro-1,3-dihydro-2H-indol-2-one The title compound is prepared according to process H by applying processing method 1 starting from 3-(4-chlorobutyl)-3-ethyl-5-fluoro-1,3-dihydro-2H-indol-2-one and 1-(4-chloro-phenyl)-piperazine.

M.p.: 148-150° C. (hexane-ethyl acetate).

IR (KBr): 3278, 1716 (C=O), 1178, 823 cm$^{-1}$.

$^1$H-NMR (CDCl$_3$, TMS, 400 MHz): 0.64 (3H, t, J=7.4 Hz), 0.97-0.86 (1H, m), 1.16-1.07 (1H, m), 1.49-1.35 (2H, m), 1.81-1.70 (2H, m), 1.98-1.88 (2H, m), 2.25 (2H, t, J=7.5 Hz), 2.50 (4H, t, J=5.0 Hz), 3.11 (4H, t, J=5.0 Hz), 6.80 (2H, d, J=9.1 Hz), 6.94-6.78 (3H, m), 7.18 (2H, d, J=9.1 Hz), 8.03 (1H, s) ppm.

$^{13}$C-NMR (CDCl$_3$, TMS, 101 MHz): 8.5, 22.2, 26.8, 31.1, 37.5, 49.0, 53.0, 54.9 (d, J=1.9 Hz), 58.1, 110.0 (d, J=8.0 Hz), 111.0 (d, J=24.4 Hz), 114.0 (d, J=23.7 Hz), 117.1, 124.4, 128.9, 134.4 (d, J=8.0 Hz), 137.1 (d, J=1.9 Hz), 149.9, 159.2 (d, J=240.3 Hz), 182.2 ppm.

Analysis for the Formula C$_{24}$H$_{29}$ClFN$_3$O (429.97):
Calculated: C, 67.04; H, 6.80; Cl, 8.25; N, 9.77%.
Found: C, 66.35; H, 6.78; Cl, 8.11; N, 9.69%.

EXAMPLE 91

3-Ethyl-3-{4-[4-(3-methoxyphenyl)-piperazin-1-yl]-butyl}-1,3-dihydro-2H-indol-2-one The title compound is prepared according to process H by applying processing method 1 starting from 3-(4-chlorobutyl)-3-ethyl-1,3-dihydro-2H-indol-2-one and 1-(3-methoxyphenyl)-piperazine.

M.p.: 123-125° C. (hexane-ethyl acetate).

IR (KBr): 3363, 1705 (C=O) cm$^{-1}$.

$^1$H-NMR (CDCl$_3$, TMS, 400 MHz): 0.62 (3H, t, J=7.4 Hz), 0.92-0.88 (1H, m), 1.22-1.10 (1H, m), 1.45-1.37 (2H, m), 2.23 (2H, t, J=7.8 Hz), 2.49 (4H, t, J=5.0 Hz), 3.13 (4H, t, J=5.0 Hz), 3.76 (3H, s), 6.39 (1H, ddd, J=0.6, 2.3, 8.1 Hz), 6.43 (1H, t, J=2.3 Hz), 6.50 (1H, ddd, J=0.6, 2.3, 8.2 Hz), 6.90 (1H, d, J=7.6 Hz), 7.03 (1H, dt, J=1.0, 7.5 Hz), 7.10 (1H, dd, J=0.8, 7.4 Hz), 7.14 (1H, t, J=8.1 hH), 7.18 (1H, dt, J=1.3, 7.6 Hz), 9.39 (1H, s) ppm.

$^{13}$C-NMR (CDCl$_3$, TMS, 101 MHz): 182.9, 160.4, 152.6, 141.5, 132.5, 129.6, 127.5, 122.9, 122.2, 109.5, 108.7, 104.2, 102.3, 58.1, 55.0, 54.1, 52.9, 48.8, 37.4, 30.9, 26.8, 22.2, 8.5 ppm.

Analysis for the Formula C$_{25}$H$_{33}$N$_3$O$_2$ (407.56):
Calculated: C, 73.68; H, 8.16; N, 10.31%.
Found: C, 73.50; H, 8.19; N, 10.11%.

EXAMPLE 92

3-{5-[4-(3-Chlorophenyl)-piperazin-1-yl]-pentyl}-3-ethyl-1,3-dihydro-2H-indol-2-one monooxalate The title compound is prepared according to process H by applying processing method 3 starting from 3-(5-bromopentyl)-3-ethyl-1,3-dihydro-2H-indol-2-one and 1-(3-chlorophenyl)-piperazine.

M.p.: 127-129° C.

IR (KBr): 3187, 1705 (C=O), 754 cm$^{-1}$.

$^1$H-NMR (DMSO-d$_6$, TMS, 400 MHz): 0.50 (3H, t, J=7.4 Hz), 0.90-0.76 (1H, m), 1.04-0.90 (1H, m), 1.15 (2H, q, J=6.8 Hz), 1.50 (2H, q, J=7.5 Hz), 1.80-1.64 (4H, m), 2.81 (2H, t, J=7.9 Hz), 3.07 (4H, br s), 3.38 (4H, br s), 6.84 (2H, d, J=8.4 Hz), 6.93 (1H, dd, J=2.0, 8.4 Hz), 6.98 (1H, dt, J=0.9, 7.6 Hz), 7.00 (1H, t, J=2.3 Hz), 7.16 (1H, dt, J=1.1, 7.7 Hz), 7.20 (1H, d, J=7.6 Hz), 7.24 (1H, dt, J=8.1 Hz), 8.8-7.4 (2H, br s), 10.35 (1H, s) ppm.

$^{13}$C-NMR (DMSO-d$_6$, TMS, 101 MHz): 180.9, 164.3, 151.3, 142.7, 134.1, 132.4, 130.7, 127.7, 123.1, 121.6, 119.1, 115.2, 114.2, 109.3, 55.9, 53.2, 50.9, 45.6, 36.9, 30.5, 26.6, 23.8, 23.6, 8.6 ppm.

Analysis for the Formula C$_{27}$H$_{34}$ClN$_3$O$_5$ (516.04):
Calculated: C, 62.84; H, 6.64; Cl, 6.87; N, 8.14°.
Found: C, 62.43; H, 6.68; Cl, 6.92; N, 8.04%.

EXAMPLE 93

3-Ethyl-3-[5-(4-pyridin-2-yl-piperazin-1-yl)-pentyl]-1,3-dihydro-2H-indol-2-one

The title compound is prepared according to process H by applying processing method 1 starting from 3-(4-bromopentyl)-3-ethyl-1,3-dihydro-2H-indol-2-one and 2-(pyridin-1-yl)-piperazine.

M.p.: 127-128° C. (hexane-ethyl acetate).

IR (KBr): 3155, 1710 (C=O), 1683 cm$^{-1}$.

$^1$H-NMR (CDCl$_3$, TMS, 400 MHz): 0.63 (3H, t, J=7.4 Hz), 0.93-0.88 (1H, m), 1.30-1.09 (3H, m), 1.40-1.35 (2H, m), 1.95-1.70 (4H, m), 2.47 (4H, t, J=5.1 Hz), 3.50 (4H, t, J=5.0 Hz), 6.63-6.58 (2H, m), 6.90 (1H, dd, J=0.3, 7.7 Hz), 7.04 (1H, dt, J=1.0, 7.5 Hz), 7.11 (1H, dd, J=0.6, 6.7 Hz), 7.18 (1H, dt, J=1.4, 7.6 Hz), 7.45 (1H, dt, J=2.0, 7.8 Hz), 8.17 (1H, ddd, J=0.8, 2.0, 4.9 Hz), 8.90 (1H, br s) ppm.

$^{13}$C-NMR (CDCl$_3$, TMS, 101 MHz): 182.6, 159.5, 147.9, 141.4, 137.3, 132.7, 127.5, 122.9, 122.3, 113.2, 109.5, 107.4, 58.6, 54.2, 53.0, 45.1, 37.6, 31.1, 27.7, 26.4, 24.1, 8.5 ppm.

Analysis for the Formula C$_{24}$H$_{32}$N$_4$O (392.55):
Calculated: C, 73.43; H, 8.22; N, 14.27%.
Found: C, 72.96; H, 8.19; N, 14.02%.

EXAMPLE 94

3-{5-[4-(2-chlorophenyl)-piperazin-1-yl]-pentyl}-3-ethyl-1,3-dihydro-2H-indol-2-one monohydro-chloride The title compound is prepared according to process H by applying processing method 2 starting from 3-(5-bromopentyl)-3-ethyl-1,3-dihydro-2H-indol-2-one and 1-(2-chlorophenyl)-piperazine.

M.p.: 100-103° C.

IR (KBr): 3432, 2459, 1709 (C=O) cm$^{-1}$.

$^1$H-NMR (CDCl$_3$, TMS, 400 MHz): 0.62 (3H, t, J=7.4 Hz), 1.0-0.90 (1H, m), 1.18-1.08 (1H, m), 1.31-1.20 (2H, m), 1.93-1.72 (6H, m), 2.91 (2H, t, J=8.4 Hz), 3.2-2.9 (2H, br s), 3.7-3.3 (6H, br s), 6.95 (1H, d, J=7.8 Hz), 7.10-7.02 (3H, m), 7.11 (1H, d, J=6.4 Hz), 7.20 (1H, dt, J=1.4, 7.7 Hz), 7.23 (1H, dt), J=1.5, 7.6 Hz), 7.36 (1H, dd, J=1.6, 7.8 Hz), 8.56 (1H, s), 12.6 (1H, br s) ppm.

$^{13}$C-NMR (CDCl$_3$, TMS, 101 MHz): 182.0, 147.1, 141.3, 132.2, 130.6, 128.7, 127.9, 127.7, 125.1, 123.0, 122.4, 121.0, 109.7, 57.3, 53.9, 52.2, 47.9, 37.1, 31.1, 26.7, 23.7, 23.1, 8.5 ppm.

Analysis for the Formula C$_{25}$H$_{33}$Cl$_2$N$_3$O (462.47):
Calculated: C, 64.93; H, 7.19; Cl, 15.33; N, 9.09%.
Found: C, 64.08; H, 7.18; Cl, 15.12; N, 9.04%.

EXAMPLE 95

3-Ethyl-3-{4-[4-(4-fluorophenyl)-piperazin-1-yl]-butyl}-1,3-dihydro-2H-indol-2-one The title compound is prepared according to process H by applying processing method 1 starting from 3-(4-chlorobutyl)-3-ethyl-1,3-dihydro-2H-indol-2-one and 1-(4-fluorophenyl)-piperazine.

M.p.: 118-119° C. (hexane-ethyl acetate).

IR (KBr): 3161, 1713 (C=O) cm$^{-1}$.

$^1$H-NMR (CDCl$_3$, TMS, 400 MHz): 0.63 (3H, t, J=7.4 Hz), 0.94-0.88 (1H, m), 1.14-1.10 (1H, m), 1.47-1.35 (2H, m), 1.84-1.74 (2H, m), 1.97-1.88 (2H, m), 2.24 (2H, t, J=7.8 Hz), 2.50 (4H, t, J=4.9 Hz), 3.06 (4H, t, J=4.9 hz), 6.82 (2H, dd, J=4.7, 9.3 Hz), 6.90 (1H, d, J=8.0 Hz), 6.93 (2H, t, J=9.1 Hz), 7.04 (1H, dt, J=0.8, 7.5 Hz), 7.11 (1H, d, J=6.6 Hz), 7.19 (1H, dt, J=1.3, 7.6 Hz), 9.06 (1H, s) ppm.

$^{13}$C-NMR (CDCl$_3$, TMS, 101 MHz): 8.5, 22.2, 26.9, 31.0, 37.5, 50.0, 53.1, 54.2, 58.1, 109.5, 115.4 (d, J=22.1 Hz), 117.6 (d, J=7.6 Hz), 122.3, 123.0, 127.6, 132.6, 141.4, 147.9 (d, J=1.9 Hz), 157.0 (d, J=238.8 Hz), 182.8 ppm.

Analysis for the Formula C$_{24}$H$_{30}$FN$_3$O (395.52):
Calculated: C, 72.88; H, 7.65; N, 10.62%.
Found: C, 73.22; H, 7.74; N, 10.47%.

EXAMPLE 96

3-{4-[4-(4-Chloro-3-trifluoromethyl-phenyl)-piperazin-1-yl]-butyl}-3-ethyl-1,3-dihydro-2H-indol-2-one monohydrochloride The title compound is prepared according to process H by applying processing method 2 starting from 3-(4-chlorobutyl)-3-ethyl-1,3-dihydro-2H-indol-2-one and 1-(4-chloro-3-tri-fluormethyl-phenyl)-piperazine.

M.p.: 204-206° C.

IR (KBr): 3177, 1700 (C=O), 1307, 1137 cm$^{-1}$.

$^1$H-NMR (CDCl$_3$, TMS, 400 MHz): 0.60 (3H, t, J=7.4 Hz), 1.00-0.90 (1H, m), 1.16-1.04 (1H, m), 1.96-1.72 (6H, m), 3.00-2.88 (4H, m), 3.68-3.47 (6H, m), 6.97 (1H, dd, J=2.8, 8.9 Hz), 6.98 (1H, d, J=7.2 Hz), 7.03 (1H, t, J=7.4 Hz), 7.08 (1H, d, J=6.4 Hz), 7.17 (1H, d, J=2.7 Hz), 7.19 (1H, dt, J=1.3, 7.6 Hz), 7.37 (1H, d, J=8.8 Hz), 9.29 (1H, s), 12.47 (1H, br s) ppm.

$^{13}$C-NMR (CDCl$_3$, TMS, 101 MHz): 8.4, 21.7, 23.3, 31.1, 36.6, 46.2, 51.3, 51.4, 53.8, 56.9, 110.0, 116.0 (q, J=5.7 Hz), 120.8, 122.4, 122.6 (q, J=273.5 Hz), 122.8, 123.8 (q, J=1.5 Hz), 127.8, 128.9 (q, J=31.3 Hz), 131.7, 132.3, 141.5, 148.0, 181.9 ppm.

Analysis for the Formula C$_{25}$H$_{30}$Cl$_2$F$_3$N$_3$O (516.44):
Calculated: C, 58.14; H, 5.86; Cl, 13.73; N, 8.14%.
Found: C, 57.99; H, 5.85; Cl, 13.67; N, 8.07%.

EXAMPLE 97

3-{4-[4-(3,4-Dichlorophenyl)-piperazin-1-yl]-butyl}-3-ethyl-1,3-dihydro-2H-indol-2-one hydrogen chloride-water-isopropanol (1:1:1:1)

The title compound is prepared according to process H by applying processing method 2 starting from 3-(4-chlorobutyl)-3-ethyl-1,3-dihydro-2H-indol-2-one and 1-(3,4-dichloro-phenyl)-piperazine.

M.p.: 224-226° C.

IR (KBr): 3385, 1708 (C=O), 946 cm$^{-1}$.

$^1$H-NMR (DMSO-d$_6$, TMS, 400 MHz): 0.51 (3H, t, J=7.3 Hz), 0.81-0.77 (1H, m), 1.01-0.95 (1H, m), 1.82-1.62 (6H, m), 3.6-2.9 (8H, m), 3.82 (1H, br s), 4.38 (1H, br s), 6.87 (1H, d, J=7.6 Hz), 7.02-6.97 (2H, m), 7.23-7.16 (3H, m), 7.44 (1H, d, J=9.0 Hz), 10.4 (1H, s), 11.1 (1H, br s) ppm.

$^{13}$C-NM (DMSO-d$_6$, TMS, 101 MHz): 8.6, 21.4, 23.3, 30.3, 36.6, 44.9, 50.2, 53.2, 55.1, 109.4, 116.0, 117.1, 120.9, 121.7, 123.2, 127.8, 130.8, 131.8, 132.1, 142.7, 149.5, 180.8 ppm.

Analysis for the Formula C$_{27}$H$_{40}$Cl$_3$N$_3$O$_3$ (561.00):
Calculated: C, 57.81; H, 7.19; Cl, 18.96; N, 7.49%.
Found: C, 58.46; H, 7.26; Cl, 18.89; N, 7.87%.

EXAMPLE 98

3-{4-[4-(4-Chloro-2-methylphenyl)-piperazin-1-yl]-butyl}-3-ethyl-1,3-dihydro-2H-indol-2-one monohydrochloride The title compound is prepared according to process H by applying processing method 2 starting from 3-(4-chlorobutyl)-3-ethyl-1,3-dihydro-2H-indol-2-one and 1-(4-chloro-2-methyl-phenyl)-piperazine.

M.p.: 247-249° C.

IR (KBr): 3138, 2435, 1712 (C=O) cm$^{-1}$.

$^1$H-NMR (DMSO-d$_6$, TMS, 400 MHz): 0.51 (3H, t, J=7.4 Hz), 0.86-0.81 (1H, m), 0.98-0.96 (1H, m), 1.76-1.63 (6H, m), 2.24 (3H, s), 2.97 (2H, s), 3.11 (8H, br s), 6.85 (1H, d, J=7.7 Hz), 7.00 (1, dt, J=1.0, 7.5 Hz), 7.04 (1H, d, J=8.5 Hz), 7.18 (1H, dt, J=1.2, 7.6 Hz), 7.23-7.21 (2H, m), 7.26 (1H, d, J=2.2 Hz), 10.45 (1H, s), 11.1 (1H, br s) ppm.

$^{13}$C-NMR (DMSO-d$_6$, TMS, 101 MHz): 8.6, 17.4, 21.4, 23.3, 30.3, 36.6, 48.1, 51.3, 53.2, 55.1, 109.4, 120.9, 121.7, 123.2, 126.5, 127.8, 130.6, 132.1, 134.7, 142.7, 148.9, 180.8 ppm.

Analysis for the Formula C$_{25}$H$_{33}$Cl$_2$N$_3$O (462.47):
Calculated: C, 64.93; H, 7.19; Cl, 15.33; N, 9.09%.
Found: C, 65.25; H, 7.27; Cl, 15.00; N, 9.02%.

EXAMPLE 99

3-{4-[4-(3-Chloro-4-methylphenyl)-piperazin-1-yl]-butyl}-3-ethyl-1,3-dihydro-2H-indol-2-one The title compound is prepared according to process H by applying processing method 1 starting from 3-(4-chlorobutyl)-3-ethyl-1,3-dihydro-2H-indol-2-one and 1-(3-chloro-4-methyl-phenyl)-piperazine.

M.p.: 103-106° C. (hexane-ethyl acetate).

IR (KBr): 3166, 1716 (C=O), 749 cm$^{-1}$.

$^1$H-NMR (DMSO-d$_6$, TMS, 400 MHz): 0.49 (3H, t, J=7.4 Hz), 0.84-0.76 (1H, m), 0.98-0.94 (1H, m), 1.32-1.23 (2H, m), 1.74-1.68 (2H, m), 2.12 (2H, t, J=6.6 Hz), 2.19 (3H, s), 2.34 (4H, t, J=4.7 Hz), 3.01 (4H, t, J=4.7 Hz), 6.77 81H, dd, J=2.4, 8.4 Hz), 6.83 (1H, d, J=7.5 Hz), 6.87 (1H, d, J=2.4 Hz), 6.96 (1H, dt, J=0.7, 7.0 Hz), 7.17-7.10 (3H, m), 10.3 (1H, s) ppm.

$^{13}$C-NMR (DMSO-d$_6$, TMS, 101 MHz): 8.6, 18.6, 22.0, 26.6, 30.5, 37.1, 48.2, 52.6, 53.3, 57.6, 109.2, 114.3, 115.3, 121.5, 123.1, 124.8, 127.6, 131.4, 132.4, 133.8, 142.7, 150.6, 181.0 ppm.

Analysis for the Formula C$_{25}$H$_{32}$ClN$_3$O (426.01):
Calculated: C, 70.49; H, 7.57; Cl, 8.32; N, 9.86%.
Found: C, 70.18; H, 7.54; Cl, 8.33; N, 9.79%.

EXAMPLE 100

3-{4-[4-(3-Chloro-4-fluorophenyl)-piperazin-1-yl]-butyl}-3-ethyl-1,3-dihydro-2H-indol-2-one The title compound is prepared according to process H by applying processing method 1 starting from 3-(4-chlorobutyl)-3-ethyl-1,3-dihydro-2H-indol-2-one and 1-(3-chloro-4-fluoro-phenyl)-piperazine.

M.p.: 121-124° C. (hexane-ethyl acetate).

IR (KBr): 3441, 1713 (C=O), 752 cm$^{-1}$.

$^1$H-NMR (CDCl$_3$, TMS, 400 MHz): 0.64 (3H, t, J=7.4 Hz), 0.95-0.88 (1H, m), 1.15-1.10 (1H, m), 1.47-1.35 (2H, m), 1.82-1.73 (2H, m), 1.97-1.88 (2H, m), 2.24 (2H, t, J=7.8 Hz), 2.49 (4H, t, J=5.0 Hz), 3.06 (4H, t, J=5.0 Hz), 6.72 (1H, ddd, J=3.0, 3.9, 9.1 Hz), 6.88 (1H, dd, J=2.9, 6.3 Hz), 6.88 (1H, d, J=7.9 Hz), 7.00 (1H, t, J=8.9 Hz), 7.05 (1H, dt, J=1.0, 7.5 Hz), 7.12 (1H, dt, J=0.7, 7.4 Hz), 7.21 (1H, dt, J=1.5, 7.6 Hz), 7.88 (1H, s) ppm.

$^{13}$C-NMR (CDCl$_3$, TMS, 50.3 and 101 MHz): 8.5, 22.2, 26.9, 31.1, 37.6, 49.5, 52.9, 54.1, 58.1, 109.3, 115.6 (d, J=6.5 Hz), 116.5 (d, J=21.7 Hz), 117.8, 120.9 (d, J=18.4 Hz), 122.4, 123.1, 127.6, 132.6, 141.1, 148.4 (d, J=2.7 Hz), 152.1 (d, J=241.1 Hz), 181.9 ppm.

Analysis for the Formula C$_{24}$H$_{29}$ClFN$_3$O (429.97):
Calculated: C, 67.04; H, 6.80; Cl, 8.25; N, 9.77%.
Found: C, 66.62; H, 6.78; Cl, 8.26; N, 9.61%.

EXAMPLE 101

3-{4-[4-(5-Chloro-2-methoxyphenyl)-piperazin-1-yl]-butyl}-3-ethyl-1,3-dihydro-2H-indol-2-one monohydrochloride The title compound is prepared according to process H by applying processing method 2 starting from 3-(4-chlorobutyl)-3-ethyl-1,3-dihydro-2H-indol-2-one and 1-(5-chloro-2-methoxyphenyl)-piperazine.

M.p.: 259-263° C.

IR (KBr): 3141 (NH), 2448 (HCl), 1704 (C=O) cm$^{-1}$.

$^1$H-NMR (DMSO-d$_6$, TMS, 400 MHz): 0.51 (3H, t, J=7.4 Hz), 0.87-0.76 (1H, m), 1.00-0.92 (1H, m), 1.81-1.60 (6H, m), 3.11-2.94 (6H, m), 3.49-3.40 (4H, m), 3.78 (3H, s), 6.87 (1H, d, J=7.7 Hz), 6.90 (1H, d, J=2.5 Hz), 7.02-6.96 (2H, m), 7.04 81H, dd, J=2.4, 8.7 Hz), 7.18 (1H, dt, J=1.0, 7.7 Hz), 7.22 (1H, d, J=7.3 Hz), 10.44 (1H, s), 11.36 (1H, br s) ppm.

$^{13}$C-NMR (DMSO-d$_6$, TMS, 101 MHz): 8.6, 21.4, 23.2, 30.3, 36.6, 46.6, 50.9, 53.2, 55.1, 55.9, 109.3, 113.4, 118.3, 121.7, 122.6, 123.2, 124.6, 127.8, 132.1, 140.8, 142.7, 150.8, 180.7 ppm.

Analysis for the Formula C$_{25}$H$_{33}$Cl$_2$N$_3$O$_2$ (478.47):
Calculated: C, 62.76; H, 6.95; Cl, 14.82; N, 8.78%.
Found: C, 62.39; H, 7.02; Cl, 14.75; N, 8.62%.

EXAMPLE 102

3-{4-[4-(4-Chlorophenyl)-piperazin-1-yl]-butyl}-3-isobutyl-7-methyl-1,3-dihydro-2H-indol-2-one monohydrochloride The title compound is prepared according to process H by applying processing method 2 starting from 3-(4-chlorobutyl)-3-isobutyl-7-methyl-1,3-dihydro-2H-indol-2-one and 1-(4-chlorophenyl)-piperazine.

M.p.: 146-149° C.

IR (KBr): 3390, 3167, 1706 (C=O) cm$^{-1}$.

$^1$H-NMR (DMSO-d$_6$, TMS, 400 MHz): 0.57 (3H, d, J=6.7 Hz), 0.67 (3H, d, J=6.7 Hz), 0.82-0.70 (1H, m), 1.02-0.88 (1H,m), 1.28-1.18 (1H, m), 1.76-1.57 (6H, m), 2.21 (3H, s), 3.13-2.90 (6H, m), 3.44-3.42 (2H, m), 3.75-3.73 (2H, m), 6.90 (1H, t, J=7.4 Hz), 6.99 (2H,d, J=9.2 Hz), 7.27 (2H, d, J=9.2 Hz), 10.44 (1H, s), 11.0 (1H, br s) ppm.

$^{13}$C-NMR (DMSO-d$_6$, TMS, 101 MHz): 16.7, 20.9, 23.2, 23.3, 24.3, 25.0, 38.9, 45.3, 45.9, 50.4, 52.3, 55.1, 117.6, 118.6, 120.8, 121.5, 123.7, 128.9, 129.0, 132.1, 141.0, 148.6, 181.7 ppm.

Analysis for the Formula C$_{27}$H$_{37}$Cl$_2$N$_3$O (490.52):
Calculated: C, 66.11; H, 7.60; Cl, 14.46; N, 8.57%.
Found: C, 65.94; H, 7.54; Cl, 14.25; N, 8.47%.

EXAMPLE 103

3-{4-[4-(2,4-Dichlorophenyl)-piperazin-1-yl]-butyl}-3-ethyl-1,3-dihydro-2H-indol-2-one monohydrochloride The title compound is prepared according to process H by applying processing method 2 starting from 3-(4-chlorobutyl)-3-ethyl-1,3-dihydro-2H-indol-2-one and 1-(2,4-dichloro-phenyl)-piperazine.

M.p.: 146-148° C.

IR (KBr): 3157, 1717 (C=O) cm$^{-1}$.

$^1$H-NMR (DMSO-d$_6$, TMS, 400 MHz): 0.51 (3H, t, J=7.4 Hz), 0.86-0.78 (1H, m), 1.00-0.94 (1H, m), 1.81-1.61 (6H, m), 3.46-2.97 (10H, m), 6.87 (1H, d, J=7.6 Hz), 7.00 (1H, dt, J=0.9, 7.5 Hz), 7.18 (1H, dt, J=1.3, 7.6 Hz), 7.21 (1H, d, J=8.7 Hz), 7.22 (1H, d, J=6.8 Hz), 7.39 (1H, dd, J=2.5, 8.7 Hz), 7.58 (1H, d, J=2.5 Hz), 10.45 (1H, s), 11.20 (1H, br s) ppm.

$^{13}$C-NMR (DMSO-d$_6$, TMS, 101 MHz): 8.6, 21.4, 23.3, 30.3, 36.6, 47.6, 51.0, 53.2, 55.2, 109.4, 121.7, 122.5, 123.2, 127.8, 128.1, 128.3, 128.6, 129.9, 132.1, 142.7, 146.7, 180.8 ppm.

Analysis for the Formula C$_{24}$H$_{30}$Cl$_3$N$_3$O (482.89):
Calculated: C, 59.70; H, 6.26; Cl, 22.03; N, 8.70%.
Found: C, 59.52; H, 6.29; Cl, 21.32; N, 8.39%.

EXAMPLE 104

3-{4-[4-(3-Chlorophenyl)-piperazin-1-yl]-butyl}-3-isobutyl-7-methyl-1,3-dihydro-2H-indol-2-one monohydrochloride The title compound is prepared according to process H by applying processing method 2 starting from 3-(4-chlorobutyl)-3-isobutyl-7-methyl-1,3-dihydro-2H-indol-2-one and 1-(3-chlorophenyl)-piperazine.

M.p.: 125-128° C.

IR (KBr): 3386, 3160, 1711 (C=O) cm$^{-1}$.

$^1$H-NMR (DMSO-d$_6$, TMS, 400 MHz): 0.52 (1H, d, J=6.7 Hz), 0.63 (1H, d, J=6.6 Hz), 0.91-0.87 (1H, m), 0.75-0.67 (1H, m), 1.21-1.13 (1H, m), 1.74-1.55 (6H, m), 2.18 (3H, s), 2.91-2.89 (4H,m), 3.14 (2H, m), 3.44-3.23 (2H, m), 3.76 (2H, m), 6.99-6.80 (6H, m), 7.21 (1H, t, J=8.2 Hz), 10.43 (1H, s), 11.12 (1H, br s) ppm.

$^{13}$C-NMR (DMSO-d$_6$, TMS, 101 MHz): 16.7, 20.9, 23.2, 23.3, 24.3, 25.0, 44.9, 45.9, 50.3, 52.3, 55.1, 56.2, 114.3, 115.4, 118.6, 119.3, 120.8, 121.6, 129.1, 130.8, 132.1, 134.1, 141.0, 151.0, 181.7 ppm.

Analysis for the Formula C$_{27}$H$_{37}$Cl$_2$N$_3$O (490.52):
Calculated: C, 66.11; H, 7.60; Cl, 14.46; N, 8.57%.

EXAMPLE 105

3-Ethyl-3-{4-[4-(3-fluorophenyl)-piperazin-1-yl]-butyl}-1,3-dihydro-2H-indol-2-one monohydro-chloride The title compound is prepared according to process H by applying processing method 2 starting from 3-(4-chlorobutyl)-3-ethyl-1,3-di-hydro-2H-indol-2-one and 1-(3-fluorophenyl)-piperazine.

M.p.: 181-183° C.

IR (KBr): 3168, 1705 (C=O) cm$^{-1}$.

$^1$H-NMR (DMSO-d$_6$, TMS, 400 MHz): 0.51 (3H, t, J=7.4 Hz), 0.83-0.77 81H, m), 0.99-0.94 (1H, m), 1.81-1.61 (6H, m), 3.04-2.95 (4H, m), 3.20 (2H, t, J=11.9 Hz), 3.46-3.41 (2H, m), 3.82 (2H, d, J=13.1 Hz), 6.62 (1H, dt, J=1.9, 8.4 Hz), 6.85-6.81 (2H, m), 6.88 (1H, d, J=7.7 Hz), 7.00 (1H, dt, J=0.9, 7.5 Hz), 7.29-7.16 (3H, m), 10.5 (1H, s), 11.2 (1H, br s) ppm.

$^{13}$C-NMR (DMSO-d$_6$, TMS, 101 MHz): 8.6, 21.5, 23.2, 30.3, 36.6, 44.9, 50.3, 53.2, 55.1, 102.7 (d, J=25.6 Hz), 106.0 (d, J=21.4 Hz), 109.4, 111.5 (d, J=1.9 Hz), 121.7, 123.2, 127.8, 130.8 (d, J=9.9 Hz), 132.1, 142.7, 151.5 (d, J=9.9 Hz), 163.4 (d, J=241.1 Hz), 180.8 ppm.

Analysis for the Formula C$_{24}$H$_{31}$ClFN$_3$O (431.99):
Calculated: C, 66.73; H, 7.23; Cl, 8.21; N, 9.73%.
Found: C, 66.14; H, 7.21; Cl, 8.09; N, 9.60%.

EXAMPLE 106

5,7-Dichloro-3-ethyl-3-{4-[4-(4-fluorophenyl)-piperazin-1-yl]-butyl}-1,3-dihydro-2H-indol-2-one monohydrochloride The title compound is prepared according to process H by applying processing method 1 starting from 5,7-dichloro-3-(4-chlorobutyl)-3-ethyl-1,3-dihydro-2H-indol-2-one and 4-(4-fluoro-phenyl)-piperazine.

M.p.: 227-229° C.

IR (KBr): 3177, 2510, 2447, 1726, 1711 (C=O), cm$^{-1}$.

$^1$H-NMR (DMSO-d$_6$, TMS, 400 MHz): 0.52 (3H, t), 0.82-0.80 81H, m), 0.96-0.94 (1H, m), 1.89-1.64 (6H, m), 3.14-2.98 (6H, m), 3.45 (2H, m), 3.67 (2H, d, J=12.1 Hz), 7.00 (2H, dd, J=4.7, 9.5 Hz), 7.09 (2H, t, J=8.9 Hz), 7.43 (2H, s), 11.04 (2H, s) ppm.

$^{13}$C-NMR (DMSO-d$_6$, TMS, 101 MHz): 8.5, 21.4, 23.2, 30.3, 36.4, 46.2, 50.6, 54.9, 114.3, 115.6 (d, J=22.1 Hz), 118.0 (d, J=7.6 Hz), 122.6, 126.5, 127.4, 135.8, 139.5, 146.6 (d, J=1.9 Hz), 156.7 (d, J=236.9 Hz), 180.4 Hz) ppm.

Analysis for the Formula C$_{24}$H$_{29}$Cl$_3$FN$_3$O (500.88):
Calculated: C, 57.55; H, 5.84; Cl, 21.23; N, 8.39%.
Found: C, 57.03; H, 5.97; Cl, 20.71; N, 8.22%.

EXAMPLE 107

5-Chloro-3-{4-[4-(2,4-dichlorophenyl)-piperazin-1-yl]-butyl}-3-ethyl-6-fluoro-1,3-dihydro-2H-indol-2-one monohydrochloride The title compound is prepared according to process H by applying processing method 2 starting from 5-chloro-3-(4-chlorobutyl)-3-ethyl-6-fluoro-1,3-dihydro-2H-indol-2-one and 1-(2,4-dichlorophenyl)-piperazine.

M.p.: 238-240° C.

IR (KBr): 3144, 2549, 2469, 1706 (C=O) cm$^{-1}$.

$^1$H-NMR (DMSO-d$_6$, TMS, 400 MHz): 0.51 (3H, t, J=7.3 Hz), 0.84-0.80 (1H, m), 0.95-0.90 (1H, m), 1.86-1.61 (6H, m), 3.17-3.01 (6H, m), 3.38-3.33 (2H, m), 3.47 (2H, d, J=8.7 Hz), 6.88 (1H, d, J=9.4 Hz), 7.21 (1H, d, J=8.7 Hz), 7.40 81H, dd, J=2.4, 8.7 Hz), 7.53 (1H, d, J=7.4 Hz), 7.59 (1H, d, J=2.4 Hz) ppm.

$^{13}$C-NMR (DMSO-d$_6$, TMS, 101 MHz): 8.5, 21.4, 23.3, 30.2, 36.4, 47.7 51.1, 53.4, 55.1, 99.0 (d, J=26.3 Hz), 111.7 (d, J=18.7 Hz), 122.5, 125.1, 128.1, 128.3, 128.7, 129.5, 130.0, 143.0 (d, J=11.1 Hz), 146.7, 156.9 (d, J=243.8 Hz), 180.6 ppm.

Analysis for the Formula C$_{24}$H$_{28}$Cl$_4$FN$_3$O (535.32):
Calculated: H, 5.27; N, 7.85%.
Found: H, 5.42; N, 7.26%.

EXAMPLE 108

3-{3-[4-(3-Chlorophenyl)-piperazin-1-yl]-propyl}-3-ethyl-1,3-dihydro-2H-indol-2-one The title compound is prepared according to process H by applying processing method 1 starting from 3-(3-chloropropyl)-3-ethyl-1,3-dihydro-2H-indol-2-one and 1-(3-chlorophenyl)-piperazine.

M.p.: 119-120° C. (hexane-ethyl acetate).

IR (KBr): 3434, 3171, 1716 (C=O), 749 cm$^{-1}$.

$^1$H-NMR (CDCl$_3$, TMS, 400 MHz): 0.64 (3H, t, J=7.4 Hz), 1.17-1.04 (1H, m), 1.40-1.24 (1H, m), 1.86-1.76 (2H, m), 2.00-1.88 (2H, m), 2.26 (2H, t, J=7.4 Hz), 2.42 (4H, t, J=5.1 Hz), 3.10 (4H, t, J=5.1 Hz) 6.71 (1H, dd, J=1.7, 8.4 Hz), 6.76 (1H, dd, J=1.1, 7.9 Hz), 6.81 (1H, t, J=2.1 Hz), 6.91 (1H, d, J=7.7 Hz), 7.05 (1H, dt, J=1.1, 7.5 Hz), 7.12 (1H, d, J=6.3 Hz), 7.12 (1H, t, J=8.2 Hz), 7.20 (1H, dt, J=1.4, 7.6 Hz), 8.96 (1H, s) ppm.

$^{13}$C-NMR (CDCl$_3$, TMS, 101 MHz): 182.6, 152.2, 141.4, 134.8, 132.5, 129.9, 127.7, 123.0, 122.4, 119.1, 115.6, 113.7, 109.6, 58.2, 54.0, 52.8, 48.5, 35.2, 31.0, 21.2, 8.6 ppm.

Analysis for the Formula C$_{23}$H$_{28}$ClN$_3$O (397.95):
Calculated: C, 69.42; H, 7.09; Cl, 8.91; N, 10.56%.
Found: C, 69.28; H, 7.06; Cl, 8.82; N, 10.38%.

EXAMPLE 109

3-{6-[4-(3-chlorophenyl)-piperazine-1-yl]-hexyl}-3-ethyl-1,3-dihydro-2H-indol-2-one monohydrochloride The title compound is prepared according to process H starting from 3-(6-bromohexyl)-3-ethyl-1,3-dihydro-2H-indol-2-one and 1-(3-chlorophenyl)-piperazine and the reaction mixture is processed according to method 2.

Melting point, 124-127° C.

IR (KBr): 3073, 1711 (C=O) cm$^{-1}$.

$^1$H-NMR (DMSO-d$_6$, TMS, 200 MHz): 0.50 (3H, t, J=7.3 Hz), 1.02-0.79 (2H, m), 1.31-1.13 (6H, m), 1.78-1.65 (4H, m), 2.20 (2H, t, J=7.0 Hz), 2.40 (4H, t, J=4.8 Hz), 3.12 (4H, t, J=4.8 Hz), 7.02-6.73 (5H, m), 7.24-7.13 (3H, m), 10.33 (1H, s) ppm.

$^{13}$C-NMR (DMSO-d$_6$, TMS, 50.3 MHz): 8.6, 23.9, 26.2, 26.7, 29.2, 30.4, 37.1, 47.8, 52.7, 53.3, 57.8, 109.2, 113.7, 114.6, 118.1, 121.6, 123.0, 127.6, 130.5, 132.5, 134.0, 142.7, 152.4, 181.0 ppm.

Elemental analysis for the Formula C$_{26}$H$_{34}$ClN$_3$O (440.03)
Calculated: C, 70.97; H, 7.79; Cl, 8.06; N, 9.55%.
Measured: C, 71.20; H, 7.56; Cl, 7.86; N, 9.35%.

EXAMPLE 110

3-Ethyl-3-[6-(4-pyridin-2-yl-piperazine-1-yl)-hexyl]-1,3-dihydro-2H-indol-2-one monooxalate The title compound is prepared according to process H applying processing method 3 from 3-(6-bromohexyl)-3-ethyl-1,3-dihydro-2H-indol-2-one and 2-(pyridin-1-yl)-piperazine.

Melting point, 132-135° C.
IR (KBr): 3000-2400, 1702 (C=O) cm$^{-1}$.
$^1$H-NMR (DMSO-d$_6$, TMS, 200 MHz):0.50 (3H, t, J=7.3 Hz), 0.96-0.80 (2H, m), 1.78-1.52 (4H, m), 2.89 (2H, t, J=8.0 Hz), 3.11 (4H, m), 3.70 (4H, m), 6.72 (1H, dd, J=5.1, 7.0 Hz), 7.02-6.81 (3H, m), 7.21-7.12 (2H, m), 7.59 (1H, dt, J=2.1, 7.8 Hz), 8.15 (1H, dd, J=1.3, 5.1 Hz) ppm.
$^{13}$C-NMR (DMSO-d$_6$, TMS, 50.3 MHz): 8.6, 23.4, 23.9, 26.1, 28.9, 30.5, 37.0, 42.2, 50.7, 53.3, 55.8, 107.8, 109.3, 114.3, 121.7, 123.1, 127.7, 132.5, 138.1, 142.7, 147.8, 158.3, 164.5, 181.0 ppm.
Elemental analysis for the Formula C$_{27}$H$_{36}$N$_4$O$_5$ (496.61)
Calculated: C, 65.30; H, 7.31; N, 11.28%.
Measured: C, 64.01; H, 7.40; N, 10.85%.

EXAMPLE 111

3-Ethyl-5-fluoro-3-{4-[4-(4-fluorophenyl)-piperazine-1-yl]-butyl}-1,3-dihydro-2H-indol-2-one The title compound is prepared according to process H by applying processing method 1 starting from 3-(4-chlorobutyl)-3-ethyl-5-fluoro-1,3-dihydro-2H-indol-2-one and 1-(4-fluorophenyl)-piperazine.

Melting point, 119-122° C.
IR (KBr): 3252, 1716 (C=O), 1178 cm$^{-1}$.
$^1$H-NMR (CDCl$_3$, TMS, 500 MHz): 0.63 (3H, t, J=7.4 Hz), 0.94-0.89 (1H, m), 1.14-1.09 (1H, m), 1.48-1.37 (2H, m), 1.80-1.72 (2H, m), 1.96-1.89 (2H, m), 2.25 (2H, t, J=7.7 Hz), 2.51 (4H, t, J=4.9 Hz), 3.06 (4H, t, J=4.9 Hz), 6.95-6.89 (3H, m), 6.87 (1H, dd, J=2.4, 8.2 Hz), 6.86-6.81 (3H, m), 9.53 (1H, s) ppm.
$^{13}$C-NMR (CDCl$_3$, TMS, 125.6 MHz): 8.4, 22.1, 26.8, 30.9, 37.4, 50.0, 53.0, 54.9 (d, J=1.7 Hz), 58.0, 110.1 (d, J=8.1 Hz), 110.8 (d, J=23.9 Hz), 113.9(d, J=23.5 Hz), 115.4 (d, J=22.2 Hz), 117.6 (d, J=7.7 Hz), 134.4 (d, J=7.7 Hz), 137.4 (d, J=1.7 Hz), 147.9 (d, J=2.1 Hz), 157.0 (d, J=238.8 Hz), 159.1 (d, J=240.1 Hz), 182.9 ppm.
Elemental analysis for the Formula C$_{24}$H$_{29}$F$_2$N$_3$O (413.52)
Calculated: C, 69.71; H, 7.07; N, 10.16%.
Measured: C, 69.90; H, 6.96; N, 10.20%.

EXAMPLE 112

3-{4-[4-(3,5-dichlorophenyl)-piperazin-1-yl]-butyl}-3-ethyl-1,3-dihydro-2H-indol-2-one monohydrochloride The title compound is prepared according to process H by applying processing method 2 from 3-(4-chlorobutyl)-3-ethyl-1,3-dihydro-2H-indol-2-one and 1-(3,5-dichlorophenyl)-piperazine.

Melting point, 219-220° C.
IR (KBr): 3205, 2396, 1722 (C=O), 798 cm$^{-1}$.
$^1$H-NMR (DMSO-d$_6$, TMS, 500 MHz): 0.51 (3H, t, J=7.4 Hz), 0.81-0.77 (1H, m), 0.98-0.93 (1H, m), 1.80-1.61 (6H, m), 2.97-2.94 (4H, m), 3.27 (2H, t, J=12.4 Hz), 3.46-3.38 (2H, m), 3.91 (2H, d, J=13.2 Hz), 6.87 (1H, td, J=0.5, 7.7 Hz), 6.94 (1H, t, J=1.7 Hz), 7.00 (1H, dt, J=1.0, 7.6 Hz), 7.03 (2H, d, J=1.7 Hz), 7.18 (1H, dt, J=1.4, 7.7 Hz), 7.21 (1H, td, J=0.6, 7.3 Hz), 10.46 (1H, s), 11.33 (1H, sz) ppm.
$^{13}$C-NMR (DMSO-d$_6$, TMS, 125.6 MHz): 8.6, 21.4, 23.2, 30.3, 36.6, 44.5, 50.1, 53.1, 55.0, 109.4, 113.8, 118.3, 121.7, 123.2, 127.7, 132.1, 134.9, 142.7, 151.4, 180.7 ppm.
Elemental analysis for the Formula C$_{24}$H$_{30}$Cl$_3$N$_3$O (482.89)
Calculated: C, 59.70; H, 6.26; Cl, 22.03; N, 8.70%.
Measured: C, 59.02; H, 6.20; Cl, 21.92; N, 8.69%.

EXAMPLE 113

3-Ethyl-3-{4-[4-(4-fluorophenyl)-piperazin-1-yl]-butyl}-5-methyl-1,3-dihydro-2H-indol-2-one The title compound is prepared according to process H by applying processing method 1 from 3-(4-chlorobutyl)-3-ethyl-5-methyl-1,3-dihydro-2H-indol-2-one and 1-(4-fluorophenyl-)-piperazine.

Melting point, 146-149° C.
IR (KBr): 3170, 1715 (C=O), 1162 cm$^{-1}$.
$^1$H-NMR (DMSO-d$_6$, TMS, 500 MHz): 0.50 (3H, t, J=7.4 Hz), 0.86-0.77 (1H, m), 1.00-0.94 (1H, m), 1.37-1.24 (2H, m), 1.76-1.68 (4H, m), 2.20-2.10 (2H, m), 2.26 (3H, s), 2.38 (4H, sz), 2.99 (4H, t, J=4.9 Hz), 6.73 (1H, d, J=7.8 Hz), 6.90 (2H, dd, J=4.6, 9.3 Hz), 6.96 (1H, d, J=7.8 Hz), 6.99 (1H, s), 7.02 (2H, t, J=8.9 Hz), 10.24 (1H, s) ppm.
$^{13}$C-NMR (DMSO-d$_6$, TMS, 125.3 MHz): 8.6, 21.0, 22.0, 26.5, 30.6, 37.1, 49.1, 52.8, 53.4, 57.6, 108.9, 115.3 (d, J=22.0 Hz), 117.0 (d, J=7.3 Hz), 123.7, 127.9, 130.3, 132.5, 140.2, 148.1 (d, J=2.0 Hz), 156.1 (d, J=235.8 Hz), 181.0 ppm.
Elemental analysis for the Formula C$_{25}$H$_{32}$FN$_3$O (409.55)
Calculated: C, 73.32; H, 7.88; N, 10.26%.
Measured: C, 73.10; H, 7.81; N, 10.12%.

EXAMPLE 114

3-{4-[4-(3,5-dichlorophenyl)-piperazine-1-yl]-butyl}-3-ethyl-5-fluoro-1,3-dihydro-2H-indol-2-one The title compound is prepared according to process H by applying processing method 1 from 3-(4-chlorobutyl)-3-ethyl-5-fluoro-1,3-dihydro-2H-indol-2-one and 1-(3,5-dichlorophenyl)-piperazine.

Melting point, 122-124° C.
IR (KBr): 1719 (C=O), 986, 968, 822 cm$^{-1}$.
$^1$H-NMR (DMSO-d$_6$, TMS, 500 MHz): 0.51 (3H, t, J=7.4 Hz), 0.81-0.77 (1H, m), 1.18-0.95 (1H, m), 1.34-1.27 (2H, m), 1.80-1.69 (4H, m), 2.18-2.13 (2H, m), 2.35 (4H, t, J=5.0 Hz), 3.13 (4H, t, J=5.0 Hz), 6.81 (1H, dd, J=4.4, 8.4 Hz), 6.83 (1H, t, J=1.7 Hz), 6.89 (2H, d, J=1.7 Hz), 6.98 (1H, ddd, J=2.7, 8.4, 9.6 Hz), 7.15 (1H, dd, J=2.7, 8.4 Hz), 10.37 ppm.
$^{13}$C-NMR (DMSO-d$_6$, TMS, 125.6 MHz): 8.5, 21.9, 26.4, 30.4, 36.9, 47.3, 52.4, 54.1 (d, J=1.5 Hz), 57.4, 109.8 (d, J=8.3 Hz), 111.1 (d, J=23.9 Hz), 113.0, 113.8 (d, J=23.4 Hz), 117.0, 134.5 (d, J=7.8 Hz), 134.7, 138.8 (d, J=1.5 Hz), 152.8, 158.3 (d, J=236.3 Hz), 180.9 ppm.
Elemental analysis for the Formula C$_{24}$H$_{28}$Cl$_2$FN$_3$O (464.41)
Calculated: C, 62.07; H, 6.08; Cl, 15.27; N, 9.05%.
Measured: C, 61.84; H, 5.86; Cl, 14.97; N, 8.94%.

EXAMPLE 115

3-{4-[4-(3,4-dichlorophenyl)-piperazin-1-yl]-butyl}-3-ethyl-5-fluoro-1,3-dihydro-2H-indol-2-one The title compound is prepared according to process H by applying processing method 1 from 3-(4-chlorobutyl)-3-ethyl-5-fluoro-1,3-dihydro-2H-indol-2-one and 1-(3,4-dichlorophenyl)-piperazine.

Melting point, 152-155° C.

IR (KBr): 3058, 1709 (C=O), 823, 794 cm$^{-1}$.

$^1$H-NMR (DMSO-d$_6$, TMS, 500 MHz): 0.50 (3H, t, J=7.4 Hz), 0.82-0.76 (1H, m), 0.99-0.92 (1H, m), 1.35-1.24 (2H, m), 2.00-1.67 (4H, m), 2.19-2.11 (2H, m), 2.36 (4H, t, J=5.0 Hz), 3.09 (4H, t, J=5.0 Hz), 6.81 (1H, dd, J=4.4, 8.4 Hz), 6.89 (1H, dd, J=2.9, 9.0 Hz), 6.98 (1H, ddd, J=2.7, 8.4, 9.6 Hz), 7.08 (1H, d, J=2.9 Hz), 7.15 (1H, dd, J=2.7, 8.6 Hz), 7.36 (1H, d, J=9.0 Hz), 10.36 (1H, s) ppm.

$^{13}$C-NMR (DMSO-d$_6$, TMS, 125.6 MHz): 8.5, 21.9, 26.4, 30.4, 36.9, 47.6, 52.4, 54.1, 57.4, 109.8 (d, J=8.3 Hz), 111.2 (d, J=24.4 Hz), 113.8 (d, J=23.4 Hz), 115.3, 116.2, 119.6, 130.6, 131.6, 134.5 (d, J=8.3 Hz), 138.8, 150.9, 158.3 (d, J=236.3 Hz), 180.9 ppm.

Elemental analysis for the Formula C$_{24}$H$_{28}$Cl$_2$FN$_3$O (464.41)

Calculated: C, 62.07; H, 6.08; Cl, 15.27; N, 9.05%.
Measured: C, 61.67; H, 6.00; Cl, 15.16; N, 8.95%.

EXAMPLE 116

3-Etil-5-fluor-3-[4-(4-fenil-piperazin-1-il)-butil]-1,3-dihidro-2H-indol-2-on

The title compound is prepared according to process H by applying processing method 1 from 3-(4-chlorobutyl)-3-ethyl-5-fluoro-1,3-dihydro-2H-indol-2-one and 1-phenylpiperazine.

Melting point, 125-130° C.

IR (KBr): 3032, 1710 (C=O) cm$^{-1}$.

$^1$H-NMR (DMSO-d$_6$, TMS, 500 MHz): 0.51 (3H, t, J=7.4 Hz), 0.86-0.76 (1H, m), 1.04-0.94 (1H, m), 1.40-1.25 (2H, m), 1.80-1.69 (4H, m), 2.19-2.14 (2H, m), 2.39 (4H, s), 3.05 (4H, t, J=4.7 Hz), 6.76 (1H, t, J=7.3 Hz), 6.83 (1H, dd, J=4.4, 8.4 Hz), 6.89 (2H, d, J=8.2 Hz), 6.99 (1H, dt, J=2.7, 9.0 Hz), 7.15 (1H, dd, J=2.6, 8.4 Hz), 7.19 (2H, t, J=7.5 Hz), 10.39 (1H, s) ppm.

$^{13}$C-NMR (DMSO-d$_6$, TMS, 125.6 MHz): 8.5, 22.0, 26.4, 30.4, 36.9, 48.3, 52.8, 54.1 (d, J=2.0 Hz), 57.5, 109.8 (d, J=8.3 Hz), 111.1 (d, J=23.9 Hz), 113.8 (d, J=23.0 Hz), 115.4, 118.9, 129.0, 134.5 (d, J=7.8 Hz), 138.8 (d, J=1.5 Hz), 151.2, 158.3 (d, J=236.3 Hz), 180.9 ppm.

Elemental analysis for the Formula C$_{24}$H$_{30}$FN$_3$O (395.52)

Calculated: C, 72.88; H, 7.65; N, 10.62%.
Measured: C, 71.88; H, 7.71; N, 10.71%.

EXAMPLE 117

3-{4-[4-(3-chloro-4-fluorophenyl)-piperazin-1-yl]-butyl}-3-ethyl-6-fluoro-1,3-dihydro-2H-indol-2-one monohydrochloride The title compound is prepared according to process H by applying processing method 2 from 3-(4-chlorobutyl)-3-ethyl-6-fluoro-1,3-dihydro-2H-indol-2-one and 1-(3-chloro-4-fluorophenyl)-piperazine.

Melting point, 94-96° C.

IR (KBr): 3422, 3159, 2877, 1715, 1504 (C=O) cm$^{-1}$.

$^1$H-NMR (CDCl$_3$, TMS, 500 MHz): 0.60 (3H, t, J=7.4 Hz), 1.08-0.91 (2H, m), 1.93-1.69 (6H, m), 3.03-2.85 (4H, m), 3.5 (6H, sz), 7.07-6.70 (6H, m) 9.5 (1H, s), 12.2 (1H, sz) ppm.

$^{13}$C-NMR (CDCl$_3$, TMS, 125.6 MHz): 8.4, 21.7, 23.4, 31.1, 36.6, 47.2, 51.7, 53.4, 56.9, 98.7 (d, J=26.9 Hz), 108.6 (d, J=22.5 Hz), 117.1, 119.8, 121.3 (d, J=18.5 Hz), 123.7 (d, J=9.8 Hz), 127.0 (d, J=2.9 Hz), 142.9 (d, J=10.3 Hz), 146.5 (d, J=2.9 Hz), 152.4, 154.4, 161.6, 163.5, 182.1 ppm.

Elemental analysis for the Formula C$_{24}$H$_{29}$Cl$_2$F$_2$N$_3$O (484.42)

Calculated: C, 59.51; H, 6.03; Cl, 14.64; N, 8.67%.
Measured: C, 58.84; H, 6.15; Cl, 14.26; N, 8.57%.

EXAMPLE 118

3-Ethyl-6-fluoro-3-{4-[4-(4-fluorophenyl)-piperazin-1-yl]-butyl}-1,3-dihydro-2H-indol-2-one monohydrochloride The title compound is prepared according to process H using processing method 2 from 3-(4-chlorobutyl)-3-ethyl-6-fluoro-1,3-dihydro-2H-indol-2-one and 1-(4-fluorophenyl)-piperazine.

Melting point, 198-202° C.

IR (KBr): 2454, 1715 (C=O) cm$^{-1}$.

$^1$H-NMR (DMSO-d$_6$, TMS, 200 MHz): 0.51 (3H, t, J=7.4 Hz), 0.96-0.79 (2H, m), 1.75-1.65 (6H, m), 3.44-2.93 (10H, m), 7.28-6.67 (7H, m), 10.6 (1H, s), 11.1 (1H, sz) ppm.

Elemental analysis for the Formula C$_{24}$H$_{30}$ClF$_2$N$_3$O (449.98)

Calculated: C, 64.06; H, 6.72; Cl, 7.88; N, 9.34%.
Measured: C, 63.63; H, 6.87; Cl, 7.50; N, 8.94%.

EXAMPLE 119

7-chloro-3-ethyl-5-fluoro-3-{4-[4-(4-fluorophenyl)-piperazin-1-yl]-butyl}-1,3-dihydro-2H-indol-2-one The title compound is prepared according to process H using processing method 1 from 7-chloro-3-(4-chlorobutyl)-3-ethyl-5-fluoro-1,3-dihydro-2H-indol-2-one and 1-(4-fluorophenyl)-piperazine.

Melting point, 161-162° C.

IR (KBr): 2956, 2786, 1721 (C=O) cm$^{-1}$.

$^1$H-NMR (DMSO-d$_6$, TMS, 200 MHz): 0.52 (3H, t, J=7.6 Hz), 0.99-0.75 (2H, m), 1.33-1.27 (2H, m), 1.86-1.68 (4H, m), 2.20-2.14 (2H, m), 2.41-2.36 (4H, m), 3.01-2.97 (4H, m), 7.07-6.87 (4H, m), 7.23 (2H, d, J=8.8 Hz), 10.9 (1H, sz) ppm.

Elemental analysis for the Formula C$_{24}$H$_{28}$ClF$_2$N$_3$O (447.96)

Calculated: C, 64.35; H, 6.30; Cl, 7.91; N, 9.38%.
Measured: C, 64.22; H, 6.40; Cl, 8.06; N, 9.09%.

EXAMPLE 120

7-chloro-3-{4-[4-(4-chlorophenyl)-piperazin-1-yl]-butyl}-3-ethyl-5-fluoro-1,3-dihydro-2H-indol-2-one monohydrochloride The title compound is prepared according to process H by applying processing method 2 from 7-chloro-3-(4-chlorobutyl)-3-ethyl-5-fluoro-1,3-dihydro-2H-indol-2-one and 1-(4-chlorophenyl)-piperazine.

Melting point, 117-119° C.

IR (KBr): 3428, 1719 (C=O) cm$^{-1}$.

$^1$H-NMR (DMSO-d$_6$, TMS, 500 MHz): 0.52 (3H, t, J=7.4 Hz), 0.96-0.80 (2H, m), 1.86-1.64 (6H, m), 3.04-2.96 (2H, m), 3.20-3.15 (2H, m), 3.77-3.75 (2H, m), 3.91 (4H, m), 7.30-6.99 (6H, m), 10.9 (1H, s), 11.3 (1H, sz) ppm.

Elemental analysis for the Formula $C_{24}H_{29}Cl_3FN_3O$ (500.88)

Calculated: C, 57.55; H, 5.84; Cl, 21.23; N, 8.39%.
Measured: C, 56.31; H, 5.94; Cl, 21.81; N, 8.06%.

EXAMPLE 121

5-chloro-3-{4-[4-(4-chlorophenyl)-piperazin-1-yl]-butyl}-3-ethyl-1,3-dihydro-indol-2-one The title compound is prepared according to process H by applying processing method 1 from 5-chloro-3-(4-chlorobutyl)-3-ethyl-1,3-dihydro-2H-indol-2-one and 1-(4-chlorophenyl)-piperazine.

Melting point, 186-188° C.

IR (KBr): 3286, 2934, 1715 (C=O), 1694 cm$^{-1}$.

$^1$H-NMR (DMSO-d$_6$, TMS, 200 MHz): 0.64 (3H, t, J=7.3 Hz), 1.11-0.91 (2H, m), 1.43-1.37 (2H, m), 1.98-1.71 (4H, m), 2.28-2.21 (2H, m), 2.52-2.47 (4H, m), 3.13-3.08 (4H, m), 6.86-6.77 (3H, m), 7.27-7.09 (4H, m), 8.9 (1H, sz) ppm.

Elemental analysis for the Formula $C_{24}H_{29}Cl_2N_3O$ (446.42)

Calculated: C, 64.57; H, 6.55; Cl, 15.88; N, 9.41%.
Measured: C, 64.86; H, 6.59; Cl, 15.59; N, 9.39%.

EXAMPLE 122

5-chloro-3-{4-[4-(4-chlorophenyl)-piperazin-1-yl]-butyl}-3-ethyl-6-fluoro-1,3-dihydro-2H-indol-2-one The title compound is prepared according to process H by applying processing method 2 from 5-chloro-3-(4-chlorobutyl)-3-ethyl-6-fluoro-1,3-dihydro-2H-indol-2-one and 1-(4-chlorophenyl)-piperazine.

Melting point, 194-197° C.

IR (KBr): 3283, 2934, 1717 (C=O), 1692 cm$^{-1}$.

$^1$H-NMR (DMSO-d$_6$, TMS, 500 MHz): 0.50 (3H, t, J=7.6 Hz), 0.95-0.78 (2H, m), 1.33-1.26 (2H, m), 1.82-1.66 (4H, m), 2.19-2.14 (2H, m), 2.38 (4H, s), 3.05 (4H, s), 6.92-6.84 (3H, m), 7.21 (2H, m), 7.47 (1H, m), 10.6 (1H, s) ppm.

Elemental analysis for the Formula $C_{24}H_{28}Cl_2FN_3O$ (464.41)

Calculated: C, 62.07; H, 6.08; Cl, 15.27; N, 9.05%.
Measured: C, 61.94; H, 6.24; Cl, 14.62; N, 8.64%.

EXAMPLE 123

3-{5-[4-(4-chlorophenyl)-piperazin-1-yl]-pentyl}-3-ethyl-1,3-dihydro-2H-indol-2-one The title compound is prepared according to process H by applying processing method 1 from 3-(5-chloropentyl)-3-ethyl-1,3-dihydro-2H-indol-2-one and 1-(4-chlorophenyl)-piperazine.

Melting point, 142-143° C.

IR (KBr): 2939, 1700 (C=O) cm$^{-1}$.

$^1$H-NMR (DMSO-d$_6$, TMS, 500 MHz): 0.50 (3H, t, J=7.6 Hz), 0.97-0.78 (2H, m), 1.14 (2H, m), 1.30 (2H, m), 1.70 (4H, m), 2.16 (2H, m), 2.39 (4H, m), 3.06 (4H, m), 7.22-6.82 (8H, m), 10.3 (1H, s) ppm.

Elemental analysis for the Formula $C_{25}H_{32}ClN_3O$ (426.01)

Calculated: C, 70.49; H, 7.57; Cl, 8.32; N, 9.86%.
Measured: C, 70.23; H, 7.50; Cl, 8.13; N, 9.99%.

EXAMPLE 124

5,7-dichloro-3-{4-[4-(3,4-dichlorophenyl)-piperazin-1-yl]-butyl}-3-ethyl-1,3-dihydro-2H-indol-2-one The title compound is prepared according to process H by applying processing method 1 from 5,7-dichloro-3-(4-chlorobutyl)-3-ethyl-1,3-dihydro-2H-indol-2-one and 1-(3,4-dichlorophenyl)-piperazine.

Melting point, 164-165° C.

IR (KBr): 2969, 1734 (C=O) cm$^{-1}$.

$^1$H-NMR (DMSO-d$_6$, TMS, 500 MHz): 0.51 (3H, t, J=7.4 Hz), 0.98-0.78 (2H, m), 1.36-1.26 (2H, m), 1.84-1.70 (4H, m), 2.20-2.14 (2H, m), 2.36 (4H, sz), 3.10 (4H, m), 6.88 (1H, m), 7.08 (1H, s), 7.38-7.36 (2H, m), 7.40 (1H, s), 11.0 (1H, s) ppm.

Elemental analysis for the Formula $C_{24}H_{27}Cl_4N_3O$ (515.31)

Calculated: C, 55.94; H, 5.28; Cl, 27.52; N, 8.15%.
Measured: C, 56.35; H, 5.18; Cl, 27.12; N, 8.10%.

EXAMPLE 125

5,7-Dichloro-3-{5-[4-(4-chlorophenyl)-piperazin-1-yl]-pentyl}-3-ethyl-1,3-dihydro-2H-indol-2-one The title compound is prepared according to process H by applying processing method 1 from 5,7-dichloro-3-(5-chloropentyl)-3-ethyl-1,3-dihydro-2H-indol-2-one and 1-(4-chlorophenyl)-piperazine.

Melting point, 145-148° C.

IR (KBr): 2963, 1723 (C=O) cm$^{-1}$.

$^1$H-NMR (DMSO-d$_6$, TMS, 500 MHz): 0.51 (3H, t, J=7.3 Hz), 0.98-0.77 (2H, m), 1.15 (2H, m), 1.32 (2H, m), 1.85-1.68 (4H, m), 2.17 (2H, m), 2.40 (4H, sz), 3.06 (4H, sz), 6.92 (2H, m), 7.21 (2H, m), 7.38 (2H, m), 10.99 (1H, s) ppm.

Elemental analysis for the Formula $C_{25}H_{30}Cl_3N_3O$ (494.90)

Calculated: C, 60.68; H, 6.11; Cl, 21.49; N, 8.49%.
Measured: C, 60.59; H, 6.20; Cl, 21.14; N, 8.51%.

EXAMPLE 126

3-{4-[4-(2-chloro-4-fluorophenyl)-piperazin-1-yl]-butyl}-3-ethyl-1,3-dihydro-2H-indol-2-one The title compound is prepared according to process H by applying processing method 1 from 3-(4-chlorobutyl)-3-ethyl-1,3-dihydro-2H-indol-2-one and 1-(2-chloro-4-fluorophenyl)-piperazine.

Melting point, 125-126° C.

IR (KBr): 3168, 2877, 1713 (C=O), 1507 cm$^{-1}$.

$^1$H-NMR (CDCl$_3$, TMS, 500 MHz): 0.63 (3H, t, J=7.4 Hz), 0.93-0.88 (1H, m), 1.13-1.09 (1H, m), 1.46-1.35 (2H, m), 1.81-1.75 (2H, m), 1.96-1.89 (2H, m), 2.25-2.21 (2H, m), 2.48 (4H, sz), 3.05 (4H, sz), 6.71 (1H, m), 6.86 (1H, m), 6.92 (1H, m), 6.97 (1H, m), 7.05 (1H, m), 7.11 (1H, m), 7.20 (1H, m), 9.02 (1H, s) ppm.

Elemental analysis for the Formula $C_{24}H_{29}ClFN_3O$ (429.97)

Calculated: C, 67.04; H, 6.80; Cl, 8.25; N, 9.77%.
Measured: C, 67.47; H, 6.85; Cl, 8.17; N, 9.58%.

EXAMPLE 127

3-Ethyl-3-{4-[4-(4-fluoro-2-methylphenyl)-piperazin-1-yl]-butyl}-1,3-dihydro-2H-indol-2-one monohydrochloride The title compound is prepared according to process H by applying processing method 2 from the starting compounds 3-(4-chlorobutyl)-3-ethyl-1,3-dihydro-2H-indol-2-one and 1-(4-fluoro-2-methylphenyl)-piperazine.

Melting point, 103-107° C.

IR (KBr): 3424, 1499, 1321 cm$^{-1}$.

$^1$H-NMR (DMSO-$d_6$, TMS, 500 MHz): 0.49 (3H, t, J=7.3 Hz), 0.83-0.75 (1H, m), 0.98-0.91 (1H, m), 1.79-1.59 (6H, m), 2.22 (3H, s), 3.05 (6H, sz), 3.35 (4H, sz), 6.84 (1H, m), 6.98 (2H, m), 7.02 (2H, m), 7.16 (1H, m), 7.19 (1H, m), 10.4 (1H, s), 11.1 (1H, sz) ppm.

Elemental analysis for the Formula $C_{25}H_{33}ClFN_3O$ (446.01)

Calculated: C, 67.33; H, 7.46; Cl, 7.95; N, 9.42%.
Measured: C, 66.31; H, 7.68; Cl, 7.72; N, 9.15%.

EXAMPLE 128

5,7-dichloro-3-{4-[4-(4-chlorophenyl)-piperazin-1-yl]-butyl}-3-methyl-1,3-dihydro-2H-indol-2-one The title compound is prepared according to process H by applying processing method 1 starting from 5,7-dichloro-3-(4-chlorobutyl)-3-methyl-1,3-dihydro-2H-indol-2-one and 1-(4-chlorophenyl)-piperazine.

Melting point, 168-170° C.

IR (KBr): 296, 1731 (C=O), 1497 cm$^{-1}$.

$^1$H-NMR (DMSO-$d_6$, TMS, 500 MHz): 0.85-0.78 (1H, m), 0.99-0.91 (1H, m), 1.27 (3H, s), 1.33 (2H, m), 1.85-1.71 (2H, m), 2.22-2.13 (2H, m), 2.38 (4H, sz), 3.05 (4H, sz), 6.90 (2H, d, J=8.9 Hz), 7.20 (2H, d, J=9.0 Hz), 7.40 (2H, m), 10.96 (1H, s) ppm.

Elemental analysis for the Formula $C_{23}H_{26}Cl_3N_3O$ (466.84)

Calculated: C, 59.18; H, 5.61; Cl, 22.78; N, 9.00%.
Measured: C, 58.97; H, 5.77; Cl, 22.65; N, 8.74%.

What we claim is:

1. A 3,3-Dialkyl indol-2-one derivative of the general Formula (I), (I)

wherein $R^1$ stands for hydrogen, halogen, alkyl having 1-7 carbon atom(s) or sulfonamido; $R^2$ represents hydrogen or halogen; $R^3$ is hydrogen; $R^4$ stands for ethyl or 2-methylpropyl; $R^5$ is a group of the general Formula (II a) or (II b), (IIa)

(IIb)

wherein Q is nitrogen and W is CH; $R^6$, $R^7$ and $R^8$ each stands for hydrogen, halogen or alkoxy having 1-7 carbon atom(s), or $R^6$ and $R^7$ together represent ethylenedioxy; m is 0 or 1; a is a single bond; n is 1; or a pharmaceutically acceptable acid addition salt thereof.

2. A 3,3-dialkyl indol-2-one derivative, which is:
5-chloro-3-{3-[4-(3-chlorophenyl)-piperazin-1-yl]-propyl}-3-ethyl-1,3-dihydro-2H-indol-2-one, 3-{4-[4-(3-chlorophenyl)-piperazin-1-yl]-butyl}-3-ethyl-5-fluoro-1,3-dihydro-2H-indol-2-one, 5,7-dichloro-3-{4-[4-(4-chlorophenyl)-piperazin-1-yl]-butyl}-3-ethyl-1,3-dihydro-2H-indol-2-one, 3-{4-[4-(4-chlorophenyl)-piperazin-1-yl]-butyl}-3-ethyl-1,3-dihydro-2H-indol-2-one, 3-{4-[4-(4-chlorophenyl)-piperazin-1-yl]-butyl}-3-ethyl-5-fluoro-1,3-dihydro-2H-indol-2-one, 3-{4-[4-(3-chlorophenyl)-piperazin-1-yl]-butyl}-3-ethyl-1,3-dihydro-2H-indol-2-one-5-sulfonamide, 3-{4-[4-(2,3-dihydrobenzo[1,4]dioxin-5-yl)-piperazin-1-yl]-butyl}-3-ethyl-1,3-dihydro-2H-indol-2-one, 3-{4-[4-(2,3-Dihydrobenzo[1,4]dioxin-5-yl)-piperazin-1-yl]-butyl}-3-isobutyl-1,3-dihydro-2H-indol-2-one, 3-Ethyl-3-{4-[4-(2-methoxyphenyl)-piperazin-1-yl]-butyl}-1,3-dihydro-2H-indol-2-one, or a pharmaceutically acceptable acid addition salt thereof.

3. 5-Chloro-3-{3-[4-(3-chlorophenyl)-piperazin-1-yl]-propyl}-3-ethyl-1,3-dihydro-2H-indol-2-one, or a pharmaceutically acceptable acid addition salt thereof.

4. 3-{4-[4-(3-Chlorophenyl)-piperazin-1-yl]-butyl}-1-3-ethyl-5-fluoro-1,3-dihydro-2H-indol-2-one, or a pharmaceutically acceptable acid addition salt thereof.

5. 5,7-Dichloro-3-{4 [4-(4-chlorophenyl)-piperazin-1-yl] 1-butyl}1-3-ethyl-1,3-dihydro-2H-indol-2-one, or a pharmaceutically acceptable acid addition salt thereof.

6. 3-{4-[4-(4-Chlorophenyl)-piperazin-1-yl]-butyl}-3-ethyl-1,3-dihydro-2H-indol-2-one, or a pharmaceutically acceptable acid addition salt thereof.

7. 3-{4-[4-(4-Chlorophenyl)-piperazin-1-yl]-butyl}-3-ethyl-5-fluoro-1,3-dihydro-2H-indol-2-one, or a pharmaceutically acceptable acid addition salt thereof.

8. 3-{4-[4-(3-Chlorophenyl)-piperazin-1-yl]-butyl}-3-ethyl-1,3-dihydro-2H-indol 1-2-one-5-sulfonamide, or a pharmaceutically acceptable acid addition salt thereof.

9. 3-{4-[4-(2,3-Dihydrobenzo[1,4]dioxin-5-yl)-piperazin-1-yl]-butyl}1-3-ethyl-1,3-dihydro-2H-indol-2-one, or a pharmaceutically acceptable acid addition salt thereof.

10. 3-{4-[4-(2,3-Dihydrobenzo[1,4]dioxin-5-yl)-piperazin-1-yl]-butyl}-3-isobutyl-1,3-dihydro-2H-indol-2-one, or a pharmaceutically acceptable acid addition salt thereof.

11. 3-Ethyl-3-{4-[4-(2-methoxyphenyl)-piperazin-1-yl]-butyl}-1,3-dihydro-2H-indol-2-one, or a pharmaceutically acceptable acid addition salt thereof.

12. A pharmaceutical composition comprising as active ingredient at least a compound of the general Formula (I) according to claim 1 or a pharmaceutically acceptable acid addition salt thereof in admixture with one or more conventional carrier(s) or auxiliary agent(s).

13. A method for the treatment of anxiety comprising,
administering a therapeutically effective amount of the pharmaceutical composition of claim 12 to a subject in need thereof.

14. A pharmaceutical composition comprising a) one or more conventional carrier(s) or auxiliary agent(s) and, as an active ingredient, b) 5-chloro-3-{3[4-(3-chlorophenyl)-piperazin-1-yl]-propyl}-3-ethyl-1,3-dihydro-2H-indol-2-one, 3-{4-[4-(3-chlorophenyl)-piperazin-1-yl]-butyl}-3-ethyl-5-fluoro-1,3-dihydro-2H-indol-2-one, 5,7-dichloro-3-{4-[4-(4-chlorophenyl)-piperazin-1-yl]-butyl}-3-ethyl-1,3-dihydro-2H-indol-2-one, 3-{4-[4-(4-chlorophenyl)-piperazin-1-yl]-butyl}-3-ethyl-1,3-dihydro-2H-indol-2-one, 3-{4-[4-(4-chlorophenyl)-piperazin-1-yl]-butyl}-3-ethyl-5-fluoro-1,3-dihydro-2H-indol-2-one, 3-{4-[4-(3-chlorophenyl)-piperazin-1-yl]-butyl}1-3-ethyl-1,3-dihydro-2H-indol-2-one-5-sulfonamide, 3-{4-[4-(2,3-dihydrobenzo[1,4]dioxin-5-yl)-piperazin-1-yl]-butyl}-3-ethyl-1,3-dihydro-2H-indol-2-one, 3-{4-[4-(2,3-dihydrobenzo[1,4]dioxin-5-yl)-piperazin-1yl]-butyl}-3-isobutyl-1,3-dihydro-2H-indol-2-one, or 3-ethyl-3-{4-[4-(2-methoxyphenyl)-piperazin-1-yl]-butly}-1,3-dihydro- 2H-indol-2-one or a pharmaceutically acceptable acid addition salt thereof.

15. A process for the preparation of a 3,3-dialkyl indol-2-one derivative or a pharmaceutically acceptable acid addition salt thereof according to claim 1, which comprises (a) reacting a compound of the general Formula (III),

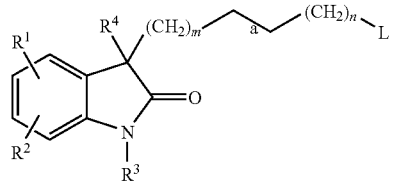

(III)

wherein $R^1$ is hydrogen, halogen, alkyl having 1-7 carbon atom(s) or sulfonamido; $R^2$ is hydrogen or halogen; $R^3$ is hydrogen; $R^4$ is ethyl or 2-methyl-propyl; m is 0 or 1; a is a single bond; n is 1; and L is a leaving group, with a piperazine derivative of the general Formula (IV),

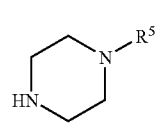

(IV)

wherein $R^5$ is a group of the Formula (II a) or (II b),

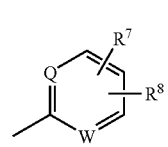

(IIa)

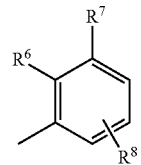

(IIb)

wherein Q is nitrogen and W is CH; $R^6$, $R^7$ and $R^8$ each stands for hydrogen, halogen, or alkoxy having 1-7 carbon atom(s), or $R^6$ and $R^7$ together represent ethylenedioxy, in the presence of an acid binding agent; or (b) reacting a compound of the general Formula (VI),

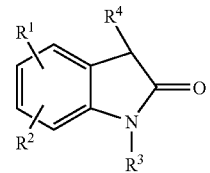

(VI)

wherein $R^1$, $R^2$, $R^3$ and $R^4$ are as stated above, with a compound of the general Formula (VII),

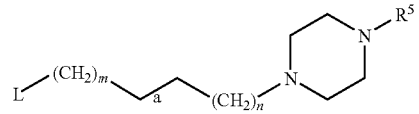

(VII)

wherein m, n and a are as stated above, and L is a leaving group, in the presence of a strong base; or (c) for the preparation of compounds of the general Formula (I) according to claim 2, wherein n is 1 and a stands for a single bond, reacting a compound of the general Formula (VIII),

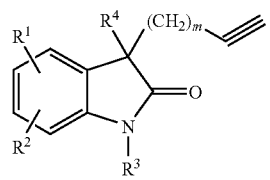

(VIII)

wherein, $R^1 R^2$, $R^3$, $R^4$ and m are as stated above, with formaldehyde, optionally converting the thus-obtained compound of the general Formula (III), wherein L stands for a hydroxy group, into a compound of the general Formula (III), wherein L is a halogen atom or an arylsulfonyloxy or alkylsulfonyloxy group, and reacting the thus-obtained compound of the general Formula (III), wherein a is a single bond and n is 1, with a compound of the general Formula (IV) in the presence of a strong base; or (d) for the preparation of the compounds of the general Formula (I) according to claim 2, wherein $R^1$, $R_2$, $R^3$, $R^4$, $R^5$, m and n are as stated above and a stands for a single bond, subjecting the corresponding compound of the general Formula (I), wherein a stands for a triple bond, to reduction; or (e) for the preparation of the compounds of the general Formula (I) according to claim 2, wherein $R^1$, $R^2$, $R^3$, $R^4$, $R^5$, m and n are as stated above and a represents a single bond, subjecting the corresponding compound of the general Formula (I), wherein a stands for a double or triple bond, to reduction, and, optionally, halogenating the product containing hydrogen at $R^2$, or liberating the free base from its salt or converting it into a pharmaceutically acceptable acid addition salt with an organic or inorganic acid.

16. A process for the manufacture of a pharmaceutical comprising, admixing at least one compound of the general Formula (I) according to claim 1 or a pharmaceutically acceptable acid addition salt thereof with a pharmaceutical carrier and optionally other auxiliary agent and bringing the mixture to galenic form.

17. The method of claim 13, wherein the administered amount of the compound of the general Formula (I) or the pharmaceutically acceptable acid addition salt thereof is between 0.1 mg/kg body weight and 1000 mg/kg body weight per day.

* * * * *